(12) United States Patent
Clarke et al.

(10) Patent No.: US 9,617,295 B2
(45) Date of Patent: Apr. 11, 2017

(54) 2'-CHLORO AMINOPYRIMIDINONE AND PYRIMIDINE DIONE NUCLEOSIDES

(71) Applicant: Gilead Sciences, Inc., Foster City, CA (US)

(72) Inventors: Michael O'Neil Hanrahan Clarke, Redwood City, CA (US); Richard L. Mackman, Millbrae, CA (US); Dustin Siegel, San Carlos, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/830,121

(22) Filed: Aug. 19, 2015

(65) Prior Publication Data

US 2016/0052953 A1 Feb. 25, 2016

Related U.S. Application Data

(60) Provisional application No. 62/040,349, filed on Aug. 21, 2014.

(51) Int. Cl.
*C07H 19/073* (2006.01)
*C07H 19/10* (2006.01)
*C07H 19/06* (2006.01)

(52) U.S. Cl.
CPC ............ *C07H 19/06* (2013.01); *C07H 19/073* (2013.01); *C07H 19/10* (2013.01)

(58) Field of Classification Search
None
See application file for complete search history.

(56) References Cited

U.S. PATENT DOCUMENTS 9,073,960 B2 * 7/2015 Beigelman ............. C07H 19/00
2012/0070415 A1 3/2012 Beigelman et al.
2013/0165400 A1 6/2013 Beigelman et al.

OTHER PUBLICATIONS

Intl. Search Report dated Oct. 19, 2015 for PCT/US2015/045849.
Written Opinion dated Oct. 19, 2015 for PCT/US2015/045849.

* cited by examiner

*Primary Examiner* — Traviss C McIntosh, III

(57) ABSTRACT

Provided herein are formulations, methods and substituted 2'-chloro aminopyrimidinone and pyrimidine dione compounds of Formula (I) for treating Pneumovirinae virus infections, including respiratory syncytial virus infections, as well as methods and intermediates for synthesis of substituted 2'-chloro aminopyrimidinone and pyrimidine dione compounds.

21 Claims, No Drawings

2'-CHLORO AMINOPYRIMIDINONE AND PYRIMIDINE DIONE NUCLEOSIDES

CROSS REFERENCE TO RELATED APPLICATIONS

This application claims the benefit of U.S. Provisional Application No. 62/040,349, filed on Aug. 21, 2014, which is hereby incorporated by reference in its entirety.

FIELD OF THE INVENTION

Provided herein are substituted 2'-chloro aminopyrimidinone and pyrimidine dione compounds, methods and pharmaceutical formulations for treating Pneumovirinae virus infections, particularly including respiratory syncytial virus infections, and methods and intermediates useful for preparing the compounds.

BACKGROUND OF THE INVENTION

Pneumovirinae viruses are negative-sense, single-stranded, RNA viruses that are responsible for many prevalent human and animal diseases. The Pneumovirinae subfamily of viruses is a part of the family Paramyxoviridae and includes human respiratory syncytial virus (HRSV). Almost all children will have had an HRSV infection by their second birthday. HRSV is the major cause of lower respiratory tract infections in infancy and childhood with 0.5% to 2% of those infected requiring hospitalization. The elderly and adults with chronic heart, lung disease or those that are immunosuppressed also have a high risk for developing severe HRSV disease (http://www.cdc.gov/rsv/index.html). No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumovirinae therapeutics.

Examples of pyrrolo[2,3-d]pyrimidine compounds useful for treating viral infections are described in U.S. 2012/0009147 A1 (Cho et al.), U.S. 2012/0020921 A1 (Cho et al.), WO 2008/089105 A2 (Babu et al.), WO 2008/141079 A1 (Babu et al.), WO 2009/132135 A1 (Butler et al.), WO 2010/002877 A2 (Francom), WO 2011/035231 A1 (Cho et al.), WO 2011/035250 A1 (Butler et al.), WO 2011/150288 A1 (Cho et al.), WO 2012/012465 (Cho et al.), WO 2012/012776 A1 (Mackman et al.), WO 2012/037038 (Clarke et al.), WO 2012/087596 A1 (Delaney et al.), and WO 2012/142075 A1 (Girijavallabhan et al.).

There remains a need for new antiviral agents useful in treating Paramyxoviridae viral infections, including Pneumovirinae viral infections, such as HRSV infections, that are effective and have acceptable toxicity profiles.

SUMMARY

Provided are compounds, methods, and pharmaceutical formulations for the treatment of infections caused by the Pneumovirinae virus family, including treatment of infections caused by human respiratory syncytial virus.

Provided is a compound of Formula I, or a pharmaceutically acceptable salt thereof:

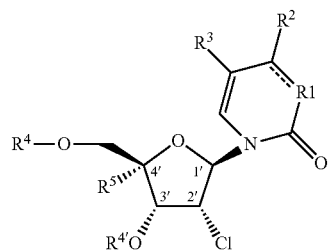

wherein:
$R^1$ is selected from NH and N;
the dashed line (- - - -), in conjunction with the solid line to which it is parallel, represents an optional double bond;
$R^2$ is selected from oxo or $NH_2$, with the proviso that, when $R^2$ is oxo, $R^1$ is NH and the bond represented by the dashed line (- - - -), in conjunction with the solid line to which it is parallel, is a single bond; and with the proviso that, when $R^2$ is $NH_2$, $R^1$ is N and the bond represented by the dashed line (- - - -), in conjunction with the solid line to which it is parallel, is a double bond;
$R^3$ is selected from the group of H, F, $CH_2F$, $CHF_2$, and $CF_3$;
$R^5$ is selected from the group of CN, unsubstituted $C_1$-$C_4$ alkyl, $C_1$-$C_4$ alkyl substituted with 1, 2, or 3 halogens, $C_1$-$C_4$ alkyl substituted with 1 substituent selected from —S—$CH_3$ and —O—$CH_3$, $C_2$-$C_4$ alkenyl, $C_2$-$C_4$ alkynyl, unsubstituted $C_3$-$C_6$ cycloalkyl, $C_3$-$C_6$ cycloalkyl substituted by 1, 2, or 3 substituents selected from F and $CH_3$;
$R^{4'}$ is selected from the group of H, —C(=O)$R^6$, —C(=O)O$R^6$, and —C(=O)N$R^6R^7$;
$R^4$ is selected from the group of H, —C(=O)$R^6$, —C(=O)O$R^6$, and —C(=O)N$R^6R^7$;
or
a) $R^4$ is a group of the formula:

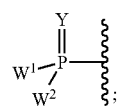

wherein:
each Y is O, S, NR, $^+$N(O)(R), N(OR), $^+$N(O)(OR), or N—$NR_2$; and
$W^1$ and $W^2$, when taken together, are —$Y^3$(C($R^y$)$_2$)$_3Y^3$—;
or one of $W^1$ or $W^2$ together with $R^{4'}$ is —$Y^3$— and the other of $W^1$ or $W^2$ is Formula Ia;
or $W^1$ and $W^2$ are each, independently, a group of the Formula Ia:

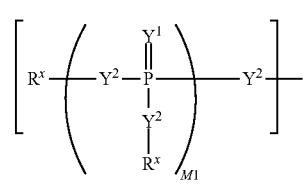

Formula Ia wherein:
each $Y^1$ is, independently, O, S, NR, $^+$N(O)(R), N(OR), $^+$N(O)(OR), or N—$NR_2$;

each $Y^2$ is independently a bond, O, $CR_2$, —O—$CR_2$—, NR, $^+$N(O)(R), N(OR), $^+$N(O)(OR), N—$NR_2$, S, S—S, S(O), or $S(O)_2$;

each $Y^3$ is a single bond;

M1 is 0, 1, 2, or 3;

each $R^x$ is independently $R^y$ or the formula:

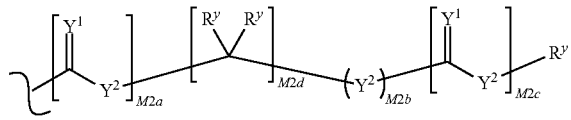

wherein:

each M2a, M2b, and M2c is independently 0 or 1;

M2d is 0, 1, 2, 3, 4, 5, 6, 7, 8, 9, 10, 11 or 12;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —SO$_2$NR$_2$, —CN, —N$_3$, —NO$_2$, —OR, or $W^3$;

or when taken together, two $R^y$ on the same carbon atom form a carbocyclic ring having 3, 4, 5, 6, or 7 carbon ring atoms;

or when taken together, two $R^y$ on the same carbon atom form along with the carbon atom a heterocycle having 3, 4, 5, 6, or 7 ring atoms wherein one ring atom is selected from O or N and all other ring atoms are carbon;

each R is independently H, ($C_1$-$C_8$) alkyl, ($C_1$-$C_8$) substituted alkyl, ($C_2$-$C_8$)alkenyl, ($C_2$-$C_8$) substituted alkenyl, ($C_2$-$C_8$) alkynyl, ($C_2$-$C_8$) substituted alkynyl, $C_6$-$C_{10}$ aryl, $C_6$-$C_{10}$ substituted aryl, a 3- to 10-membered heterocycle, a substituted 3- to 10-membered heterocycle, a 5- to 12-membered heteroaryl, a substituted 5- to 12-membered heteroaryl, arylalkyl, substituted arylalkyl, heteroarylalkyl, or substituted heteroarylalkyl; and $W^3$ is $W^4$ or $W^5$;

$W^4$ is R, —C($Y^1$)$R^y$, —C($Y^1$)$W^5$, —SO$_2$$R^y$, or —SO$_2$$W^5$;

$W^5$ is selected from phenyl, naphthyl, a $C_3$-$C_8$ carbocycle, or a 3- to 10-membered heterocycle, wherein $W^5$ is independently substituted with 0, 1, 2, 3, 4, 5, or 6 $R^y$ groups;

each $R^6$ and $R^7$ is independently H, ($C_1$-$C_8$)alkyl, ($C_2$-$C_8$)alkenyl, ($C_2$-$C_8$)alkynyl, ($C_4$-$C_8$)carbocyclylalkyl, $C_6$-$C_{10}$ aryl, $C_6$-$C_{10}$ substituted aryl, 5- to 10-membered heteroaryl, substituted 5- to 10-membered heteroaryl, —C(=O)($C_1$-$C_8$) alkyl, —S(O)$_n$($C_1$-$C_8$)alkyl or aryl($C_1$-$C_8$)alkyl;

or $R^6$ and $R^7$ taken together with a nitrogen to which they are both attached form a 3- to 7- membered heterocycle wherein any one ring carbon atom of said heterocycle can optionally be replaced with —O—, —S— or —NR$^a$—;

and wherein each ($C_1$-$C_8$)alkyl, ($C_2$-$C_8$)alkenyl, ($C_2$-$C_8$) alkynyl or aryl($C_1$-$C_8$)alkyl of each $R^6$ or $R^7$ is, independently, optionally substituted with one, two, three, or four substituents selected from halo, hydroxy, CN, N$_3$, N(R$^a$)$_2$ or OR$^a$; and wherein one, two, or three of the non-terminal carbon atoms of each said ($C_1$-$C_8$)alkyl may be optionally replaced with —O—, —S— or —NR$^a$—; or b) $R^4$ is a group selected from:

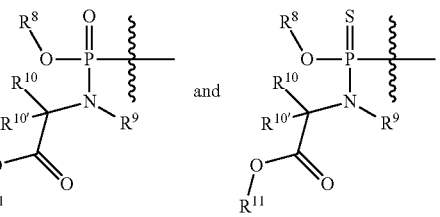

wherein:
$R^8$ is selected from phenyl, 1-naphthyl, 2-naphthyl,

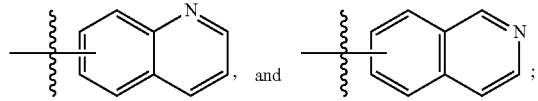

$R^9$ is selected from H and CH$_3$;
$R^{10}$ is selected from H or C$_1$-C$_6$ alkyl;
$R^{10'}$ is selected from H or C$_1$-C$_6$ alkyl;
or $R^{10}$ and $R^{10'}$, together with the carbon atom to which they are bound, form a 3-, 4-, 5-, or 6-membered spirocycle wherein all ring atoms of the spirocycle are carbon;
or $R^{10}$ and $R^{10'}$, together with the carbon atom to which they are bound, form a 3-, 4-, 5-, or 6-membered spirocycle wherein 1 or 2 of the ring atoms of the spirocycle are selected from the group of O, S, and N, and all other ring atoms of the spirocycle are carbon;
$R^{11}$ is selected from H, C$_1$-C$_8$ alkyl, benzyl, C$_3$-C$_6$ cycloalkyl, —CH$_2$—C$_3$-C$_6$ cycloalkyl, —CH$_2$CH$_2$—S—C(O)—C$_3$-C$_6$ alkyl,

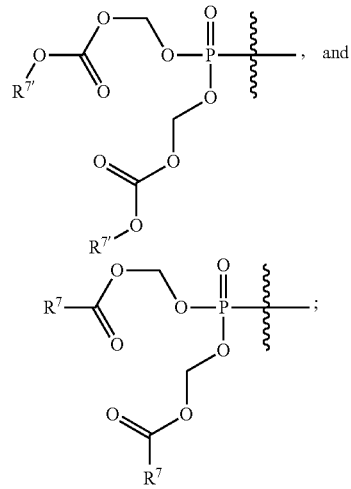

$R^{7'}$ is selected from C$_1$-C$_8$ alkyl, —O—C$_1$-C$_8$ alkyl, benzyl, —O-benzyl, —CH$_2$—C$_3$-C$_6$ cycloalkyl, and CF$_3$; or c) $R^4$ and $R^{4'}$ combine to form the structure selected from:

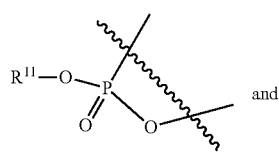

-continued

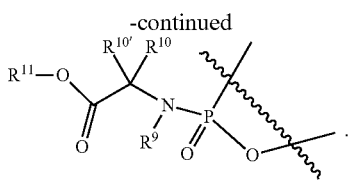

and $R^a$ in each appearance is independently selected from H and $C_1$-$C_6$ alkyl, two adjacent $R^a$ in the group —$N(R_a)_2$ can together form a 4-, 5-, or 6-membered heterocyclic ring containing 0 or 1 additional ring heteroatom selected from O or N.

DETAILED DESCRIPTION

Provided is a compound of Formula I, or a pharmaceutically acceptable salt thereof:

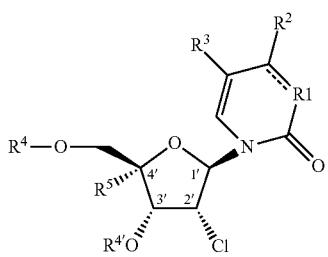

(I)

wherein:
$R^1$ is selected from NH and N;
the dashed line (- - - -), in conjunction with the solid line to which it is parallel, represents an optional double bond;
$R^2$ is selected from oxo or $NH_2$, with the proviso that, when $R^2$ is oxo, $R^1$ is NH and the bond represented by the dashed line (- - - -), in conjunction with the solid line to which it is parallel, is a single bond; and with the proviso that, when $R^2$ is $NH_2$, $R^1$ is N and the bond represented by the dashed line (- - - -), in conjunction with the solid line to which it is parallel, is a double bond;
$R^3$ is selected from the group of H, F, $CH_2F$, $CHF_2$, and $CF_3$;
$R^5$ is selected from the group of CN, unsubstituted $C_1$-$C_4$ alkyl, $C_1$-$C_4$ alkyl substituted with 1, 2, or 3 halogens, $C_1$-$C_4$ alkyl substituted with 1 substituent selected from —S—$CH_3$ and —O—$CH_3$, $C_2$-$C_4$ alkenyl, $C_2$-$C_4$ alkynyl, unsubstituted $C_3$-$C_6$ cycloalkyl, $C_3$-$C_6$ cycloalkyl substituted by 1, 2, or 3 substituents selected from F and $CH_3$;
$R^{4'}$ is selected from the group of H, —C(=O)$R^6$, —C(=O)O$R^6$, and —C(=O)N$R^6R^7$;
$R^4$ is selected from the group of H, —C(=O)$R^6$, —C(=O)O$R^6$, and —C(=O)N$R^6R^7$;
or
b) $R^4$ is a group of the formula:

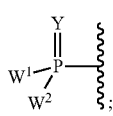

wherein:
each Y is O, S, NR, $^+$N(O)(R), N(OR), $^+$N(O)(OR), or N—$NR_2$; and $W^1$ and $W^2$, when taken together, are —$Y^3(C(R^y)_2)_3Y^3$—;
or one of $W^1$ or $W^2$ together with $R^{4'}$ is —$Y^3$— and the other of $W^1$ or $W^2$ is Formula Ia;
or $W^1$ and $W^2$ are each, independently, a group of the Formula Ia:

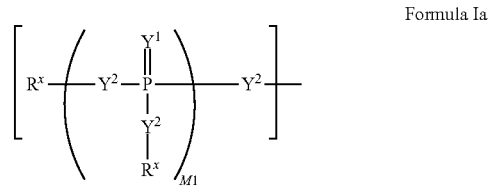

Formula Ia wherein:
each $Y^1$ is, independently, O, S, NR, $^+$N(O)(R), N(OR), $^+$N(O)(OR), or N—$NR_2$;
each $Y^2$ is independently a bond, O, $CR_2$, —O—$CR_2$—, NR, $^+$N(O)(R), N(OR), $^+$N(O)(OR), N—$NR_2$, S, S—S, S(O), or $S(O)_2$;
each $Y^3$ is a single bond;
M1 is 0, 1, 2, or 3;
each $R^x$ is independently $R^y$ or the formula:

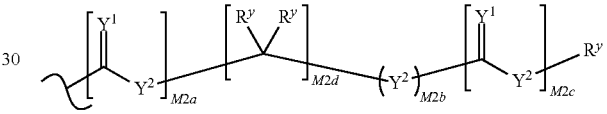

wherein:
each M2a, M2b, and M2c is independently 0 or 1;
M2d is 0, 1, 2, 3, 4, 5, 6, 7, 8, 9, 10, 11 or 12;
each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —$SO_2NR_2$, —CN, —$N_3$, —$NO_2$, —OR, or $W^3$;
or when taken together, two $R^y$ on the same carbon atom form a carbocyclic ring having 3, 4, 5, 6, or 7 carbon ring atoms;
or when taken together, two $R^y$ on the same carbon atom form along with the carbon atom a heterocycle having 3, 4, 5, 6, or 7 ring atoms wherein one ring atom is selected from O or N and all other ring atoms are carbon;
each R is independently H, ($C_1$-$C_8$) alkyl, ($C_1$-$C_8$) substituted alkyl, ($C_2$-$C_8$)alkenyl, ($C_2$-$C_8$) substituted alkenyl, ($C_2$-$C_8$) alkynyl, ($C_2$-$C_8$) substituted alkynyl, $C_6$-$C_{10}$ aryl, $C_6$-$C_{10}$ substituted aryl, a 3- to 10-membered heterocycle, a substituted 3- to 10-membered heterocycle, a 5- to 12-membered heteroaryl, a substituted 5- to 12-membered heteroaryl, arylalkyl, substituted arylalkyl, heteroarylalkyl, or substituted heteroarylalkyl; and
$W^3$ is $W^4$ or $W^5$;
$W^4$ is R, —C($Y^1$)$R^y$, —C($Y^1$)$W^5$, —$SO_2R^y$, or —$SO_2W^5$;
$W^5$ is selected from phenyl, naphthyl, a $C_3$-$C_8$ carbocycle, or a 3- to 10-membered heterocycle, wherein $W^5$ is independently substituted with 0, 1, 2, 3, 4, 5, or 6 $R^y$ groups;
each $R^6$ and $R^7$ is independently H, ($C_1$-$C_8$)alkyl, ($C_2$-$C_8$) alkenyl, ($C_2$-$C_8$)alkynyl, ($C_4$-$C_8$)carbocyclylalkyl, $C_6$-$C_{10}$ aryl, $C_6$-$C_{10}$ substituted aryl, 5- to 10-membered heteroaryl, substituted 5- to 10-membered heteroaryl, —C(=O)($C_1$-$C_8$) alkyl, —S(O)$_n$($C_1$-$C_8$)alkyl or aryl($C_1$-$C_8$)alkyl;

or $R^6$ and $R^7$ taken together with a nitrogen to which they are both attached form a 3- to 7-membered heterocycle wherein any one ring carbon atom of said heterocycle can optionally be replaced with —O— or —S—;

and wherein each ($C_1$-$C_8$)alkyl, ($C_2$-$C_8$)alkenyl, ($C_2$-$C_8$) alkynyl or aryl($C_1$-$C_8$)alkyl of each $R^6$ or $R^7$ is, independently, optionally substituted with one, two, three, or four substituents selected from halo, hydroxy, CN, or $N_3$; and wherein one, two, or three of the non-terminal carbon atoms of each said ($C_1$-$C_8$)alkyl may be optionally replaced with —O— or —S—; or b) $R^4$ is a group selected from:

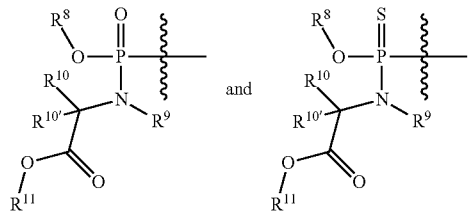

wherein:

$R^8$ is selected from phenyl, 1-naphthyl, 2-naphthyl,

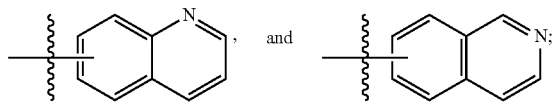

$R^9$ is selected from H and $CH_3$;

$R^{10}$ is selected from H or $C_1$-$C_6$ alkyl;

$R^{10\prime}$ is selected from H or $C_1$-$C_6$ alkyl;

or $R^{10}$ and $R^{10\prime}$, together with the carbon atom to which they are bound, form a 3-, 4-, 5-, or 6-membered spirocycle wherein all ring atoms of the spirocycle are carbon;

or $R^{10}$ and R10', together with the carbon atom to which they are bound, form a 3-, 4-, 5-, or 6-membered spirocycle wherein 1 or 2 of the ring atoms of the spirocycle are selected from the group of O, S, and N, and all other ring atoms of the spirocycle are carbon;

$R^{11}$ is selected from H, $C_1$-$C_8$ alkyl, benzyl, $C_3$-$C_6$ cycloalkyl, —$CH_2$—$C_3$-$C_6$ cycloalkyl, —$CH_2CH_2$—S—C (O)—$C_3$-$C_6$ alkyl,

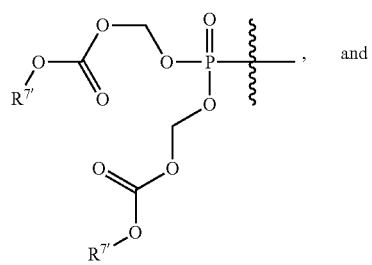

and

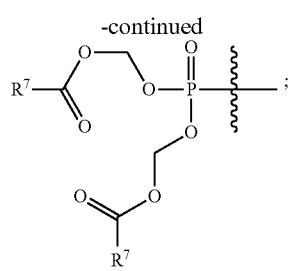

$R^{7\prime}$ is selected from $C_1$-$C_8$ alkyl, —O—$C_1$-$C_8$ alkyl, benzyl, —O-benzyl, —$CH_2$—$C_3$-$C_6$ cycloalkyl, and $CF_3$; or d) $R^4$ and $R^{4\prime}$ combine to form the structure selected from:

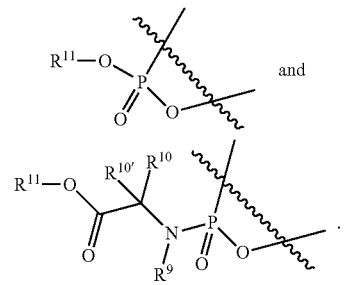

Also provided are two separate embodiments comprising a compound of Formula II, or a pharmaceutically acceptable salt thereof, and a compound of Formula III, or a pharmaceutically acceptable salt thereof:

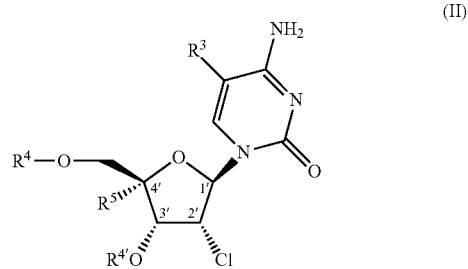

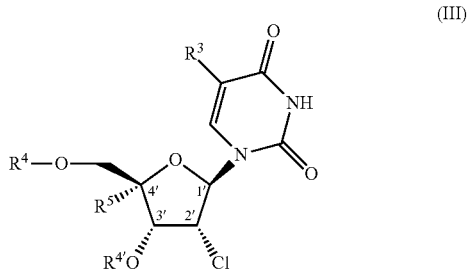

wherein, in each embodiment $R^3$, $R^4$, $R^{4\prime}$, and $R^5$ are as defined for Formula (I), above. Also provided are two separate embodiments comprising a compound of Formula II, or a pharmaceutically acceptable salt thereof, and a compound of Formula III, or a pharmaceutically acceptable salt thereof, wherein, in each embodiment $R^3$, $R^4$, and $R^5$ are as defined for Formula (I), above, and $R^{4\prime}$ is hydrogen.

Also provided are separate embodiments comprising a compound of Formula I, or a pharmaceutically acceptable salt thereof, Formula II, or a pharmaceutically acceptable salt thereof, and Formula III, or a pharmaceutically acceptable salt thereof, wherein in each embodiment $R^5$ is selected from the group of CN, unsubstituted $C_1$-$C_3$ alkyl, $C_1$-$C_3$ alkyl substituted with 1, 2, or 3 halogens selected from F and Cl, $C_1$-$C_3$ alkyl substituted with 1 substituent selected from —S—$CH_3$ and —O—$CH_3$, $C_2$-$C_3$ alkenyl, $C_2$-$C_3$ alkynyl, unsubstituted $C_3$-$C_5$ cycloalkyl, $C_3$-$C_5$ cycloalkyl substituted by 1, 2, or 3 substituents selected from F and $CH_3$; and, when present, $R^a$, $R^1$, $R^2$, $R^3$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments, there is a further embodiment wherein $R^5$ is as just defined, $R^3$ is hydrogen, and, $R^a$, $R^1$, $R^2$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments, there is a further embodiment wherein $R^5$ is as just defined, $R^3$ is F, and, $R^a$, $R^1$, $R^2$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments for a compound of Formula II, or a pharmaceutically acceptable salt thereof, or of Formula III, or a pharmaceutically acceptable salt thereof, there is also a further embodiment wherein $R^{4\prime}$ and $R^5$ are as just defined, and $R^3$ and $R^4$ are each hydrogen. Within each of these embodiments for a compound of Formula II, or a pharmaceutically acceptable salt thereof, or of Formula III, or a pharmaceutically acceptable salt thereof, there is also a further embodiment wherein $R^5$ are as just defined, and $R^3$, $R^4$, and $R^{4\prime}$ are each hydrogen. Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ is F, and $R^4$ is hydrogen. Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ is F, $R^4$ is hydrogen, and $R^{4\prime}$ is hydrogen.

Also provided are separate embodiments comprising a compound of Formula I, or a pharmaceutically acceptable salt thereof, Formula II, or a pharmaceutically acceptable salt thereof, and Formula III, or a pharmaceutically acceptable salt thereof, wherein in each embodiment $R^5$ is selected from the group of CN, unsubstituted $C_1$-$C_3$ alkyl, $C_1$-$C_3$ alkyl substituted with 1, 2, or 3 halogens selected from F and Cl, $C_1$-$C_3$ alkyl substituted with 1 substituent selected from —S—$CH_3$ and —O—$CH_3$, $C_2$-$C_3$ alkenyl, $C_2$-$C_3$ alkynyl, unsubstituted $C_3$-$C_4$cycloalkyl, $C_3$-$C_4$ cycloalkyl substituted by 1, 2, or 3 substituents selected from F and $CH_3$; and, when present, $R^a$, $R^1$, $R^2$, $R^3$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments, there is a further embodiment wherein $R^5$ is as just defined, $R^3$ is hydrogen, and, $R^a$, $R^1$, $R^2$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments, there is a further embodiment wherein $R^5$ is as just defined, $R^3$ is F, and, $R^a$, $R^1$, $R^2$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ and $R^4$ are each hydrogen. Within each of these embodiments for a compound of Formula II, or a pharmaceutically acceptable salt thereof, or of Formula III, or a pharmaceutically acceptable salt thereof, there is also a further embodiment wherein $R^5$ are as just defined, and $R^3$, $R^4$, and $R^{4\prime}0$ are each hydrogen. Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ is F, and $R^4$ is hydrogen. Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ is F, $R^4$ is hydrogen, and $R^{4\prime}$ is hydrogen.

Also provided are separate embodiments comprising a compound of Formula I, or a pharmaceutically acceptable salt thereof, Formula II, or a pharmaceutically acceptable salt thereof, and Formula III, or a pharmaceutically acceptable salt thereof, wherein in each embodiment $R^5$ is selected from the group of CN, unsubstituted $C_1$-$C_3$ alkyl, $C_1$-$C_3$ alkyl substituted with 1, 2, or 3 halogens selected from F and Cl, $C_1$-$C_3$ alkyl substituted with 1 substituent selected from —S—$CH_3$ and —O—$CH_3$, vinyl, ethynyl, unsubstituted cyclopropyl, cyclopropyl substituted by 1 or 2 substituents selected from F and $CH_3$; and, when present, $R^a$, $R^1$, $R^2$, $R^3$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments, there is a further embodiment wherein $R^5$ is as just defined, $R^3$ is hydrogen, and, $R^a$, $R^1$, $R^2$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments, there is a further embodiment wherein $R^5$ is as just defined, $R^3$ is F, and, $R^a$, $R^1$, $R^2$, $R^4$, $R^{4\prime}$, $R^6$, $R^7$, $R^8$, $R^9$, $R^{10}$, $R^{10\prime}$, $R^{11}$, Y, $Y^1$, $Y^2$, $Y^3$, $W^1$, $W^2$, $W^3$, $W^4$, $W^5$, M1, M2a, M2b, M2c, M2d, $R^x$, and $R^y$ are as defined above for Formula (I). Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ and $R^4$ are each hydrogen. Within each of these embodiments for a compound of Formula II, or a pharmaceutically acceptable salt thereof, or of Formula III, or a pharmaceutically acceptable salt thereof, there is also a further embodiment wherein $R^5$ are as just defined, and $R^3$, $R^4$, and $R^{4\prime}$ are each hydrogen. Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ is F, and $R^4$ is hydrogen. Within each of these embodiments for a compound of Formula II, or a pharmaceutically acceptable salt thereof, or of Formula III, or a pharmaceutically acceptable salt thereof, there is also a further embodiment wherein $R^5$ is as just defined, and $R^3$ is F, $R^4$ is hydrogen, and $R^{4\prime}$ is hydrogen.

Also provided are two embodiments comprising, respectively, a compound of Formula (II), or a pharmaceutically acceptable salt thereof, and a compound of Formula (III), or a pharmaceutically acceptable salt thereof, wherein, in each separate embodiment:
$R^3$ is selected from the group of H and F;
$R^5$ is selected from the group of CN, methyl, ethyl, propyl, vinyl, propenyl, ethynyl, $CH_2F$, $CHF_2$, $CH_2Cl$, $CH_2SMe$, —$CH_2OMe$, and cyclopropyl; and
$R^4$ and $R^{4\prime}$ are as defined above for Formula I.

Also provided are two embodiments comprising, respectively, a compound of Formula (II), or a pharmaceutically acceptable salt thereof, and a compound of Formula (III), or a pharmaceutically acceptable salt thereof, wherein, in each separate embodiment:

$R^3$ is selected from the group of H and F;

$R^5$ is selected from the group of CN, methyl, ethyl, propyl, vinyl, propenyl, ethynyl, $CH_2F$, $CHF_2$, $CH_2Cl$, $CH_2SMe$, —$CH_2OMe$, and cyclopropyl;

$R^4$ as defined above for Formula I; and $R^{4t}$ is hydrogen.

Also provided are two embodiments comprising, respectively, a compound of Formula (II), or a pharmaceutically acceptable salt thereof, and a compound of Formula (III), or a pharmaceutically acceptable salt thereof, wherein, in each separate embodiment:

$R^3$ is selected from the group of H and F;

$R^5$ is selected from the group of CN, methyl, ethyl, propyl, vinyl, propenyl, ethynyl, $CH_2F$, $CHF_2$, $CH_2Cl$, $CH_2SMe$, —$CH_2OMe$, and cyclopropyl;

$R^4$ is H; and $R^{4t}$ is hydrogen.

Within each of the groups and embodiments described herein for a compound of Formula I, Formula II, and Formula III, or a pharmaceutically acceptable salt thereof, there is a further embodiment wherein $R^1$, $R^2$, $R^3$, $R^{4t}$, and $R^5$ are as defined for the individual group or embodiment and $R^4$ is selected from:

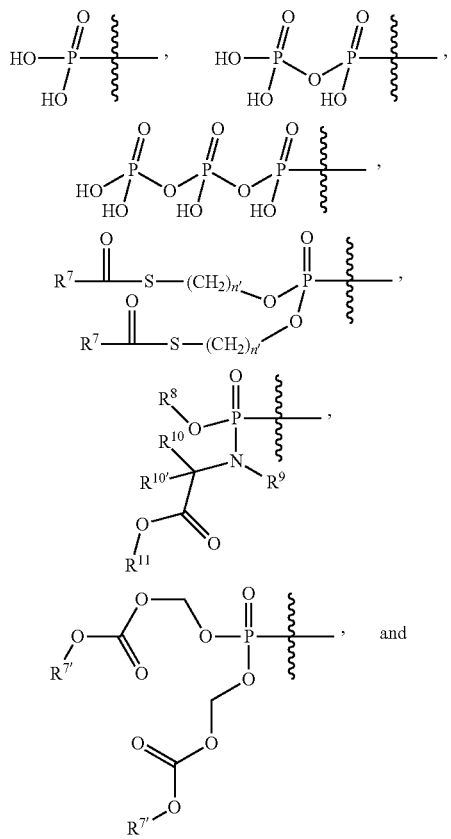

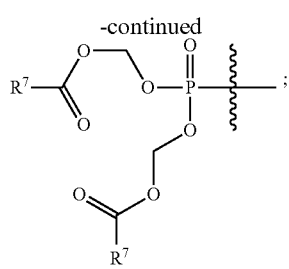

wherein:

n' is selected from 1, 2, 3, and 4;

$R^7$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;

$R^{7'}$ is selected from $C_1$-$C_8$ alkyl, —O—$C_1$-$C_8$ alkyl, benzyl, —O-benzyl, —$CH_2$—$C_3$-$C_6$ cycloalkyl, and $CF_3$;

$R^8$ is selected from phenyl, 1-naphthyl, 2-naphthyl,

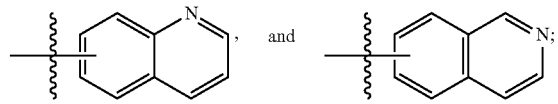

$R^9$ is selected from H and $CH_3$;

$R^{10}$ is selected from H or $C_1$-$C_6$ alkyl;

$R^{10t}$ is selected from H or $C_1$-$C_6$ alkyl;

or $R^{10}$ and $R^{10t}$, together with the carbon atom to which they are bound, form a 3-, 4-, 5-, or 6-membered spirocycle wherein all ring atoms of the spirocycle are carbon;

or $R^{10}$ and $R^{10t}$, together with the carbon atom to which they are bound, form a 3-, 4-, 5-, or 6-membered spirocycle wherein 1 or 2 of the ring atoms of the spirocycle are selected from the group of O, S, and N, and all other ring atoms of the spirocycle are carbon; and $R^{11}$ is selected from H, $C_1$-$C_8$ alkyl, benzyl, $C_3$-$C_6$ cycloalkyl, and —$CH_2$—$C_3$-$C_6$ cycloalkyl.

Within each of the groups and embodiments described herein for a compound of Formula I, Formula II, and Formula III, or a pharmaceutically acceptable salt thereof, there is a further embodiment wherein $R^1$, $R^2$, $R^3$, $R^{4t}$, and $R^5$ are as defined for the individual group or embodiment and $R^4$ is selected from:

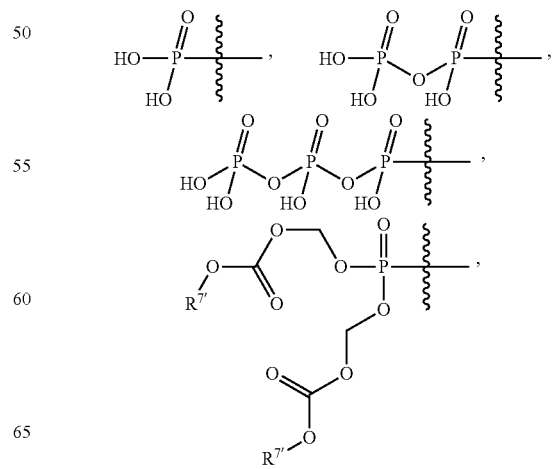

-continued

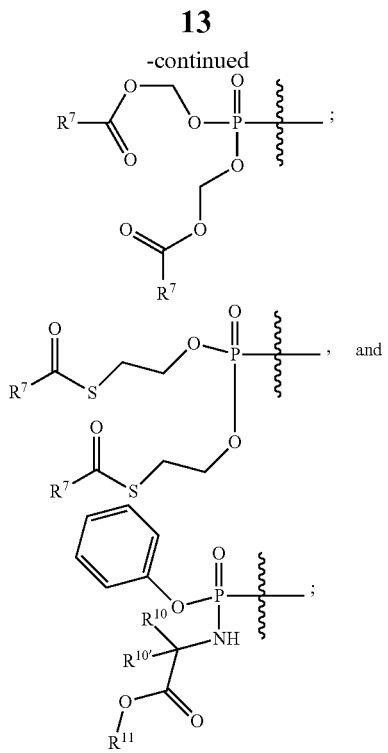

wherein:

$R^7$ is selected from $C_1$-$C_8$ alkyl, —O—$C_1$-$C_8$ alkyl, benzyl, and —$CH_2$—$C_3$-$C_6$ cycloalkyl;

$R^{7'}$ is selected from $C_1$-$C_8$ alkyl, —O—$C_1$-$C_8$ alkyl, benzyl, —O-benzyl, —$CH_2$—$C_3$-$C_6$ cycloalkyl, and $CF_3$;

$R^{10}$ is selected from H or $C_1$-$C_6$ alkyl;

$R^{10'}$ is selected from H or $C_1$-$C_6$ alkyl;

or $R^{10}$ and $R^{10'}$, together with the carbon atom to which they are bound, form a 3-, 4-, 5-, or 6-membered spirocycle wherein all ring atoms of the spirocycle are carbon;

or $R^{10}$ and $R^{10'}$, together with the carbon atom to which they are bound, form a 3-, 4-, 5-, or 6-membered spirocycle wherein 1 or 2 of the ring atoms of the spirocycle are selected from the group of O, S, and N, and all other ring atoms of the spirocycle are carbon; and $R^{11}$ is selected from $C_1$-$C_8$ alkyl, benzyl, $C_3$-$C_6$ cycloalkyl, and —$CH_2$—$C_3$-$C_6$ cycloalkyl.

Also provided are two embodiments comprising, respectively, a compound of Formula (II), or a pharmaceutically acceptable salt thereof, and a compound of Formula (III), or a pharmaceutically acceptable salt thereof, wherein, in each separate embodiment:

$R^3$ is selected from the group of H and F;

$R^{4'}$ is hydrogen;

$R^5$ is selected from the group of CN, methyl, ethyl, propyl, vinyl, propenyl, ethynyl, $CH_2F$, $CHF_2$, $CH_2Cl$, $CH_2SMe$, —$CH_2OMe$, and cyclopropyl; and $R^4$ is selected from the group of:

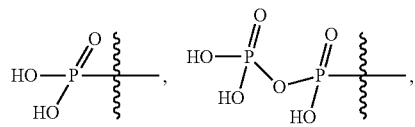

-continued

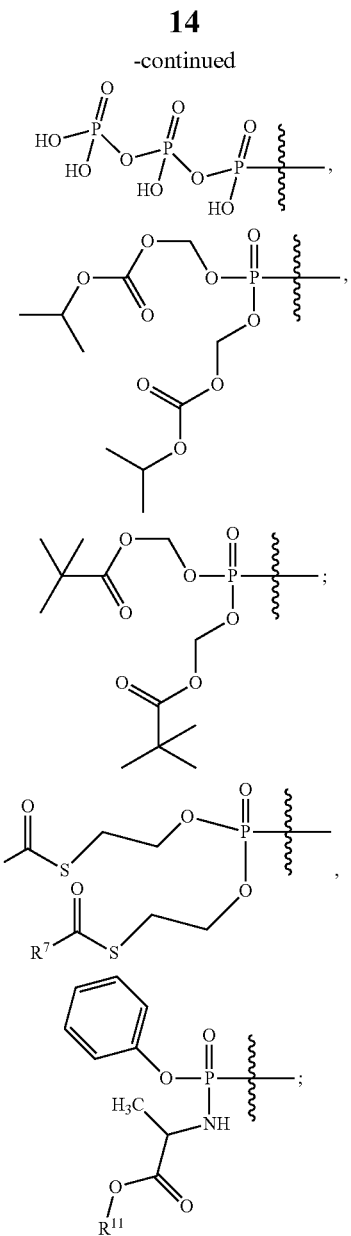

wherein:

$R^7$ is selected from $C_1$-$C_8$ alkyl, —O—$C_1$-$C_8$ alkyl, benzyl, and —$CH_2$—$C_3$-$C_6$ cycloalkyl; and $R^{11}$ is selected from $C_1$-$C_8$ alkyl, benzyl, $C_3$-$C_6$ cycloalkyl, and —$CH_2$—$C_3$-$C_6$ cycloalkyl.

Within each of the groups and embodiments described herein for a compound of Formula I, Formula II, and Formula III, or a pharmaceutically acceptable salt thereof, there is a further embodiment wherein $R^1$, $R^2$, $R^3$, $R^{4'}$, and $R^5$ are as defined for the individual group or embodiment and $R^4$ is selected from:

(a)

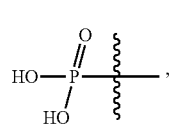

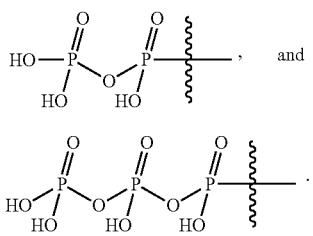

(b)

(c)

Within each of the groups and embodiments described herein for a compound of Formula I, Formula II, and Formula III, or a pharmaceutically acceptable salt thereof, there is a further embodiment wherein $R^1$, $R^2$, $R^3$, $R^{4'}$, and $R^5$ are as defined for the individual group or embodiment and $R^4$ is a group of the formula:

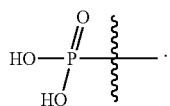

Within each of the groups and embodiments described herein for a compound of Formula I, Formula II, and Formula III, or a pharmaceutically acceptable salt thereof, there is a further embodiment wherein $R^1$, $R^2$, $R^3$, $R^{4'}$, and $R^5$ are as defined for the individual group or embodiment and $R^4$ is a group of the formula:

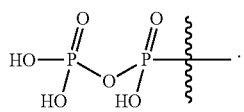

Within each of the groups and embodiments described herein for a compound of Formula I, Formula II, and Formula III, or a pharmaceutically acceptable salt thereof, there is a further embodiment wherein $R^1$, $R^2$, $R^3$, $R^{4'}$, and $R^5$ are as defined for the individual group or embodiment and $R^4$ is a group of the formula:

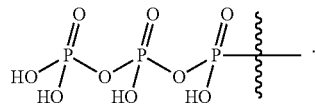

Within each of the groups and embodiments described herein for a compound of Formula I, Formula II, and Formula III, or a pharmaceutically acceptable salt thereof, there is a further embodiment wherein $R^1$, $R^2$, $R^3$, and $R^5$ are as defined for the individual group or embodiment and $R^4$ and $R^{4'}$ combine to form the structure:

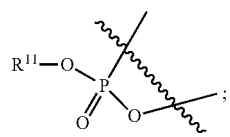

and $R^{11}$ is selected from H, $C_1$-$C_8$ alkyl, benzyl, $C_3$-$C_6$ cycloalkyl, —$CH_2$—$C_3$-$C_6$ cycloalkyl,

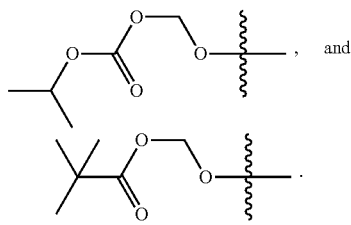

Within each of the groups and embodiments described herein for a compound of Formula I, Formula II, and Formula III, or a pharmaceutically acceptable salt thereof, there is a further embodiment wherein $R^1$, $R^2$, $R^3$, and $R^5$ are as defined for the individual group or embodiment and $R^4$ and $R^{4'}$ combine to form the structure:

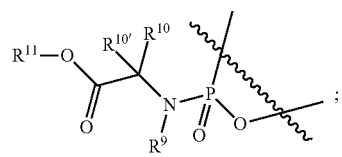

wherein $R^9$ is selected from H and $CH_3$; $R^{10}$ is selected from H or $C_1$-$C_6$ alkyl; $R^{10'}$ is selected from H or $C_1$-$C_6$ alkyl; and $R^{11}$ is selected from H, $C_1$-$C_8$ alkyl, benzyl, $C_3$-$C_6$ cycloalkyl, and —$CH_2$—$C_3$-$C_6$ cycloalkyl.

DETAILED DESCRIPTION

The terms halo and halogen refer to halogen atoms selected from F, Cl, Br, and I. "Azido" refers to an azide group, i.e. the group —$N_3$. The term "n" as used herein refers to an integer selected from 2, 3, 4, 5, 6, 7, 8, 9, 10, 11, 12, 13, 14, 15, 16, 17, 18, 19, and 20.

The term "haloalkyl" as used herein refers to an alkyl as defined herein, wherein one or more hydrogen atoms are each replaced by a halo substituent. For example, a ($C_1$-$C_6$) haloalkyl is a ($C_1$-$C_6$)alkyl wherein one or more of the hydrogen atoms have been replaced by a halo substituent. Such a range includes one halo substituent on the alkyl group t to complete halogenation of the alkyl group.

The term "($C_{1-n}$)haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of ($C_{1-n}$)haloalkyl, wherein n is 2 include, but are not limited to, chloromethyl, chloroethyl, dichloroethyl, bromomethyl, bromoethyl, dibromoethyl, fluoromethyl, difluoromethyl, trifluoromethyl, fluoroethyl and difluoroethyl. Such groups may also be described based on the relevant halogen as "($C_{1-n}$)chloroalkyl", "($C_{1-n}$)bromoalkyl", or "($C_{1-n}$)fluoroalkyl groups".

The term "($C_{1-n}$)alkyl" as used herein, wherein n is an integer, either alone or in combination with another radical, is intended to mean acyclic, straight or branched chain alkyl radicals containing from 1 to n carbon atoms. "($C_{1-8}$)alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl, hexyl, heptyl, and octyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "alkyl" refers to a hydrocarbon containing normal, secondary, or tertiary atoms. For example, an alkyl group can have 1 to 20 carbon atoms (i.e, $(C_1-C_{20})$alkyl), 1 to 10 carbon atoms (i.e., $(C_1-C_{10})$alkyl), 1 to 8 carbon atoms (i.e., $(C_1-C_8)$alkyl) or 1 to 6 carbon atoms (i.e., $(C_1-C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, 1-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., $(C_1-C_{10})$ alkyl), or 1 to 6 carbon atoms (i.e., $(C_1-C_6)$alkyl) or $C_1-C_3$ carbon atoms (i.e., $(C_1-C_3)$alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" is a straight or branched hydrocarbon containing normal, secondary or tertiary carbon atoms with at least one site of unsaturation, i.e. a carbon-carbon, $sp^2$ double bond. For example, an alkenyl group can have 2 to 20 carbon atoms (i.e., $C_2-C_{20}$ alkenyl), 2 to 8 carbon atoms (i.e., $C_2-C_8$ alkenyl), or 2 to 6 carbon atoms (i.e., $C_2-C_6$ alkenyl). Examples of suitable alkenyl groups include, but are not limited to, ethylene or vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$).

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

"Alkynyl" is a straight or branched hydrocarbon containing normal, secondary or tertiary carbon atoms with at least one site of unsaturation, i.e. a carbon-carbon, sp triple bond. For example, an alkynyl group can have 2 to 20 carbon atoms (i.e., $C_2-C_{20}$ alkynyl), 2 to 8 carbon atoms (i.e., $C_2-C_8$ alkyne,), or 2 to 6 carbon atoms (i.e., $C_2-C_6$ alkynyl). Examples of suitable alkynyl groups include, but are not limited to, acetylenic (—C≡CH), propargyl (—$CH_2C$≡CH), and the like.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals in which n is 4 include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryl or carbocycle). Such bicyclic or multicyclic rings may be optionally substituted with one or more (e.g. 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1,2,3,4-tetrahydronaphthyl, anthracenyl, and the like.

Substituents on "substituted alkyl", "substituted alkenyl", and "substituted alkynyl" groups includes those selected from the group of halogens (F, Cl, Br, and I), OH, SH, $NH_2$, NH($C_1-C_6$ alkyl), N($C_1-C_6$ alkyl)$_2$, $NO_2$, CN, —O—$C_1-C_6$ alkyl, and $CF_3$. In one embodiment, for "substituted alkyl" of from either 1 to 6 carbon atoms or 1 to 8 carbon atoms and for "substituted alkenyl" and "substituted alkynyl" groups of from 2 to 6 carbon atoms or from 2 to 8 carbon atoms, each may be substituted by 0, 1, 2, 3, or 4 substituents independently selected from F, Cl, Br, I, OH, SH, $NH_2$, NH($C_1-C_6$ alkyl), N($C_1-C_6$ alkyl)$_2$, $NO_2$, CN, —O—$C_1-C_6$ alkyl, and $CF_3$. In another embodiment, for "substituted alkyl" of from either 1 to 3 carbon atoms or 1 to 4 carbon atoms and for "substituted alkenyl" and "substituted alkynyl" groups of from 2 to 3 carbon atoms or from 2 to 4 carbon atoms, each may be substituted by 0, 1, 2, or 3 substituents independently selected from F, Cl, Br, I, OH, SH, $NH_2$, NH($C_1-C_6$ alkyl), N($C_1-C_6$ alkyl)$_2$, $NO_2$, CN, —O—$C_1-C_6$ alkyl, and $CF_3$.

"Aryl" includes an aromatic hydrocarbon monocyclic or bicyclic ring having from six to 10 ring carbon atoms, including phenyl and naphthyl rings. Substituted aryl groups include an aromatic hydrocarbon monocyclic or bicyclic ring having from six to 10 ring carbon atoms, including phenyl and naphthyl rings, including 1-naphthyl, 2-naphthyl rings, as well as a carbocyclic aromatic monocyclic group containing 6 carbon atoms which may be further fused to a second 5- or 6-membered carbocyclic group which may be aromatic, saturated or unsaturated, including indanyl, indenyl, tetrahydronaphthyl and dihydronaphthyl rings, with .each of the aryl rings being substituted by 0, 1, 2, or 3 substituents independently selected from halogen, —OH, —CN, —NO$_2$, —NH$_2$, —NH(C$_1$-C$_6$ alkyl), —N(C$_1$-C$_6$ alkyl)$_2$, C$_1$-C$_6$ alkyl, C$_1$-C$_6$ alkoxy, and —CF$_3$ "Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl(C$_1$-C$_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "aryl-(C$_{1-n}$)alkyl-" as used herein, wherein n is an integer, either alone or in combination with another radical, is intended to mean an alkyl radical having 1 to n carbon atoms as defined above which is itself substituted with an aryl radical as defined above. Examples of aryl-(C$_{1-n}$)alkyl- include, but are not limited to, phenylmethyl (benzyl), 1-phenylethyl, 2-phenylethyl and phenylpropyl. When an aryl-(C$_{1-n}$)alkyl-group is substituted, it is understood that substituents may be attached to either the aryl or the alkyl portion thereof or both, unless specified otherwise, such that the substitution would give rise to a chemically stable compound, such as are recognized by those skilled in the art.

Examples of "arylalkyl" used herein refer to a moiety of the formula —(CH$_2$)$_q$—Y, wherein q is an integer selected independently in each instance from 1, 2, 3, 4, 5, or 6, and "Y" is a phenyl or naphthyl ring, each substituted by 0, 1, 2, or 3 substituents independently selected from halogen, —OH, —CN, —NO$_2$, —NH$_2$, —NH(C$_1$-C$_6$ alkyl), —N(C$_1$-C$_6$ alkyl)$_2$, C$_1$-C$_6$ alkyl, C$_1$-C$_6$ alkoxy, and —CF$_3$.

The terms "heterocycle" and "heterocyclic" are synonymous and refers to monocyclic and fused bicyclic, saturated or partially unsaturated rings having, unless otherwise indicated, 3, 4, 5, 6, 7, 8, 9, or 10 ring atoms wherein 1, 2, 3, or 4 ring atoms is/are a heteroatom independently selected from N, O and S and all remaining ring atoms are C. In one embodiment, the heterocyclic group has 5, 6, 9 or 10 rings atoms wherein 1, 2 or 3 ring atoms is/are a heteroatom independently selected from N, O and S. In all embodiments wherein the heterocyclic group includes 2 or more heteroatoms (N, O and S) the heteroatoms may be the same or different. In all embodiments wherein the compound of Formula I includes 2 or more heterocyclic groups, the heterocyclic groups may be the same or different. Examples of heterocyclic groups include but are not limited to oxiranyl, azetidinyl, oxetanyl, thietanyl, furanyl, tetrahydrofuranyl, thiophenyl, tetrahydrothiophenyl, sulfur oxidized tetrahydrothiophenyl, pyrrolyl, pyrrolinyl, pyrrolidinyl, dioxolanyl, oxazolidinyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, tetrazolyl, pyranyl, dihydropyranyl, tetrahydropyranyl, pyridyl, dihydropyridyl, piperidyl, dioxanyl, morpholinyl, dithianyl, thiomorpholinyl, pyridazinyl, pyrimidinyl, pyrazinyl, piperazinyl, triazinyl, indolizinyl, indolyl, isoindolyl, oxindolyl, indolinyl, benzofuranyl, dihydrobenzofuranyl, isobenzofuranyl, benzothienyl, indazolyl, benzimidazolyl, benzoxazolinyl, benzoxazolyl, benzisoxazolyl, benzthiazolyl, benzotriazolyl, benzopyranyl, purinyl, quinolizinyl, quinolinyl, isoquinolinyl, tetrahydroquinolinyl, tetrahydroisoquinolinyl, decahydroquinolinyl, octahydroisoquinolinyl, cinnolinyl, phthalazinyl, quinazolinyl, quinoxalinyl, naphthyridinyl, pteridinyl, thianaphthalenyl and the like. Heterocyclic groups may be bound through any available ring carbon or ring heteroatom, such as N. Each "Heterocyclic group", "heterocyclic ring" or "heterocycle" may be substituted by 0, 1, 2, or 3 substituents independently selected from halogen, —OH, —CN, —NO$_2$, —NH$_2$, —NH(C$_1$-C$_6$ alkyl), —N(C$_1$-C$_6$ alkyl)$_2$, C$_1$-C$_6$ alkyl, C$_1$-C$_6$ alkoxy, and —CF$_3$.

The term cycloalkyl refers to a cyclic aliphatic group. The cycloallkyl groups herein may be referenced by the number of carbon atoms in their ring, such as "C$_3$-C$_4$ cycloalkyl" referring to a cycloalkyl ring with 3 or 4 carbon ring atoms or "C$_3$-C$_6$ cycloalkyl" indicating a cycloalkyl ring with 3, 4, 5, or 6 carbon ring atoms, i.e. a cyclopropyl, cyclobutyl, cyclopentyl, or cyclohexyl ring.

The term "carbocycle" or "carbocyclyl" refers to a saturated (i.e., cycloalkyl) or partially unsaturated (e.g., cycloalkenyl, cycloalkadienyl, etc.) ring having 3 to 8 carbon atoms as a monocycle or a mutlicyclic ring system. In one embodiment the carbocycle is a monocycle comprising 3-6 ring carbons (i.e. (C$_3$-C$_6$)carbocycle). Carbocycle includes multicyclic carbocyles having 7 to 12 carbon atoms as a bicycle, and up to about 20 carbon atoms as a polycycle provided that the largest single ring of a multicyclic carbocycle is 7 carbon atoms. The term "spiro-bicyclic carbocycle" refers to a carbocycle bicyclic ring system wherein the rings of the bicyclic ring system are connected to a single carbon atom (e.g. spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane). The term "bridged-bicyclic carbocycle" refers to a carbocycle bicyclic ring system wherein the rings of the bicyclic ring system are connected to two non-adjacent carbon (e.g. norbornane, bicyclo[2.2.2]octane, etc). The "carbocycle" or "carbocyclyl" may be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexa-1,3-dienyl, cycloheptanyl, cycloheptenyl, cyclohepta-1,3-dienyl, cyclohepta-1,4-dienyl, cyclooctyl, and cyclooctenyl rings.

Each carbocyclyl group may be substituted by 0, 1, 2, or 3 substituents independently selected from halogen, —OH, —CN, —NO$_2$, —NH$_2$, —NH(C$_1$-C$_6$ alkyl), —N(C$_1$-C$_6$ alkyl)$_2$, C$_1$-C$_6$ alkyl, C$_1$-C$_6$ alkoxy, and —CF$_3$.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

Each heteroaryl group may be substituted by 0, 1, 2, or 3 substituents independently selected from halogen, —OH, —CN, —NO$_2$, —NH$_2$, —NH(C$_1$-C$_6$ alkyl), —N(C$_1$-C$_6$ alkyl)$_2$, C$_1$-C$_6$ alkyl, C$_1$-C$_6$ alkoxy, and —CF$_3$.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl(C$_1$-C$_6$)alkyl). Heteroarylalkyl groups include, but are not limited to heteroaryl-CH$_2$—, heteroaryl-CH(CH$_3$)—, heteroaryl-CH$_2$CH$_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

The heteroaryl ring of each of is the heteroarylalkyl group may be substituted by 0, 1, 2, or 3 substituents independently selected from halogen, —OH, —CN, —NO$_2$, —NH$_2$, —NH(C$_1$-C$_6$ alkyl), —N(C$_1$-C$_6$ alkyl)$_2$, C$_1$-C$_6$ alkyl, C$_1$-C$_6$ alkoxy, and —CF$_3$.

Pharmaceutical Formulations

Also provided herein is a pharmaceutical formulation comprising a pharmaceutically effective amount of a compound of Formula (I) or a pharmaceutically acceptable salt, solvate, and/or ester thereof, and a pharmaceutically acceptable carrier or excipient. Also provided are separate pharmaceutical formulations, each comprising a pharmaceutically effective amount of a compound of Formula (II), Formula (III), or a specific compounds of the examples herein, or a pharmaceutically acceptable salt, solvate, and/or ester thereof, and a pharmaceutically acceptable carrier or excipient.

The compounds herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include Tween® 60, Span® 80, cetostearyl alcohol, benzyl alcohol, myristyl alcohol, glyceryl monostearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations herein comprise a combination together with one or more pharmaceutically acceptable carriers or excipients and optionally other therapeutic agents.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylceluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. This suspension may be formulated according to the known art using those suitable dispersing or wetting agents and suspending agents which have been mentioned above. The sterile injectable or intravenous preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumovirinae infections as described below.

Another embodiment provides a novel, efficacious, safe, nonirritating and physiologically compatible inhalable composition comprising a compound of Formulas I-III, or a pharmaceutically acceptable salt thereof, suitable for treating Pneumovirinae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 μm. Preferably, the compound of Formulas I-III is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, J. *Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 μm and about 5 μm using a nebulizer able to aerosolize the formulation of the compound of Formulas I-III into particles of the required MMAD. To be optimally therapeutically effective and to avoid upper respiratory and systemic side effects, the majority of aerosolized particles should not have a MMAD greater than about 5 μm. If an aerosol contains a large number of particles with a MMAD larger than 5 μm, the particles are deposited in the upper airways decreasing the amount of drug delivered to the site of inflammation and bronchoconstriction in the lower respiratory tract. If the MMAD of the aerosol is smaller than about 1 μm, then the particles have a tendency to remain suspended in the inhaled air and are subsequently exhaled during expiration.

When formulated and delivered according to the method herein, the aerosol formulation for nebulization delivers a therapeutically efficacious dose of the compound of Formulas I-III to the site of Pneumovirinae infection sufficient to treat the Pneumovirinae infection. The amount of drug administered must be adjusted to reflect the efficiency of the delivery of a therapeutically efficacious dose of the compound of Formulas I-III. In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formulas I-III into the airways. In a preferred embodiment, at least about 30 to about 50% of the active compound is delivered. More preferably, about 70 to about 90% of the active compound is delivered.

In another embodiment, a compound of Formulas I-III or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formulas I-III is processed into particles with, predominantly, MMAD between about 1 μm and about 5 μm by milling spray drying, critical fluid processing, or precipitation from solution. Media milling, jet milling, and spray-drying devices and procedures capable of producing the particle sizes with a MMAD between about 1 μm and about 5 μm are well known in the art. In one embodiment, excipients are added to the compound of Formulas I-III before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formulas I-III is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formulas I-III, or a pharmaceutically acceptable salt thereof, is delivered as a dry powder using either type of dry powder inhaler as described herein, wherein the MMAD of the dry powder, exclusive of any excipients, is predominantly in the range of 1 µm to about 5 µm.

In another embodiment, a compound of Formulas I-III is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In preferred embodiments, a compound of Formulas I-III, or a pharmaceutically acceptable salt thereof, is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more of the compounds (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds herein is that they are orally bioavailable and can be dosed orally.

Combination Therapy

Compositions are also used in combination with other active ingredients. For the treatment of Pneumovirinae virus infections, preferably, the other active therapeutic agent is active against Pneumovirinae virus infections, particularly respiratory syncytial virus infections. Non-limiting examples of these other active therapeutic agents are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof.

Many of the infections of the Pneumovirinae viruses are respiratory infections. Therefore, additional active therapeutics used to treat respiratory symptoms and sequelae of infection may be used in combination with the compounds of Formulas I-III. The additional agents are preferably administered orally or by direct inhalation. For example, other preferred additional therapeutic agents in combination with the compounds of Formulas I-III for the treatment of viral respiratory infections include, but are not limited to, bronchodilators and corticosteroids.

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds of Formulas I-III are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diprorionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salts thereof.

Other anti-inflammatory agents working through anti-inflammatory cascade mechanisms are also useful as additional therapeutic agents in combination with the compounds of Formulas I-III for the treatment of viral respiratory infections. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Combinations comprising inhaled β2-adrenoreceptor agonist bronchodilators such as formoterol, albuterol or salmeterol with the compounds of Formulas I-III are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds of Formulas I-III are also suitable, but non-limiting, combinations useful for the treatment of respiratory viral infections.

For the treatment or prophylaxis of pulmonary bronchoconstriction, anticholinergics are of potential use and, therefore, useful as an additional therapeutic agents in combination with the compounds of Formulas I-III for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-dithiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)piperidin-4-yl ester.

The compounds of Formulas I-III may also be combined with mucolytic agents to treat both the infection and symptoms of respiratory infections. A non-limiting example of a mucolytic agent is ambroxol. Similarly, the compounds of Formulas I-III may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, J. Pediatrics 2007, 266). The compounds of Formulas I-III may also be combined with nebulized hypertonic saline particularly when the Pneumovirinae virus infection is complicated with bronchiolitis. The combination of the compounds of Formulas I-III with hypertonic saline may also comprise any of the additional agents discussed above. In one embodiment, nebulized about 3% hypertonic saline is used.

It is also possible to combine any compound with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound herein with one or more other active therapeutic agents generally refers to simultaneous or sequential administration of a compound and one or more other active therapeutic agents, such that therapeutically effective amounts of the compound and one or more other active therapeutic agents are both present in the body of the patient.

Co-administration includes administration of unit dosages of the compounds before or after administration of unit dosages of one or more other active therapeutic agents, for example, administration of the compounds within seconds, minutes, or hours of the administration of one or more other active therapeutic agents. For example, a unit dose of a compound can be administered first, followed within seconds or minutes by administration of a unit dose of one or more other active therapeutic agents. Alternatively, a unit dose of one or more other therapeutic agents can be administered first, followed by administration of a unit dose of a compound within seconds or minutes. In some cases, it may be desirable to administer a unit dose of a compound first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound herein.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides a method of treating Pneumovirinae virus infection in a human, the method comprising administering to the human a therapeutically effective amount of a compound of Formula (I), or a pharmaceutically acceptable salt, solvate, and/or ester thereof. Also provided are separate methods of treating Pneumovirinae virus infection in a human, each comprising administering to the human a therapeutically effective a pharmaceutically effective amount of a compound of Formula (II), Formula (III), or one of the specific compounds of the examples herein, or a pharmaceutically acceptable salt, solvate, and/or ester thereof, and a pharmaceutically acceptable carrier or excipient.

In another embodiment, provided is a method of treating a Pneumovirinae infection in a human by administering to the human a therapeutically effective amount of a racemate, enantiomer, diastereomer, tautomer, polymorph, pseudopolymorph, amorphous form, hydrate or solvate of a compound of a compound of Formula (I), or a pharmaceutically acceptable salt or ester thereof.

Further provided are separate methods of treating a Pneumovirinae infection in a human in need thereof, each method comprising administering to the human a therapeutically effective amount of a racemate, enantiomer, diastereomer, tautomer, polymorph, pseudopolymorph, amorphous form, hydrate or solvate of a compound of Formula (II), Formula (III), or one of the specific compounds of the examples herein, or a pharmaceutically acceptable salt, solvate, and/or ester thereof.

In still yet another embodiment, the present application provides for a method of treating human respiratory syncytial virus infection in a human, the method comprising administering to the human a therapeutically effective amount of a compound of Formula (I), or a pharmaceutically acceptable salt, solvate, and/or ester thereof.

In still yet another embodiment, the present application provides for a method of treating human respiratory syncytial virus infection in a human, the method comprising administering to the human a therapeutically effective amount of a compound of Formula (I), or a pharmaceutically acceptable salt, solvate, and/or ester thereof, and at least one additional active therapeutic agent.

Further provided are separate methods of treating a human respiratory syncytial virus infection in a human in need thereof, each method comprising administering to the human a therapeutically effective amount of a compound of Formula (II), Formula (III), or one of the specific compounds of the examples herein, or a pharmaceutically acceptable salt, solvate, and/or ester thereof.

Also provided are separate methods of treating a human respiratory syncytial virus infection in a human in need thereof, each method comprising administering to the human a therapeutically effective amount of a compound of Formula (II), Formula (III), or one of the specific compounds of the examples herein, or a pharmaceutically acceptable salt, solvate, and/or ester thereof, and at least one additional active therapeutic agent.

Also provided are separate methods of treating a human respiratory syncytial virus infection in a human in need thereof, wherein the human is also experiencing bronchiolitis, each method comprising administering to the human a therapeutically effective amount of a compound of Formula (I), Formula (II), or one of the specific compounds of the examples herein, or a pharmaceutically acceptable salt, solvate, and/or ester thereof.

Also provided are separate methods of treating a human respiratory syncytial virus infection in a human in need thereof, wherein the human is also experiencing pneumonia, each method comprising administering to the human a therapeutically effective amount of a compound of Formula (I), Formula (II), or one of the specific compounds of the examples herein, or a pharmaceutically acceptable salt, solvate, and/or ester thereof.

Also provided are separate methods of improving respiratory symptoms in a human experiencing a human respiratory syncytial virus infection, each method comprising administering to the human a therapeutically effective amount of a compound of Formula (I), Formula (II), or one of the specific compounds of the examples herein, or a pharmaceutically acceptable salt, solvate, and/or ester thereof.

Respiratory symptoms in a human experiencing a respiratory syncytial virus infection may include congested or runny nose, coughing, wheezing, sneezing, rapid breathing or difficulty breathing, apnea, bronchiolitis, and pneumonia.

Also provided is an embodiment comprising the use of a compound of Formula (I), or a pharmaceutically acceptable salt, solvate, and/or ester thereof, for the manufacture of a medicament for the treatment of a Pneumovirinae virus infection or a respiratory syncytial virus infection in a human.

Also provided is an embodiment comprising the use of a compound of Formula (II), Formula (III), one of the specific compounds of the examples herein, or a pharmaceutically acceptable salt, solvate, and/or ester thereof, for the manufacture of a medicament for the treatment of a Pneumovirinae virus infection or a respiratory syncytial virus infection in a human.

Also provided is a pharmaceutical formulation comprising a pharmaceutically effective amount of a compound of Formula (I), or a pharmaceutically acceptable salt, solvate, and/or ester thereof, and a pharmaceutically acceptable carrier or excipient. Further provided is a pharmaceutical formulation comprising a pharmaceutically effective amount of a compound of Formula (II), Formula (III), or one of the specific compounds of the examples herein, or a pharmaceutically acceptable salt, solvate, and/or ester thereof, and a pharmaceutically acceptable carrier or excipient.

Also provided is a pharmaceutical formulation comprising a pharmaceutically effective amount of a compound of Formula (I), or a pharmaceutically acceptable salt, solvate, and/or ester thereof, and a pharmaceutically acceptable carrier or excipient and a pharmaceutically effective amount of at least one additional active therapeutic agent. Further provided is a pharmaceutical formulation comprising a pharmaceutically effective amount of a compound of Formula (II), Formula (III), or one of the specific compounds of the examples herein, or a pharmaceutically acceptable salt, solvate, and/or ester thereof, and a pharmaceutically acceptable carrier or excipient and a pharmaceutically effective amount of at least one additional active therapeutic agent.

Also provided are separate embodiments comprising a compound of Formula (I), Formula (II), Formula (III), or one of the specific compounds of the examples herein, or a pharmaceutically acceptable salt, solvate, and/or ester thereof, for use in the treatment of a Pneumovirinae virus infection or a respiratory syncytial virus infection in a human.

Also provided are separate embodiments comprising a compound of Formula (I), Formula (II), Formula (III), or one of the specific compounds of the examples herein, or a pharmaceutically acceptable salt, solvate, and/or ester thereof, for use as a medicament.

Also provided are separate embodiments comprising a method for manufacturing a medicament intended for treatment of a Pneumovirinae virus infection or a respiratory syncytial virus infection in a human, characterised in that a compound of Formula (I), Formula (II), Formula (III), or one of the specific compounds of the examples herein, or a pharmaceutically acceptable salt, solvate, and/or ester thereof, is used.

Also provided is a compound of Formula (I), or a pharmaceutically acceptable salt, solvate, and/or ester thereof, for the treatment of a Pneumovirinae virus infection or a respiratory syncytial virus infection in a human.

Also provided are separate embodiments comprising that a compound of Formula (II), Formula (III), or one of the specific compounds of the examples herein, or a pharmaceutically acceptable salt, solvate, and/or ester thereof, for the treatment of a Pneumovirinae virus infection or a respiratory syncytial virus infection in a human.

Further provided is a compound as described in this specification. Also provided is a pharmaceutical composition as described in this specification. Also provided is a method of using a compound of Formula (I), as described in this specification. Further provided is a method of making a compound of Formula (I), as described in this specification.

In still yet another embodiment, the present application provides a compound of Formula (I), or a pharmaceutically acceptable salt, solvate, and/or ester thereof, and at least one additional active therapeutic agent for use in a method of treating human respiratory syncytial virus infection in a human.

In still yet another embodiment, the present application provides a compound of Formula (I), or a pharmaceutically acceptable salt, solvate, and/or ester thereof, for use in a method of treating human respiratory syncytial virus infection in a human, wherein the method comprises administering a compound of Formula (I), or a pharmaceutically acceptable salt, solvate, and/or ester thereof, and at least one additional active therapeutic agent, to the human.

Also provided are separate embodiments comprising a compound of Formula (II), Formula (III), or one of the specific compounds of the examples herein, or a pharmaceutically acceptable salt, solvate, and/or ester thereof, and at least one additional active therapeutic agent for use in a method of treating a human respiratory syncytial virus infection in a human.

Also provided are separate embodiments comprising a compound of Formula (II), Formula (III), or one of the specific compounds of the examples herein, or a pharmaceutically acceptable salt, solvate, and/or ester thereof, for use in a method of treating human respiratory syncytial virus infection in a human, wherein the method comprises administering a compound of Formula (II), Formula (III), or one of the specific compounds of the examples herein, or a pharmaceutically acceptable salt, solvate, and/or ester thereof, and at least one additional active therapeutic agent, to the human.

Also provided are separate embodiments comprising a compound of Formula (I), Formula (II), Formula (III), or one of the specific compounds of the examples herein, or a pharmaceutically acceptable salt, solvate, and/or ester thereof for use in a method of treating a human respiratory syncytial virus infection in a human in need thereof, wherein the human is also experiencing bronchiolitis.

Also provided are separate embodiments comprising a compound of Formula (I), Formula (II), Formula (III), or one of the specific compounds of the examples herein, or a pharmaceutically acceptable salt, solvate, and/or ester thereof for use in a method of treating a human respiratory syncytial virus infection in a human in need thereof, wherein the human is also experiencing pneumonia.

Also provided are separate embodiments comprising a compound of Formula (I), Formula (II), Formula (III), or one of the specific compounds of the examples herein, or a pharmaceutically acceptable salt, solvate, and/or ester thereof for use in a method of improving respiratory symptoms in a human experiencing a human respiratory syncytial virus infection.

Also provided is a product comprising a compound of Formula (I), Formula (II), Formula (III), or one of the specific compounds of the examples herein, or a pharmaceutically acceptable salt, solvate, and/or ester thereof, as a combined preparation for simultaneous, separate, or sequential use in treating a human respiratory syncytial virus infection in a human or a Pneumovirinae virus infection in a human.

Metabolites of the Compounds

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g. $^{14}$C or $^{3}$H) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds even if they possess no RSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

Useful oxygen protecting groups include a silyl ether protecting group or a benzyl-type protecting group, including methoxybenzyl groups.

Useful silyl ether protecting groups include Trimethylsilyl (TMS), Triethylsilyl (TES), Dimethylisopropylsilyl (IPDMS), Diethylisopropylsilyl (DEIPS), Dimethylthexylsilyl (TDS), t-Butyldimethylsilyl (TBS or TBDMS), t-Butyldiphenylsilyl (TBDPS), Tribenzylsilyl, Tri-p-xylylxilyl, Triisopropylsilyl (TIPS), Diphenylmethylsilyl (DPMS), Di-t-butylmethylsilyl (DTBMS), Triphenylsilyl (TPS), Methyldiphenylsilyl (MDPS), t-butylmethoxyphenylsilyl, Tris(trimethylsilyl)silyl (sisyl), (2-Hydroxystyryl)dimethylsilyl (HSDMS), (2-Hydroxystyryl)diisopropylsilyl (HS-DIS). t-Butylmethoxyphenylsilyl (TBMPS), and t-Butoxydiphenylsilyl (DPTBOS) protecting groups.

Useful benzyl-type protecting groups include benzyl, halogenated benzyl, p-methoxybenzyl, benzyloxymethyl, 2,4-dimethoxybenzyl, 3,4-dimethoxybenzyl, 2,6-dimethoxybenzyl, p-CF$_3$-benzyl, p-methylbenzyl, p-methoxylbenzyl, 3,5-dimethylbenzyl, p-tert-butylbenzyl, o-nitrobenzyl, p-nitrobenzyl, p-halobenzyl, including p-Br-benzyl, 2,6-dichlorobenzyl, p-cyanobenzyl, p-phenylbenzyl, 2,6-difluorobenzyl, p-acylaminobenzyl (PAB), p-azidobenzyl (Azb), 4-azido-3-chlorobenzyl, 2-trifluoromethylbenzyl, p-(methylsulfinyl)benzyl, 2-picolyl, 4-picolyl, 3-methyl-2-picolyl N-oxido, 2-quinolinylmethyl, diphenylmethyl (DPM), p,p'-dinitrobenzhydryl, triphenylmethyl, alpha-naphthyldiphenylmethyl, p-methoxyphenyldiphenylmethyl, di(p-methoxyphenyl)phenylmethyl, tri(p-methoxyphenyl)methyl, 4,4',4"-tris(benzoyloxyphenyl)methyl, and 2-naphthylmethyl protecting groups.

Useful amine protecting groups include p-methoxybenzyl carbonyl (Moz or MeOZ), acetyl (Ac), benzoyl (Bz), p-methoxybenzyl (PMB), 3,4-dimethoxybenzyl (DMPM), p-methoxyphenyl (PMP), tosyl (Ts or Tos), trifluoroacetamide, and trityl protecting groups.

Useful amine protecting groups also include carbamate and amide protecting groups. Examples of carbamate protecting groups include methyl and ethyl carbamates such as 9-fluorenylmethyloxycarbonyl (FMOC), 9-(2-sulfo)fluorenylmethyl, 9-(2,7-dibromo)fluorenylmethyl, 17-tetrabenzo[a,c,g,i]fluorenylmethyl (Tbfmoc), 2-chloro-3-indenylmethyl (Climoc), benz[f]inden-3-ylmethyl (Bimoc), 2,7-di-t-butyl[9-(10,10-dioxo-10,10,10,10-tetrahydrothioxanyl)]methyl (DBD-Tmoc), [2-(1,3-dithianyl)methyl (Dmoc), and 1,1-dioxobenzo[b]thiophene-2-ylmethyl (Bsmoc) carbamates.

Examples of useful substituted ethyl carbamates include 1,1-dimethyl-2-cyanoethyl, 2-phosphonioethyl (Peoc), 2-methylthioethyl, 2-(p-toluenesulfonyl)ethyl, 2,2,2,-trichloroethyl (Troc), 2-(trimethylsilyl)ethyl (Teoc), 2-phenylethyl (hZ), 1-(1-adamantyl)-1-methylethyl (Adpoc), 1,1-dimethyl-2-bromoethyl, 1,1-dimethyl-2-chloroethyl, 1,1-dimethyl-2,2-dibromoethyl (DB-t-BOC), 1,1-dimethyl-2,2,2-trichloroethyl (TCBOC), 1-methyl-1-(4-biphenylyl)ethyl (Bpoc), 1-(3,5-di-t-butylphenyl)-1-methylethyl (t-Bumeoc), 2-(2'pyridyl)ethyl, 2-(4'pyridyl)ethyl, 2,2-bis(4'-nitrophenyl)ethyl (Bnpeoc), N-(2-pivaloylamino)-1,1, dimethylethyl, 2-[(2-nitrophenyl)dithio]-1-phenylethyl (NpSSPeoc), 2-(N,N-dicyclohexylcarboxamido)ethyl, t-butyl (Boc or BOC), 1-adamantyl (1-Adoc), 2-adamantyl (2-Adoc), vinyl (Voc), allyl (Aloc or alloc), 1-isopropylallyl (Ipaoc), cinnamyl (Coc), 4-nitrocinnamyl (Noc), 3-(3'-pyridyl)prop-2-enyl (Paloc), 8-quinolyl, and N-hydroxypiperidinyl, carbamates, as well as alkyldithio carbamates, including methyldithio, ethyldithio, isopropyldithio, t-butyldithio, and phenyldithio carbamates.

Also useful are aryl-containing and substituted aryl-containing carbamates such as benzyl, p-methoxybenzyl, p-nitrobenzyl, p-bromobenzyl, p-chlorobenzyl, 2,4-dichlorobenzyl, 4-methylsulfinylbenzyl (Msz), 9-anthrylmethyl, 4-methylthiophenyl (Mtpc), 1-methyl-1-(triphenylphosphonio)ethyl (2-triphenylphosphonioisopropyl) (Ppoc), 2-dansylethyl (Dnseoc), 2-(4-nitrophenyl)ethyl (Npeoc), 4-phenylacetoxybenzyl (PhAcOZ), 4-azidobenzyl (ACBZ), 4-azidomethoxybenzyl, m-chloro-p-acyloxybenzyl, p-(dihydroxyboryl)benzyl, carbobenzyloxy (Cbz), 4-benzisoxazolylmethyl (Bic), 2-(trifluoromethyl)-6-chromonylmethyl (Tcroc), phenyl, and diphenylmethyl carbamates. Additional carbamates include butynyl, cyclopentyl, cyclohexyl, cyclopropylmethyl, 1-methylcyclobutyl, 1-methylcyclohexyl, 1,1-dimethylpropynyl, and 1-methyl-1-cyclopropylmethyl carbamates.

Useful amide protecting groups for amines include N-formyl, N-acetyl, N-chloroacetyl, N-trichloroacetyl, N-trifluoroacetyl (TFA), N-phenylacetyl, N-3-phenylpropionyl, N-4-pentenoyl, N-picolinoyl, N-3-pyridylcarboxamido, N-benzoylphenylalanyl, N-benzoyl, and N-p-phenylbenzoyl amides.

TABLE 1

List of abbreviations and acronyms.

| Abbreviation | Meaning |
|---|---|
| Ac | acetate |
| Ac₂O | acetic anhydride |
| AcOH | acetic acid |
| ACN | acetonitrile |
| Bn | benzyl |
| BOM | benzyl chloromethyl ether |
| Bu | butyl |
| Bz | benzoyl |
| BzCl | benzoyl chloride |
| CAN | ceric ammonium nitrate |
| CDI | 1,1'-carbonyldiimidazole |
| DAST | diethylaminosulfur trifluoride |
| DBU | 1,8-diazabicyclo[5.4.0]undec-7-ene |
| DIPEA | N,N-diisopropylethylamine |
| DCM | dichloromethane |
| DMAP | 4-dimethylamiopyridine |
| DMDO | dimethydioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCl | N-(3-dimethylaminopropyl)-N'-ethylcarbodiimide hydrochloride |
| Et | ethyl |
| EtOAc | ethyl acetate |
| hr | hour |
| Imid | imidazole |
| tBuOK | potassium tert-butoxide |
| Me | methyl |
| MeOH | methyl alcohol |
| min | minute |
| MMTr | 4-methoxytriphenylmethane |
| MMTrCl | 4-methoxytriphenylchloromethane |
| NBS | N-bromosuccinimide |
| NMP | 1-methyl-2-pyrrolidinone |
| Ph | phenyl |
| Ph₃P | triphenylphosphine |
| PMB | para-methoxybenzyl |
| PMBCl | para-methoxybenzyl chloride |
| pTSA | para-toluenesulfonic acid |
| Pyr | pyridine |
| RT | room temperature |
| TBAF | tetrabutylammonium flouride |
| TBS | tert-butyldimethylsilyl |
| TBSCl | tert-Butyldimethylsilyl chloride |
| TEA | triethylamine |
| TFA | trifluoroacetic acid |
| Tf₂O | trifluoromethanesulfonic anhydride |
| THF | tetrahydrofuran |
| TMS | trimethylsilyl |
| TMSCl | trimethylsilyl chloride |
| TPSCl | 2,4,6-triisopropylbenzenesulfonyl chloride |

Species (Nucleosides)

Provided are the individual nucleoside compounds below, or a pharmaceutically acceptable salt thereof.

8

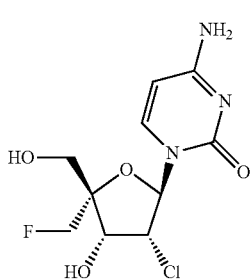

9

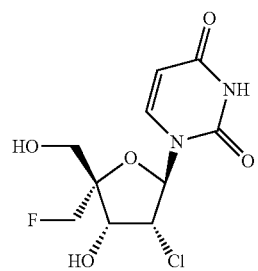

11

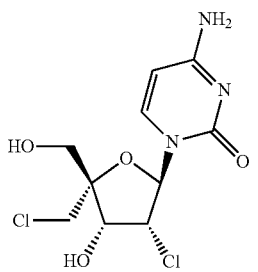

12

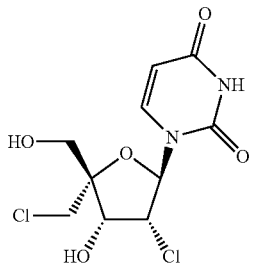

14

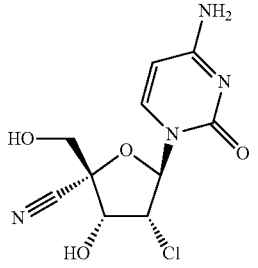

15

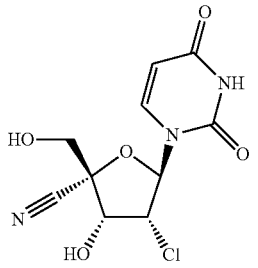

17

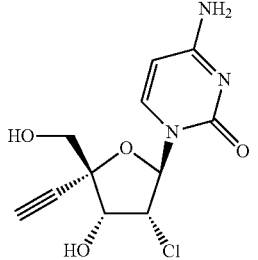

18
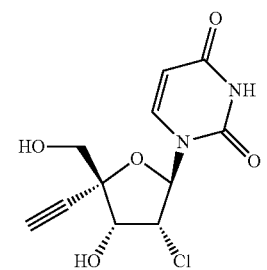
20
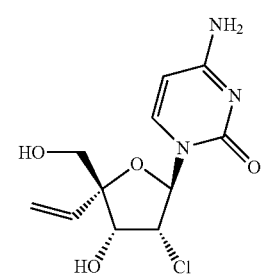
21
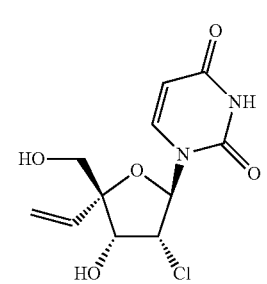
23
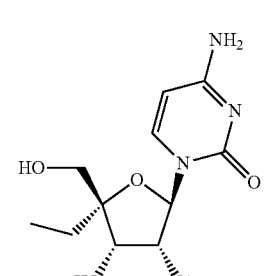
24
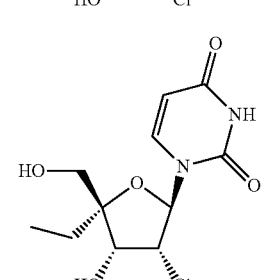
26
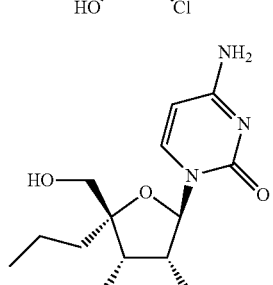
27
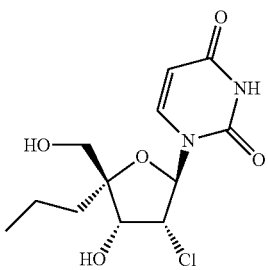
31
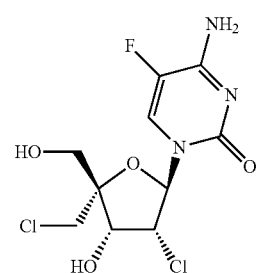
32
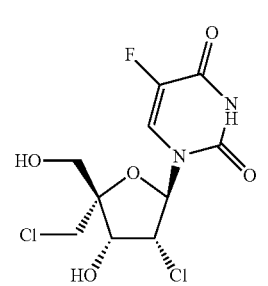
34
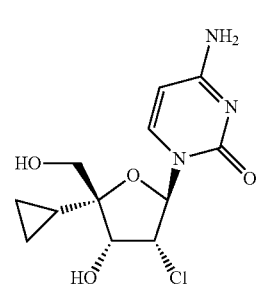
35
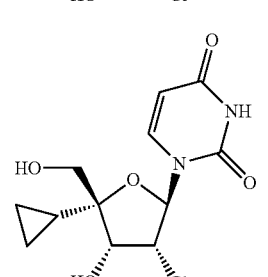
39
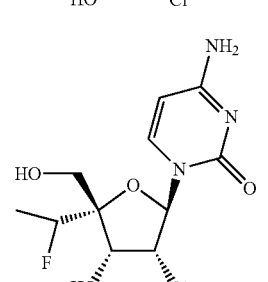

-continued

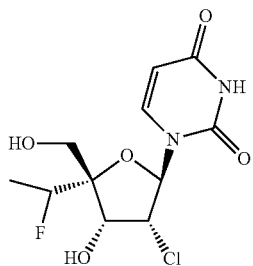

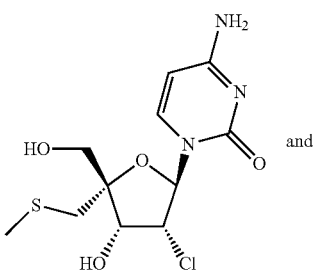
and

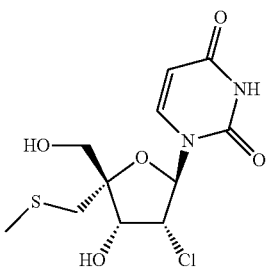

Syntheses of Nucleoside Species

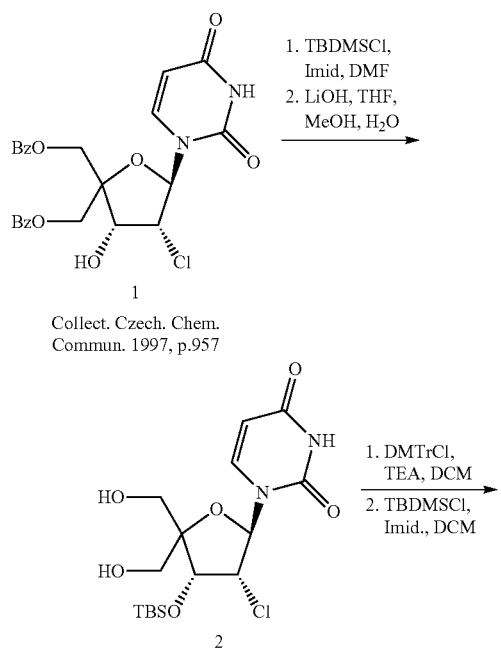

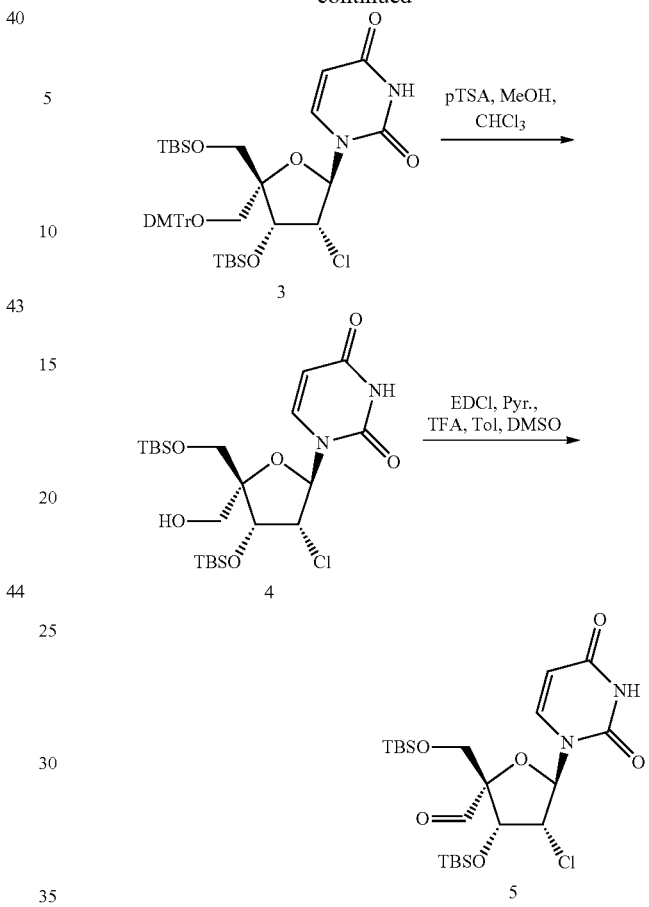

Compound 2: 1-((2R,3R,4R)-4-((tert-butyldimethyl-silyl)oxy)-3-chloro-5,5-bis(hydroxymethyl)tetrahydrofuran-2-yl)pyrimidine-2,4(1H,3H)-dione Compound 1 (1 mmol) is dissolved in DMF (10 mL). To this solution is added TBSCl (1.1 eq), followed by imidazole (1.5 eq). The reaction is stirred until the reaction is complete. The reaction is quenched by slowly adding a saturated aqueous solution of NaHCO$_3$. The mixture is diluted with DCM and water. The layers are separated and the organic layer is extracted with a 5% aqueous solution of LiCl twice. The organic phase is extracted with brine and is then dried over Na$_2$SO$_4$. The drying agent is removed by filtration and the filtrate is concentrated. The product is isolated from the residue by silica gel column chromatography, using a mixture of EtOAc and hexanes as the eluent.

The product from the TBS protection step described above is dissolved in THF (10 mL) and MeOH (5 mL). This solution is cooled in an ice bath and then a 1M solution of LiOH in water (20 eq of LiOH) is added to the first solution. The ice bath is removed and the reaction is stirred until the reaction is complete. The reaction is cooled in an ice bath and brought to neutral pH by slowly adding a 4N aqueous solution of HCl. The neutralized reaction is concentrated and compound 2 is isolated from the residue by silica gel column chromatography, using a mixture of MeOH and DCM as the eluent.

Compound 3: 1-((2R,3R,4R,5R)-5-((bis(4-methoxyphenyl)(phenyl)methoxy)methyl)-4-((tert-butyldimethylsilyl)oxy)-5-(((tert-butyldimethylsilyl)oxy)methyl)-3-chlorotetrahydrofuran-2-yl)pyrimidine-2,4(1H,3H)-dione Compound 2 (1 mmol) is dissolved in DCM (10 mL) and TEA is added (2.5 eq). This solution is cooled to 0° C. and then a separate solution of DMTrCl (1.45 eq) in DCM (5 mL) is slowly added. The reaction is stirred until the reaction is complete. The reaction is quenched by adding MeOH (5 mL) and is then concentrated. The residue is partitioned between DCM and sat. NaHCO$_3$. The layers are separated and the organic layer is extracted with brine and is then dried over Na$_2$SO$_4$. The drying agent is removed by filtration and the filtrate is concentrated. The product is isolated from the residue by silica gel column chromatography, using a mixture of EtOAc and hexanes as the eluent.

The product from the DMTr protection step described above (1 mmol) is dissolved in DCM (10 mL). To this solution is added TBSCl (1.1 eq), followed by imidazole (1.5 eq). The reaction is stirred until the reaction is complete. The reaction is quenched by slowly adding sat. NaHCO$_3$. The mixture is diluted with DCM and water. The layers are separated and the organic layer is extracted with brine and is then dried over Na$_2$SO$_4$. The drying agent is removed by filtration and the filtrate is concentrated. Compound 3 is isolated from the residue by silica gel column chromatography, using a mixture of EtOAc and hexanes as the eluent.

Compound 4: 1-((2R,3R,4R,5R)-4-((tert-butyldimethylsilyl)oxy)-5-(((tert-butyldimethylsilyl)oxy)methyl)-3-chloro-5-(hydroxymethyl)tetrahydrofuran-2-yl)pyrimidine-2,4(1H,3H)-dione Compound 3 (1 mmol) is dissolved in CHCl$_3$ (10 mL). This solution is cooled in an ice bath and a solution of pTSA (1.1 eq) in MeOH (3 mL) is added in a drop-wise fashion. The reaction is stirred until the reaction is complete. The reaction is quenched by adding sat. NaHCO$_3$ and is diluted with DCM. The layers are separated and the organic phase is extracted with brine and is then dried over Na$_2$SO$_4$. The drying agent is removed by filtration and the filtrate is concentrated. Compound 4 is isolated from the residue by silica gel column chromatography, using a mixture of EtOAc and hexanes as the eluent.

Compound 5: (2R,3R,4R,5R)-3-((tert-butyldimethylsilyl)oxy)-2-(((tert-butyldimethylsilyl)oxy)methyl)-4-chloro-5-(2,4-dioxo-3,4-dihydropyrimidin-1(2H)-yl)tetrahydrofuran-2-carbaldehyde Compound 4 (1 mmol) is dissolved in toluene (8 mL) and DMSO (2 mL). To this solution is added EDCl (3 eq). Pyridine (83 L) is then added followed by TFA (42 L). The reaction is stirred until the reaction is complete. The reaction is diluted with EtOAc, and the organic phase is washed with water and then brine. The organic phase is dried over Na$_2$SO$_4$ and the drying agent is removed by filtration. The filtrate is concentrated to yield the crude compound 5, which is used as is in subsequent reactions.

Scheme 2

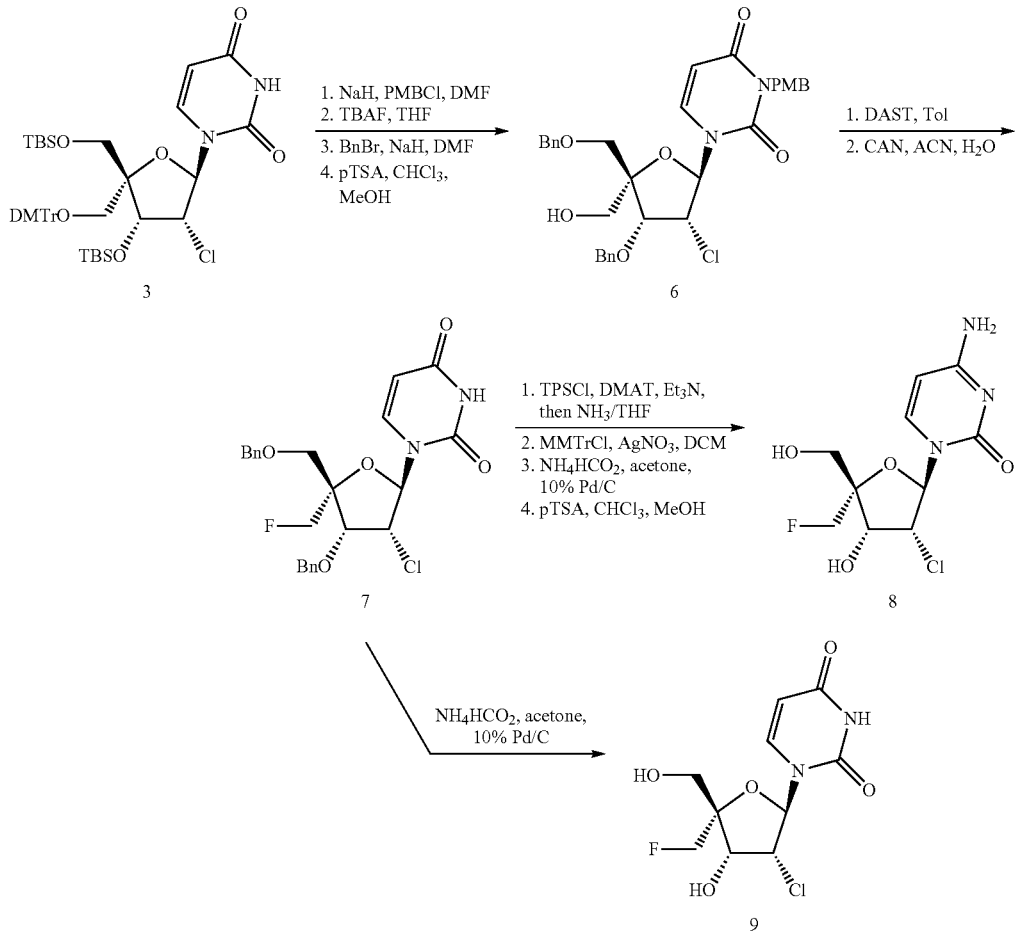

Compound 6: 1-((2R,3R,4R,5R)-4-(benzyloxy)-5-((benzyloxy)methyl)-3-chloro-5-(hydroxymethyl)tetrahydrofuran-2-yl)-3-(4-methoxybenzyl)pyrimidine-2,4(1H,3H)-dione Compound 3 (1 mmol) is added as a solution in DMF (5 mL) to an ice cold slurry of NaH (1.1 eq) in DMF (5 mL). This is allowed to stir for 10 min and then PMBCl is added dropwise. The reaction is allowed to stir until it is determined to be complete. The reaction is quenched by the addition of water and then diluted with EtOAc. The organic and aqueous phases are separated and the organic phase is washed with 5% LiCl (twice), brine (once) and then dried over Na$_2$SO$_4$. The filtrate is concentrated and the PMB-protected compound is purified by silica gel column chromatography, using a mixture of EtOAc and hexanes as the eluent.

The PMB-protected compound (1 mmol) is dissolved in THF and then a 1M solution of TBAF in THF is added. The reaction is stirred until it is determined to be complete. The reaction is quenched with a saturated solution of NH$_4$Cl in water and diluted with DCM. The layers are separated and the organic layer is extracted with brine and dried over Na$_2$SO$_4$. The drying agent is removed by filtration and the filtrate is concentrated. The deprotected diol is isolated from the residue by silica gel column chromatography, using a mixture of DCM and MeOH as the eluent.

The deprotected diol (1 mmol) is added as a solution in DMF (5 mL) to an ice cold slurry of NaH 2.2 eq) in DMF (5 mL). This is allowed to stir for 10 min. and then BnBr is added dropwise. The reaction is allowed to stir until it is determined to be complete. The reaction is quenched by the addition of water and then diluted with EtOAc. The organic and aqueous phases are separated and the organic phase is washed with 5% LiCl (twice), brine (once) and then dried over Na$_2$SO$_4$. The filtrate is concentrated and the Bn-protected compound is purified by silica gel column chromatography, using a mixture of EtOAc and hexanes as the eluent.

The Bn-protected compound (1 mmol) is dissolved in CHCl$_3$ (10 mL). This solution is cooled in an ice bath and a solution of pTSA (1.1 eq) in MeOH (3 mL) is added in a drop-wise fashion. The reaction is stirred until the reaction is complete. The reaction is quenched by adding sat. NaHCO$_3$ and is diluted with DCM. The layers are separated and the organic phase is extracted with brine and is then dried over Na$_2$SO$_4$. The drying agent is removed by filtration and the filtrate is concentrated. Compound 6 is isolated from the residue by silica gel column chromatography, using a mixture of EtOAc and hexanes as the eluent.

Compound 7: 1-((2R,3R,4R,5R)-4-(benzyloxy)-5-((benzyloxy)methyl)-3-chloro-5-(fluoromethyl)tetrahydrofuran-2-yl)pyrimidine-2,4(1H,3H)-dione The compound 6 (1 mmol) is dissolved in toluene (10 mL). This solution is cooled in an ice bath and then DAST (10 eq) is added in a drop-wise fashion. The ice bath is removed and the reaction is allowed to stir until it is determined to be complete. The reaction is quenched by the addition of a saturated solution of NaHCO$_3$ in water and then diluted with EtOAc. The layers are separated and the organic layer is extracted with brine and dried over Na$_2$SO$_4$. The drying agent is removed by filtration and the filtrate is concentrated. The product is isolated from the residue by silica gel column chromatography, using a mixture of EtOAc and hexanes as the eluent.

The product from the previous reaction (1 mmol) is dissolved in a 3:1 mixture of ACN and water (10 mL). CAN (3 eq) is then added in a single portion and the reaction is allowed to stir until it is determined to be complete. The reaction is quenched by the addition of brine and diluted with EtOAc. The layers are separated and the organic layer is dried over Na$_2$SO$_4$. The drying agent is removed by filtration and the filtrate is concentrated. Compound 7 is isolated from the residue by silica gel column chromatography, using a mixture of EtOAc and hexanes as the eluent.

Compound 8: 4-amino-1-((2R,3R,4R,5R)-3-chloro-5-(fluoromethyl)-4-hydroxy-5-(hydroxymethyl)tetrahydrofuran-2-yl)pyrimidin-2(1H)-one Compound 7 (1 mmol) is dissolved in ACN (10 mL) and then DMAP (2 eq), TPSCl (2 eq), and TEA (2 eq) are added. The reaction is stirred at RT until the reaction is determined to be complete. A saturated solution of NH$_3$ in THF (100 mL) is then added to the reaction and stirring is continued at rt until the reaction is determined to be complete. The reaction is concentrated and the cytidine product is isolated by silica gel column chromatography, eluting with a mixture of MeOH and DCM.

The cytidine product (1 mmol) from the previous reaction is dissolved in DCM (10 mL). MMTrCl (3 eq) and AgNO$_3$ (3 eq) are added. The reaction is allowed to stir until it is determined to be complete. The reaction is filtered, the filtrate is extracted with brine and dried over Na$_2$SO$_4$. The drying agent is removed by filtration and the filtrate is concentrated. The MMTr-protected product is isolated from the residue by silica gel column chromatography, using a mixture of EtOAc and hexanes as the eluent.

The MMTr-protected product (1 mmol) from the previous reaction is dissolved in acetone (10 mL). NH$_4$HCO$_2$ (45 eq) and 10% Pd/C (1 g) are added and the reaction refluxed until it is determined to be complete. The reaction is filtered through a pad of Celite and the filtrate is concentrated. The deprotected diol product is isolated from the residue by silica gel column chromatography, using a mixture of DCM and MeOH as the eluent.

The deprotected diol product (1 mmol) from the previous reaction is dissolved in CHCl$_3$ (10 mL). This solution is cooled in an ice bath and a solution of pTSA (1.1 eq) in MeOH (3 mL) is added in a drop-wise fashion. The reaction is stirred until the reaction is complete. The reaction is quenched by adding sat. NaHCO$_3$. The mixture is concentrated, the residue is taken up in MeOH and then filtered. The filtrate is concentrated and compound 8 is isolated from the residue by silica gel column chromatography, using a mixture of DCM and MeOH as the eluent.

Compound 9: 1-((2R,3R,4R,5R)-3-chloro-5-(fluoromethyl)-4-hydroxy-5-(hydroxymethyl)tetrahydrofuran-2-yl)pyrimidine-2,4(1H,3H)-dione Compound 7 (1 mmol) is dissolved in acetone (10 mL). NH$_4$HCO$_2$ (45 eq) and 10% Pd/C (1 g) are added and the reaction refluxed until it is determined to be complete. The reaction is filtered through a pad of Celite and the filtrate is concentrated. Compound 9 is isolated from the residue by silica gel column chromatography, using a mixture of DCM and MeOH as the eluent.

Scheme 3

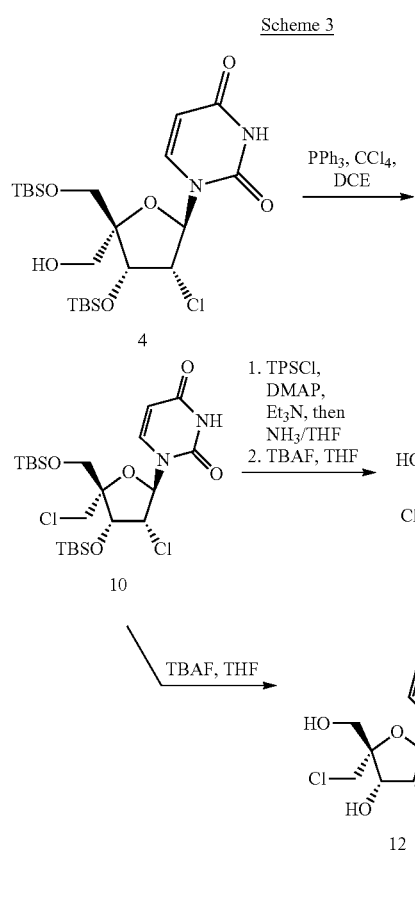

Scheme 4

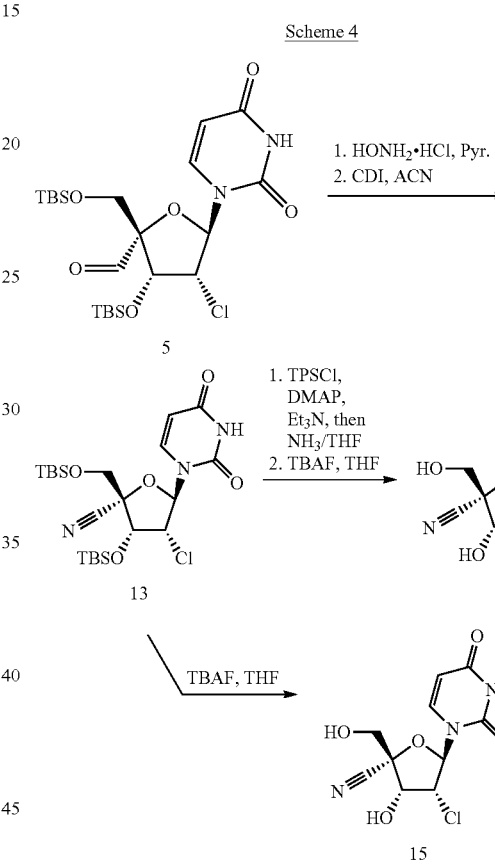

Compound 10: 1-((2R,3R,4R,5R)-4-((tert-butyldimethylsilyl)oxy)-5-(((tert-butyldimethylsilyl)oxy)methyl)-3-chloro-5-(chloromethyl)tetrahydrofuran-2-yl)pyrimidine-2,4(1H,3H)-dione Compound 4 (1 mmol) is dissolved in DCE (10 mL). To this solution is added Ph$_3$P (2 eq) and CCl$_4$ (2 eq). The reaction is heated to 130° C. using microwave irradiation until the reaction is determined to be complete. The reaction is concentrated and compound 10 is isolated from the residue by silica gel column chromatography, using a mixture of EtOAc and hexanes as the eluent.

Compound 11: 4-amino-1-((2R,3R,4R,5R)-3-chloro-5-(chloromethyl)-4-hydroxy-5-(hydroxymethyl)tetrahydrofuran-2-yl)pyrimidin-2(1H)-one Compound 10 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of NH$_3$ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 11 is isolated from the residue by silica gel column chromatography using a mixture of MeOH and DCM as the eluent.

Compound 12: 1-((2R,3R,4R,5R)-3-chloro-5-(chloromethyl)-4-hydroxy-5-(hydroxymethyl)tetrahydrofuran-2-yl)pyrimidine-2,4(1H,3H)-dione Compound 10 (1 mmol) is dissolved in THF (10 mL) and a solution of 1M TBAF in THF (3 eq) is added at rt. The reaction is stirred until the reaction is determined to be complete. The reaction is concentrated and compound 12 is isolated from the residue by silica gel column chromatography using a mixture of MeOH and DCM as the eluent.

Compound 13: (2R,3R,4R,5R)-3-((tert-butyldimethylsilyl)oxy)-2-(((tert-butyldimethylsilyl)oxy)methyl)-4-chloro-5-(2,4-dioxo-3,4-dihydropyrimidin-1(2H)-yl)tetrahydrofuran-2-carbonitrile Compound 5 (1 mmol) is dissolved in pyridine (10 mL). To this solution is added HONH$_2$HCl (1.5 eq). The reaction is stirred until it is determined to be complete. The reaction is quenched by the addition of water. The reaction is extracted with EtOAc and the organic phase is dried over Na$_2$SO$_4$. The drying agent is removed by filtration and the filtrate is concentrated. The crude product is dissolved in ACN (10 mL) and CDI (1.5 eq) is added. The reaction is stirred until it is determined to be complete and is then quenched by adding water. The mixture is extracted with DCM and the combined organics are dried over Na$_2$SO$_4$. The drying agent is removed by filtration and the filtrate is concentrated. Compound 13 is isolated from the residue by silica gel column chromatography, using a mixture of EtOAc and hexanes as the eluent.

Compound 14: (2R,3R,4R,5R)-5-(4-amino-2-oxopyrimidin-1(2H)-yl)-4-chloro-3-hydroxy-2-(hydroxymethyl)tetrahydrofuran-2-carbonitrile Compound 13 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of NH₃ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 14 is isolated from the residue by silica gel column chromatography using a mixture of MeOH and DCM as the eluent.

Compound 15: (2R,3R,4R,5R)-4-chloro-5-(2,4-dioxo-3,4-dihydropyrimidin-1(2H)-yl)-3-hydroxy-2-(hydroxymethyl)tetrahydrofuran-2-carbonitrile Compound 13 (1 mmol) is dissolved in THF (10 mL) and a solution of 1M TBAF in THF (3 eq) is added at rt. The reaction is stirred until the reaction is determined to be complete. The reaction is concentrated and compound 15 is isolated from the residue by silica gel column chromatography using a mixture of MeOH and DCM as the eluent

Compound 16: 1-((2R,3R,4R,5R)-4-((tert-butyldimethylsilyl)oxy)-5-(((tert-butyl di methylsilyl)oxy)methyl)-3-chloro-5-ethynyltetrahydrofuran-2-yl)pyrimidine-2,4(1H,3H)-dione (Ph)₃PCH₂BrBr (2 mmol) is dissolved in THF (10 mL). This solution is cooled to −78° C. and tBuOK (1M/THF, 3 mmol) is added in a drop-wise manner. This solution is stirred at −78° C. and then a solution of compound 5 in THF (5 mL) is added in a drop-wise manner. The reaction is then allowed to warm to room temperature and stirring is continued until it is determined that the reaction is complete. The reaction is quenched by the addition of saturated aqueous solution of NH₄Cl. The mixture is extracted with EtOAc and the combined organic extracts are extracted with brine and dried over Na₂SO₄. The drying agent is removed by filtration and the filtrate is concentrated. The product is isolated from this residue by silica gel column chromatography, using a mixture of EtOAc and hexanes as the eluent.

The product from the previous reaction (1 mmol) is dissolved in THF (10 mL). This solution is cooled to −78° C. and then tBuOK (1M/THF, 3 eq) is added in a drop-wise manner. The reaction is allowed to stir until it is determined to be complete. The reaction is quenched by the addition of sat. NH₄Cl. The mixture is extracted with EtOAc and the combined organic extracts are extracted with brine and dried over Na₂SO₄. The drying agent is removed by filtration and the filtrate is concentrated. Compound 16 is isolated from this residue by silica gel column chromatography, using a mixture of EtOAc and hexanes as the eluent.

Compound 17: 4-amino-1-((2R,3R,4R,5R)-3-chloro-5-ethynyl-4-hydroxy-5-(hydroxymethyl)tetrahydrofuran-2-yl)pyrimidin-2(1H)-one Compound 16 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of NH₃ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 17 is isolated from the residue by silica gel column chromatography using a mixture of MeOH and DCM as the eluent.

Compound 18: 1-((2R,3R,4R,5R)-3-chloro-5-ethynyl-4-hydroxy-5-(hydroxymethyl)tetrahydrofuran-2-yl)pyrimidine-2,4(1H,3H)-dione Compound 16 (1 mmol) is dissolved in THF (10 mL) and a solution of 1M TBAF in THF (3 eq) is added at rt. The reaction is stirred until the reaction is determined to be complete. The reaction is concentrated and compound 18 is isolated from the residue by silica gel column chromatography using a mixture of MeOH and DCM as the eluent.

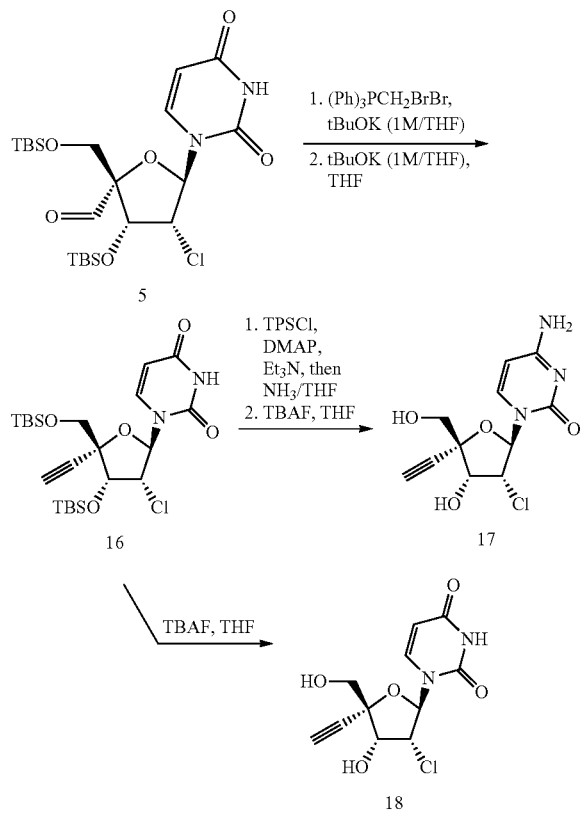

Scheme 5

Scheme 6

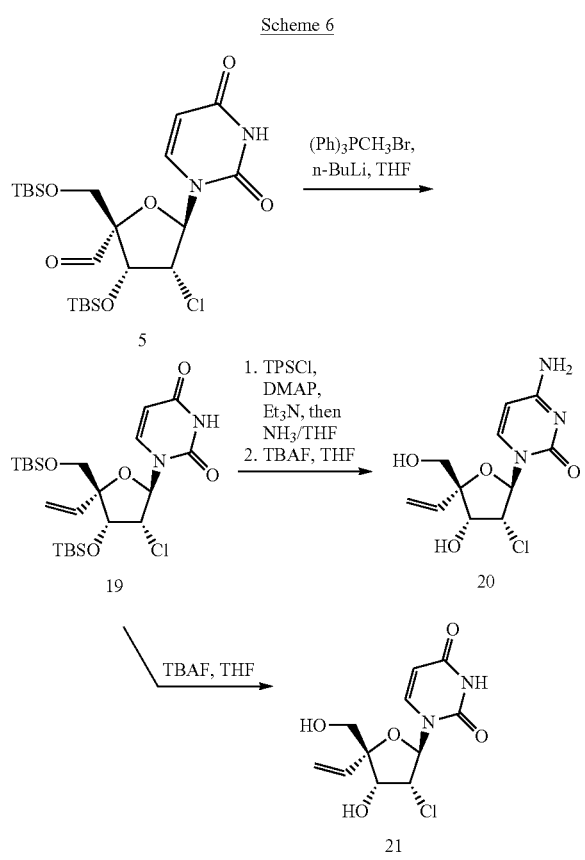

Compound 19: 1-((2R,3R,4R,5R)-4-((tert-butyldimethylsilyl)oxy)-5-(((tert-butyldimethylsilyl)oxy)methyl)-3-chloro-5-vinyltetrahydrofuran-2-yl)pyrimidine-2,4(1H,3H)-dione (Ph)₃PCH₃Br (4 mmol) is suspended in THF (10 mL) and then nBuLi (2.5M/hexanes, 4 mmol) is added in a drop-wise manner. The cold bath is replaced with an ice bath and the reaction is stirred for 1 h. To this solution is added a solution of compound 5 (1 mmol) in THF (5 mL). The ice bath is removed and the reaction is allowed to stir at room temperature until it is determined to be complete. The reaction is quenched by the addition of sat. NH4Cl and the mixture is extracted with EtOAc. The organic phase is extracted with brine and is then dried over Na₂SO₄. The drying agent is removed by filtration and the filtrate is concentrated. Compound 19 is isolated from this residue by silica gel column chromatography, using a mixture of EtOAc and hexanes as the eluent.

Compound 20: 4-amino-1-((2R,3R,4R,5R)-3-chloro-4-hydroxy-5-(hydroxymethyl)-5-vinyltetrahydrofuran-2-yl)pyrimidin-2(1H)-one Compound 19 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of NH₃ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 20 is isolated from the residue by silica gel column chromatography using a mixture of MeOH and DCM as the eluent.

Compound 21: 1-((2R,3R,4R,5R)-3-chloro-4-hydroxy-5-(hydroxymethyl)-5-vinyltetrahydrofuran-2-yl)pyrimidine-2,4(1H,3H)-dione Compound 19 (1 mmol) is dissolved in THF (10 mL) and a solution of 1M TBAF in THF (3 eq) is added at rt. The reaction is stirred until the reaction is determined to be complete. The reaction is concentrated and compound 21 is isolated from the residue by silica gel column chromatography using a mixture of MeOH and DCM as the eluent.

Scheme 7

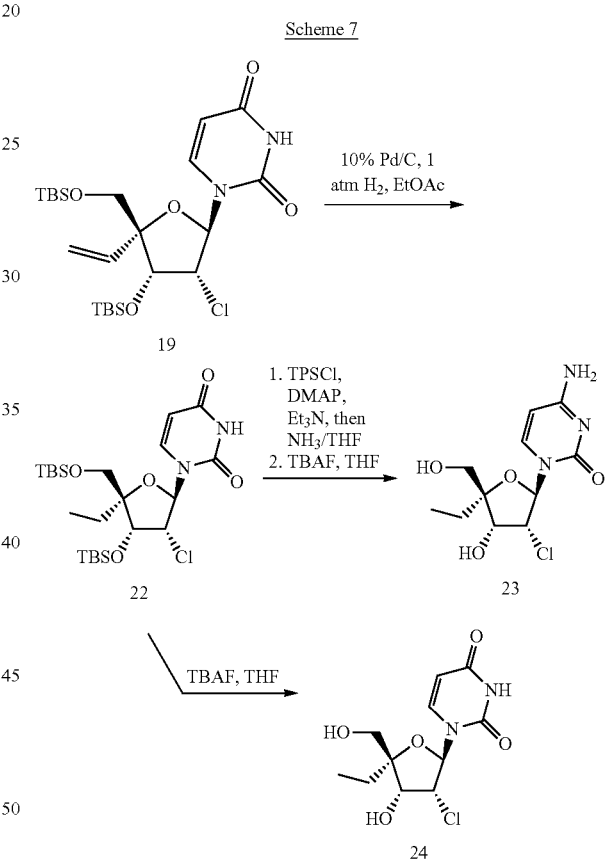

Compound 22: 1-((2R,3R,4R,5R)-4-((tert-butyldimethylsilyl)oxy)-5-(((tert-butyldimethylsilyl)oxy)methyl)-3-chloro-5-ethyltetrahydrofuran-2-yl)pyrimidine-2,4(1H,3H)-dione Compound 19 (1 mmol) is dissolved in EtOAc (10 mL). 10% Pd/C (1 g) is added and the reaction vessel atmosphere is evacuated and refilled with H₂. The reaction is stirred vigorously until it is determined to be complete. The reaction is filtered through a pad of Celite. The filtrate is concentrated and compound 22 isolated from this residue by silica gel column chromatography, using a mixture of EtOAc and hexanes as the eluent.

Compound 23: 4-amino-1-((2R,3R,4R,5R)-3-chloro-5-ethyl-4-hydroxy-5-(hydroxymethyl)tetrahydrofuran-2-yl)pyrimidin-2(1H)-one Compound 22 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of $NH_3$ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 23 is isolated from the residue by silica gel column chromatography using a mixture of MeOH and DCM as the eluent.

Compound 24: 1-((2R,3R,4R,5R)-3-chloro-5-ethyl-4-hydroxy-5-(hydroxymethyl)tetrahydrofuran-2-yl)pyrimidine-2,4(1H,3H)-dione Compound 22 (1 mmol) is dissolved in THF (10 mL) and a solution of 1M TBAF in THF (3 eq) is added at rt. The reaction is stirred until the reaction is determined to be complete. The reaction is concentrated and compound 24 is isolated from the residue by silica gel column chromatography using a mixture of MeOH and DCM as the eluent.

Compound 25: 1-((2R,3R,4R,5R)-4-((tert-butyldimethylsilyl)oxy)-5-(((tert-butyldimethylsilyl)oxy)methyl)-3-chloro-5-propyltetrahydrofuran-2-yl)pyrimidine-2,4(1H,3H)-dione Compound 5 is converted to compound 25 in a manner similar to the conversion of compound 5 to compound 22 (a Wittig reaction followed by a Pd/C catalyzed hydrogenation of the resulting olefin).

Compound 26: 4-amino-1-((2R,3R,4R,5R)-3-chloro-4-hydroxy-5-(hydroxymethyl)-5-propyltetrahydrofuran-2-yl)pyrimidin-2(1H)-one Compound 25 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of $NH_3$ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 26 is isolated from the residue by silica gel column chromatography using a mixture of MeOH and DCM as the eluent.

Compound 27: 1-((2R,3R,4R,5R)-3-chloro-4-hydroxy-5-(hydroxymethyl)-5-propyltetrahydrofuran-2-yl)pyrimidine-2,4(1H,3H)-dione Compound 25 (1 mmol) is dissolved in THF (10 mL) and a solution of 1M TBAF in THF (3 eq) is added at rt. The reaction is stirred until the reaction is determined to be complete. The reaction is concentrated and compound 27 is isolated from the residue by silica gel column chromatography using a mixture of MeOH and DCM as the eluent.

Scheme 8

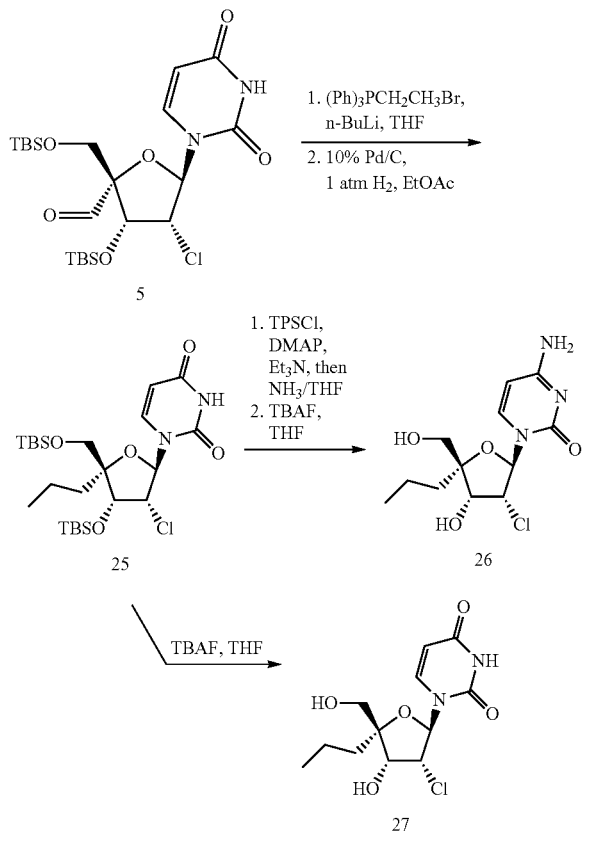

Scheme 9

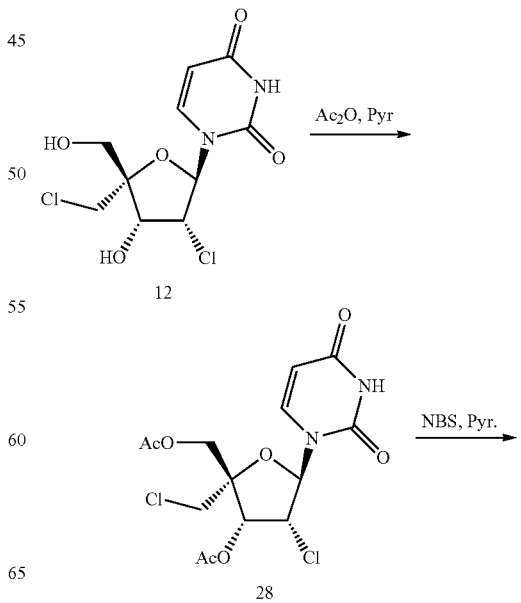

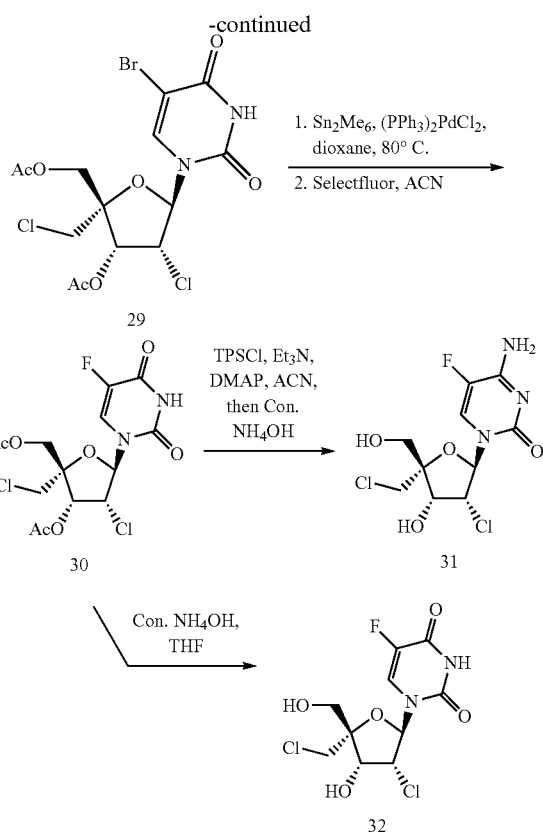

dissolved in ACN (10 mL) and Selectfluor (2.2 eq) is added. The reaction is stirred at rt until the reaction is determined to be complete. The reaction is concentrated and compound 34 is isolated from the residue by silica gel column chromatography using a mixture of EtOAc and hexanes as the eluent.

Compound 31: 4-amino-1-((2R,3R,4R,5R)-3-chloro-5-(chloromethyl)-4-hydroxy-5-(hydroxymethyl)tetrahydrofuran-2-yl)-5-fluoropyrimidin-2(1H)-one Compound 30 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of NH$_3$ in water (50 mL) is then added to the reaction and stirring is continued at rt until the reaction is determined to be complete. The reaction is concentrated and compound 35 is isolated by silica gel column chromatography, eluting with a mixture of MeOH and DCM.

Compound 32: 1-((2R,3R,4R,5R)-3-chloro-5-(chloromethyl)-4-hydroxy-5-(hydroxymethyl)tetrahydrofuran-2-yl)-5-fluoropyrimidine-2,4(1H,3H)-dione Compound 30 (1 mmol) is dissolved in THF (10 mL) and a saturated solution of NH$_3$ in water (50 mL) is then added at rt. The reaction is stirred until the reaction is determined to be complete. The reaction is concentrated and compound 36 is isolated from the residue by silica gel column chromatography using a mixture of MeOH and DCM as the eluent.

Compound 28: ((2R,3R,4R,5R)-3-acetoxy-4-chloro-2-(chloromethyl)-5-(2,4-dioxo-3,4-dihydropyrimidin-1(2H)-yl)tetrahydrofuran-2-yl)methyl acetate Compound 12 (1 mmol) is dissolved in pyridine (10 mL) and Ac$_2$O (2.1 eq) is added. The reaction is stirred at rt until the reaction is determined to be complete. The reaction is concentrated and compound 28 is isolated from the residue by silica gel column chromatography using a mixture of EtOAc and hexanes as the eluent.

Compound 29: ((2R,3R,4R,5R)-3-acetoxy-5-(5-bromo-2,4-dioxo-3,4-dihydropyrimidin-1(2H)-yl)-4-chloro-2-(chloromethyl)tetrahydrofuran-2-yl)methyl acetate Compound 28 (1 mmol) is dissolved in pyridine (10 mL) and NBS (2 eq) is added. The reaction is stirred at rt until the reaction is determined to be complete. The reaction is concentrated and compound 29 is isolated from the residue by silica gel column chromatography using a mixture of EtOAc and hexanes as the eluent.

Compound 30: ((2R,3R,4R,5R)-3-acetoxy-4-chloro-2-(chloromethyl)-5-(5-fluoro-2,4-dioxo-3,4-dihydropyrimidin-1(2H)-yl)tetrahydrofuran-2-yl)methyl acetate Compound 29 (1 mmol) is dissolved in dioxane (10 mL). To this solution is added Sn$_2$Me$_6$ (2 eq) and (Ph$_3$P)$_2$PdCl$_2$ (0.1 eq). The reaction is stirred at 80° C. until the reaction is determined to be complete. The reaction is concentrated and the stannylated product is isolated from the residue by silica gel column chromatography using a mixture of EtOAc and hexanes as the eluent. The stannane (1 mmol) is Scheme 10

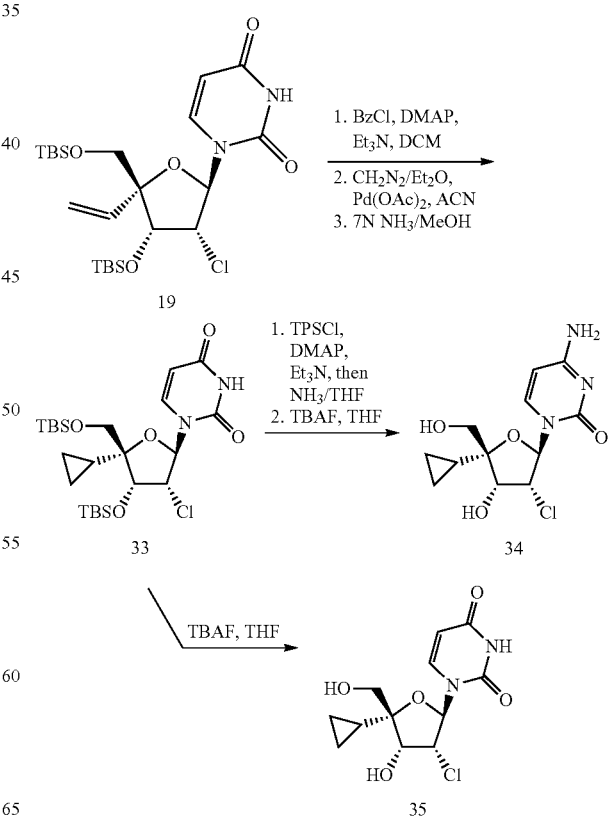

Compound 33: 1-((2R,3R,4R,5R)-4-((tert-butyldimethylsilyl)oxy)-5-(((tert-butyldimethylsilyl)oxy)methyl)-3-chloro-5-cyclopropyltetrahydrofuran-2-yl)pyrimidine-2,4(1H,3H)-dione Compound 19 (1 mmol) is dissolved in DCM (10 mL). To this solution is added BzCl (1eg), Et₃N (1.5 eq) and DMAP (0.1 eq). The reaction is stirred until the reaction is determined to be complete. The reaction is quenched by the addition of a saturated aqueous solution of NaHCO₃. This mixture is diluted with DCM and the layers are separated. The organic phase is extracted with 0.1N HCl, brine and then dried over Na₂SO₄. The drying agent is removed by filtration and the filtrate is concentrated. The benzoylated product is isolated from the residue by silica gel column chromatography using a mixture of EtOAc and hexanes as the eluent.

The benzoylated product (1 mmol) is combined with Pd(OAc)₂ (0.1 eq) in ACN (10 mL) and this solution is added to a solution of CH₂N₂ in Et₂O (100 mL). The reaction is stirred until the reaction is determined to be complete. The reaction is quenched by the addition AcOH. The mixture is extracted with a saturated aqueous solution of NaHCO₃, brine and then dried over Na₂SO₄. The drying agent is removed by filtration and the filtrate is concentrated.

The crude cyclopropanated product (1 mmol) is taken up 7N NH₃ in MeOH. The reaction is stirred until the reaction is determined to be complete. The reaction is concentrated and compound 33 is isolated from the residue by silica gel column chromatography using a mixture of EtOAc and hexanes as the eluent.

Compound 34: 4-amino-1-((2R,3R,4R,5R)-3-chloro-5-cyclopropyl-4-hydroxy-5-(hydroxymethyl)tetrahydrofuran-2-yl)pyrimidin-2(1H)-one Compound 22 (1 mmol) is dissolved in ACN (10 mL) and then DMAP (2 eq), TPSCl (2 eq), and TEA (2 eq) are added. The reaction is stirred at rt until the reaction is determined to be complete. A saturated solution of NH₃ in THF (100 mL) is then added to the reaction and stirring is continued at rt until the reaction is determined to be complete. The reaction is concentrated and the product is isolated by silica gel column chromatography, eluting with a mixture of MeOH and DCM.

The product from the above described reaction is dissolved in THF (10 mL) and a solution of 1M TBAF in THF (3 eq) is added at rt. The reaction is stirred until the reaction is determined to be complete. The reaction is concentrated and compound 34 is isolated from the residue by silica gel column chromatography using a mixture of MeOH and DCM as the eluent.

Compound 35: 1-((2R,3R,4R,5R)-3-chloro-5-cyclopropyl-4-hydroxy-5-(hydroxymethyl)tetrahydrofuran-2-yl)pyrimidine-2,4(1H,3H)-dione Compound 33 (1 mmol) is dissolved in THF (10 mL) and a solution of 1M TBAF in THF (3 eq) is added at rt. The reaction is stirred until the reaction is determined to be complete. The reaction is concentrated and compound 35 is isolated from the residue by silica gel column chromatography using a mixture of MeOH and DCM as the eluent.

Scheme 11

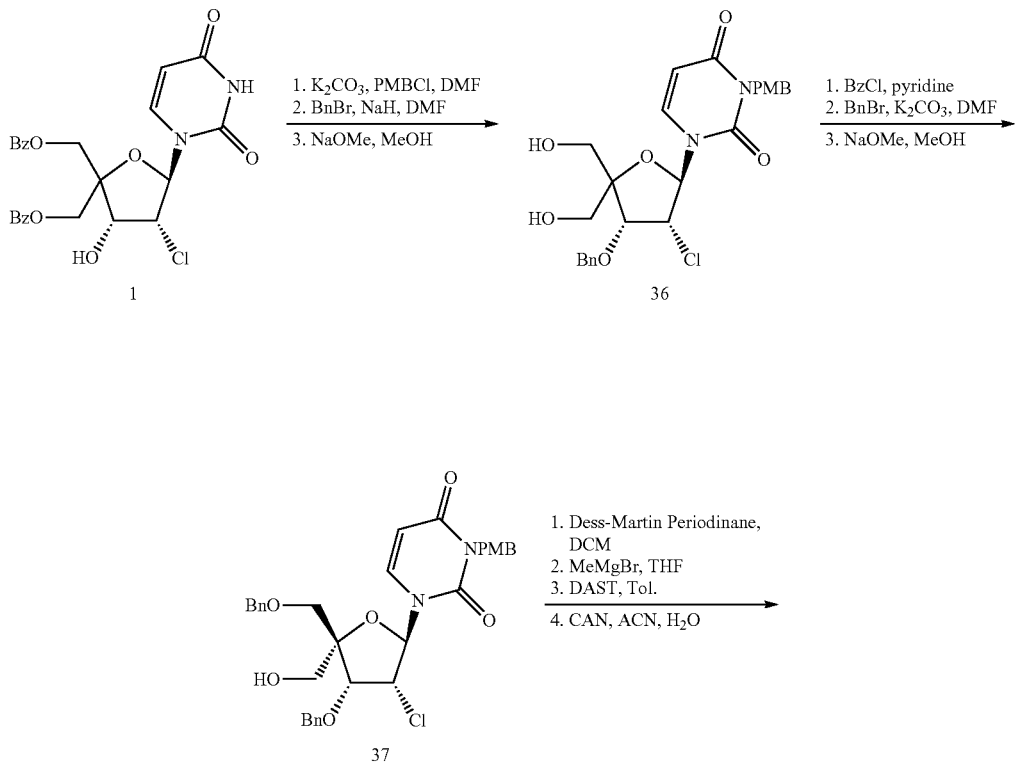

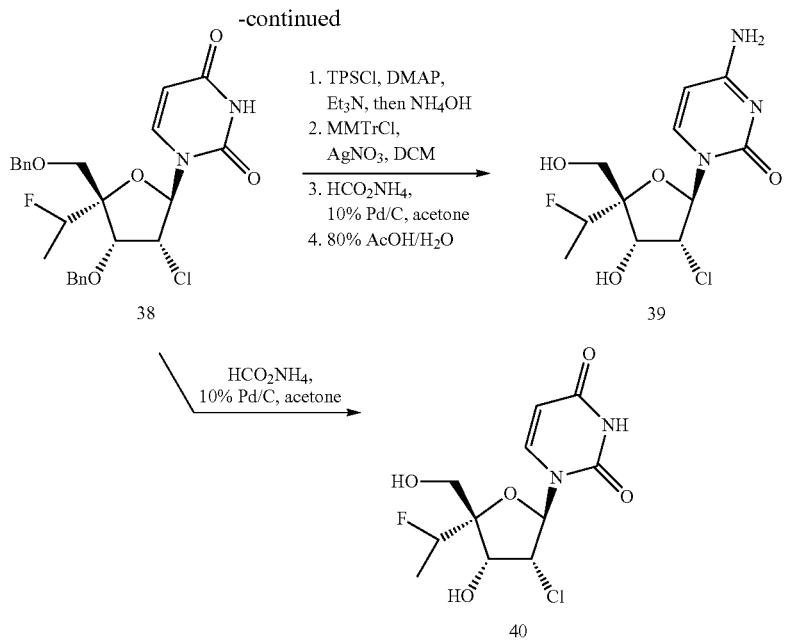

Compound 36: 1-((2R,3R,4R)-4-(benzyloxy)-3-chloro-5,5-bis(hydroxymethyl)tetrahydrofuran-2-yl)-3-(4-methoxybenzyl)pyrimidine-2,4(1H,3H)-dione Compound 1 (1 mmol) is dissolved in DMF (10 mL). To this solution is added $K_2CO_3$ (5 eq) and then PMBCl (1.1 eq). The reaction is stirred until the reaction is determined to be complete. The reaction is diluted with EtOAc and water. The layers are separated and the organic phase is washed with a 5% solution of LiCl in water (twice) and brine. The organic phase is then dried over $Na_2SO_4$. The drying agent is removed by filtration and the filtrate is concentrated. The resulting residue is dissolved in DMF (10 mL) and cooled to 0° C. To this cooled solution is added NaH (1.1 eq), followed by BnBr (1.2 eq). The reaction is stirred until the reaction is determined to be complete. The reaction is quenched by the addition of a saturated solution of $NH_4Cl$ in water. The mixture is diluted with EtOAc. The layers are separated and the organic phase is washed with a 5% solution of LiCl in water (twice) and brine. The organic phase is then dried over $Na_2SO_4$. The drying agent is removed by filtration and the filtrate is concentrated. The Bn-protected material is purified from this residue by silica gel column chromatography using a mixture of EtOAc and hexanes as the eluent.

The Bn-protected compound (1 mmol) is then dissolved in MeOH (10 mL) and NaOMe (15 eq) is added. The reaction is stirred until the reaction is determined to be complete. The reaction is quenched by the addition of AcOH and the resulting mixture is concentrated. Compound 36 is purified from this residue by silica gel column chromatography using a mixture of EtOAc and hexanes as the eluent.

Compound 37: 1-((2R,3R,4R,5R)-4-(benzyloxy)-5-((benzyloxy)methyl)-3-chloro-5-(hydroxymethyl)tetrahydrofuran-2-yl)-3-(4-methoxybenzyl)pyrimidine-2,4(1H,3H)-dione Compound 36 (1 mmol) is dissolved in pyridine (10 mL). To this solution is added BzCl (1 eq). The reaction is stirred until the reaction is determined to be complete. The reaction is diluted with EtOAc and water. The layers are separated and the organic phase is washed with water and brine. The organic phase is then dried over $Na_2SO_4$. The drying agent is removed by filtration and the filtrate is concentrated. The mono-Bz protected material is purified from this residue by silica gel column chromatography using a mixture of EtOAc and hexanes as the eluent.

The above Bz-protected material (1 mmol) is dissolved in DMF (10 mL). To this solution is added $Cs_2CO_3$ (5 eq) and then BnBr (1.1 eq). The reaction is stirred until the reaction is determined to be complete. The reaction is diluted with EtOAc and water. The layers are separated and the organic phase is washed with a 5% solution of LiCl in water (twice) and brine. The organic phase is then dried over $Na_2SO_4$. The drying agent is removed by filtration and the filtrate is concentrated. The bisBn-protected material is purified from this residue by silica gel column chromatography using a mixture of EtOAc and hexanes as the eluent.

The bisBn-protected compound (1 mmol) is then dissolved in MeOH (10 mL) and NaOMe (15 eq) is added. The reaction is stirred until the reaction is determined to be complete. The reaction is quenched by the addition of AcOH and the resulting mixture is concentrated. Compound 37 is purified from this residue by silica gel column chromatography using a mixture of EtOAc and hexanes as the eluent.

Compound 38: 1-((2R,3R,4R,5R)-4-(benzyloxy)-5-((benzyloxy)methyl)-3-chloro-5-((R)-1-fluoroethyl)tetrahydrofuran-2-yl)pyrimidine-2,4(1H,3H)-dione Compound 37 (1 mmol) is dissolved in DCM (10 mL). To this solution is added Dess-Martin Periodinane (1.1 eq). The reaction is stirred until the reaction is determined to be complete. The reaction is concentrated and the product aldehyde is isolated from the residue by silica gel column chromatography using a mixture of EtOAc and hexanes as the eluent.

The aldehyde from above (1 mmol) is dissolved in THF (10 mL) and the solution is cooled to −78° C. To this cooled solution is added MeMgBr (3 eq). The reaction is stirred until the reaction is determined to be complete. The reaction is quenched by the addition of a saturated aqueous solution of NH$_4$Cl. The resulting mixture is diluted with EtOAc and the layers are separated. The organic phase is then dried over Na$_2$SO$_4$. The drying agent is removed by filtration and the filtrate is concentrated. The product alcohol is purified from this residue by silica gel column chromatography using a mixture of EtOAc and hexanes as the eluent.

The alcohol from above (1 mmol) is dissolved in toluene (10 mL). To this solution is added DAST (5 eq). The reaction is stirred until the reaction is determined to be complete. The reaction is quenched by the addition of a saturated aqueous solution of Na$_2$CO$_3$. The resulting mixture is diluted with EtOAc and the layers are separated. The organic phase is then dried over Na$_2$SO$_4$. The drying agent is removed by filtration and the filtrate is concentrated. The product fluoride is purified from this residue by silica gel column chromatography using a mixture of EtOAc and hexanes as the eluent.

The fluoride from above (1 mmol) is dissolved in a 3:1 mixture of ACN:H2O (10 mL). To this solution is added CAN (4 eq). The reaction is stirred until the reaction is determined to be complete. The reaction is diluted with brine and EtOAc. The layers are separated and the organic phase is then dried over Na$_2$SO$_4$. The drying agent is removed by filtration and the filtrate is concentrated. Compound 38 is purified from this residue by silica gel column chromatography using a mixture of EtOAc and hexanes as the eluent.

Compound 39: 4-amino-1-((2R,3R,4R,5R)-3-chloro-5-((R)-1-fluoroethyl)-4-hydroxy-5-(hydroxymethyl)tetrahydrofuran-2-yl)pyrimidin-2(1H)-one Compound 38 (1 mmol) is dissolved in ACN (10 mL) and then DMAP (2 eq), TPSCl (2 eq), and TEA (2 eq) are added. The reaction is stirred at rt until the reaction is determined to be complete. Concentrated aqueous NH$_4$OH (15 mL) is then added to the reaction and stirring is continued at rt until the reaction is determined to be complete. The reaction is concentrated and the product is isolated by silica gel column chromatography, eluting with a mixture of EtOAc and hexanes.

The aminated product from above (1 mmol) is dissolved in DCM (10 mL). To this solution is added MMTrCl (2.1 eq) and AgNO$_3$ (2.1 eq). The reaction is stirred until the reaction is determined to be complete. The reaction is filtered and the filtrate is washed with brine and then dried over Na$_2$SO$_4$. The drying agent is removed by filtration and the filtrate is concentrated. The MMTr-protected product is isolated from the residue by silica gel column chromatography, eluting with a mixture of EtOAc and hexanes.

The MMTr-protected product from above (1 mmol) is dissolved in acetone (10 mL). To this solution is added HCO$_2$NH$_4$ (20 eq) and 10% Pd/C (2 g). The reaction is refluxed until the reaction is determined to be complete. The reaction is cooled and the filtered. The filtrate is concentrated and the residue is taken back up in EtOAc. This solution is extracted with brine and dried over Na$_2$SO$_4$. The drying agent is removed by filtration and the filtrate is concentrated. The deprotected product is purified from this residue by silica gel column chromatography using a mixture of MeOH and DCM as the eluent.

The deprotected product from above (1 mmol) is dissolved in an 80% aqueous solution of AcOH. The reaction is stirred until the reaction is determined to be complete. The solvent is removed from the reaction by evaporation and the residue is coevaped twice with toluene. Compound 39 is purified from this residue by silica gel column chromatography using a mixture of MeOH and DCM as the eluent.

Compound 40: 1-((2R,3R,4R,5R)-3-chloro-5-((R)-1-fluoroethyl)-4-hydroxy-5-(hydroxymethyl)tetrahydrofuran-2-yl)pyrimidine-2,4(1H,3H)-dione Compound 38 (1 mmol) is dissolved in acetone (10 mL). To this solution is added HCO$_2$NH$_4$ (20 eq) and 10% Pd/C (2 g). The reaction is refluxed until the reaction is determined to be complete. The reaction is cooled and the filtered. The filtrate is concentrated and the residue is taken back up in DCM. This solution is extracted with brine and dried over Na$_2$SO$_4$. The drying agent is removed by filtration and the filtrate is concentrated. The deprotected product is purified from this residue by silica gel column chromatography using a mixture of MeOH and DCM as the eluent.

Scheme 13

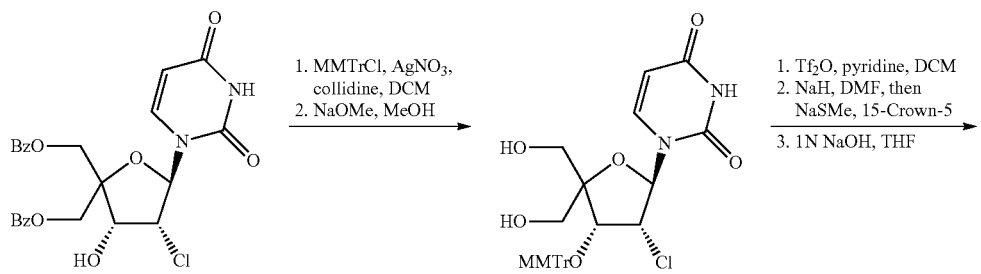

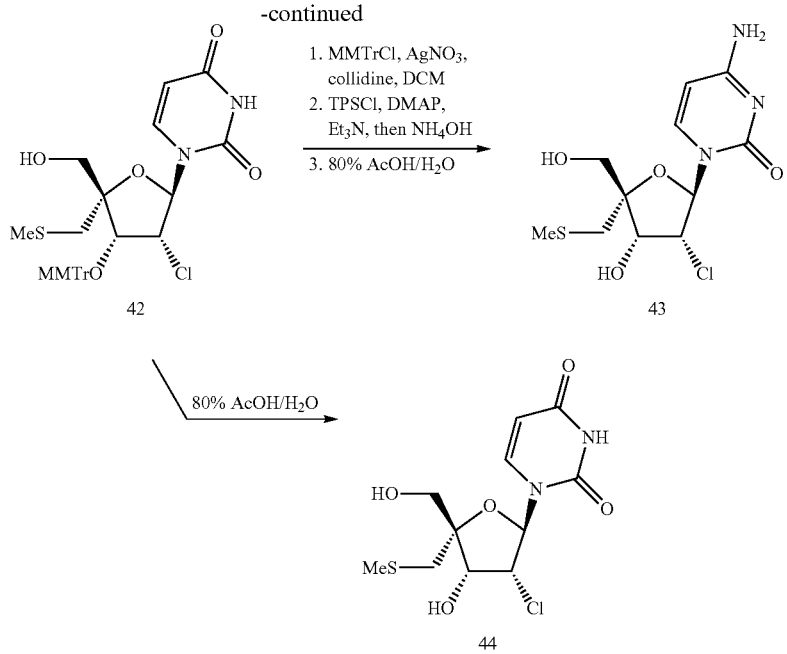

Compound 41: 1-((2R,3R,4R)-3-chloro-5,5-bis(hydroxymethyl)-4-((4-methoxyphenyl)diphenylmethoxy)tetrahydrofuran-2-yl)pyrimidine-2,4(1H,3H)-dione Compound 1 (1 mmol) is dissolved in DCM (10 mL). To this solution is added AgNO$_3$ (2 eq) and collidine (1 eq) and MMTrCl (4 eq). The reaction stirred until the reaction is determined to be complete. The reaction is filtered through celite, washing forward with DCM. The filtrate is washed with 1M citric acid, half-saturated brine and 5% NaHCO$_3$. The organic phase is then dried over Na$_2$SO$_4$. The drying agent is removed by filtration and the filtrate is concentrated. The MMTr-protected product is isolated from the residue by silica gel column chromatography, eluting with a mixture of EtOAc and hexanes.

The MMTr-protected compound from above (1 mmol) is then dissolved in MeOH (10 mL) and NaOMe (15 eq) is added. The reaction is stirred until the reaction is determined to be complete. The reaction is cooled to 0° C. and quenched by the addition of AcOH (15 eq) and the resulting mixture is concentrated. Compound 41 is purified from this residue by silica gel column chromatography using a mixture of MeOH and DCM as the eluent.

Compound 42: 1-((2R,3R,4R,5R)-3-chloro-5-(hydroxymethyl)-4-((4-methoxyphenyl)diphenylmethoxy)-5-((methylthio)methyl)tetrahydrofuran-2-yl)pyrimidine-2,4(1H,3H)-dione Compound 41 is (1 mmol) dissolved in DCM (10 mL). To this solution is added pyridine (10 mL) is added and the reaction is cooled to −35° C. Tf$_2$O (2.1 eq) is added to the reaction the reaction is stirred at −35° C. until the reaction is determined to be complete. The reaction is quenched by the addition of water. The mixture is extracted with EtOAc and the combined organic washes are dried over Na$_2$SO$_4$. The filtering agent is removed by filtration and the filtrate is concentrated. The bis-triflated product is isolated from the residue by silica gel column chromatography, eluting with a mixture of EtOAc and hexanes.

The bis-triflated product from above (1 mmol) is dissolved in DMF (10 mL). This solution is cooled to 0° C. and NaH (1.1 eq) is added. The reaction is stirred until the reaction is determined to be complete. To this mixture is added NaSMe (3 eq) and 15-Crown-5 (0.1 eq). The reaction is stirred until the reaction is determined to be complete. The reaction is diluted EtOAc and a saturated aqueous solution of NH$_4$Cl. The layers are separated and the organic phase is extracted brine and dried over Na$_2$SO$_4$. The filtering agent is removed by filtration and the filtrate is concentrated. The anhydro product is isolated from the residue by silica gel column chromatography, eluting with a mixture of EtOAc and hexanes.

The anhydro product from above (1 mmol) is dissolved in THF (10 mL). To this solution is added a 1N aqueous solution of NaOH (1.1 eq). The reaction is stirred until the reaction is determined to be complete. The reaction is diluted with EtOAc and a saturated aqueous solution of NaHCO$_3$. The layers are separated and the organic phase is extracted with brine and dried over Na$_2$SO$_4$. The drying agent is removed by filtration and the filtrate is concentrated. Compound 42 is isolated from the residue by silica gel column chromatography, eluting with a mixture of EtOAc and hexanes.

Compound 43: 4-amino-1-((2R,3R,4R,5R)-3-chloro-4-hydroxy-5-(hydroxymethyl)-5-((methylthio)methyl)tetrahydrofuran-2-yl)pyrimidin-2(1H)-one Compound 42 (1 mmol) is dissolved in DCM (10 mL). To this solution is added AgNO$_3$ (2 eq) and collidine (1 eq) and MMTrCl (4 eq). The reaction stirred until the reaction is determined to be complete. The reaction is filtered through celite, washing forward with DCM. The filtrate is washed with 1M citric acid, half-saturated brine and 5% NaHCO$_3$. The organic phase is then dried over Na$_2$SO$_4$. The drying agent is removed by filtration and the filtrate is concentrated. The MMTr-protected product is isolated from the residue by silica gel column chromatography, eluting with a mixture of EtOAc and hexanes.

The MMTr-protected product from above (1 mmol) is dissolved in ACN (10 mL) and then DMAP (2 eq), TPSCl (2 eq), and TEA (2 eq) are added. The reaction is stirred at rt until the reaction is determined to be complete. Concentrated aqueous NH$_4$OH (15 mL) is then added to the reaction and stirring is continued at rt until the reaction is determined to be complete. The reaction is concentrated and the product is isolated by silica gel column chromatography, eluting with a mixture of EtOAc and hexanes.

The aminated product from above (1 mmol) is dissolved in an 80% aqueous solution of AcOH. The reaction is stirred until the reaction is determined to be complete. The solvent is removed from the reaction by evaporation and the residue is coevaped twice with toluene. Compound 43 is purified from this residue by silica gel column chromatography using a mixture of MeOH and DCM as the eluent.

Compound 44: 1-((2R,3R,4R,5R)-3-chloro-4-hydroxy-5-(hydroxymethyl)-5-((methylthio)methyl) tetrahydrofuran-2-yl)pyrimidine-2,4(1H,3H)-dione Compound 43 (1 mmol) is dissolved in an 80% aqueous solution of AcOH. The reaction is stirred until the reaction is determined to be complete. The solvent is removed from the reaction by evaporation and the residue is coevaped twice with toluene. Compound 44 is purified from this residue by silica gel column chromatography using a mixture of MeOH and DCM as the eluent.

Nucleoside Triphosphates

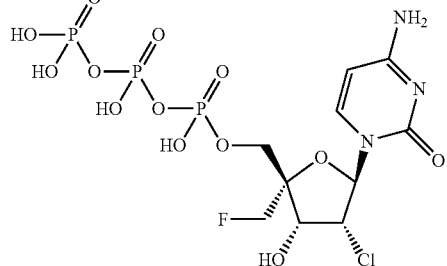
NTP8

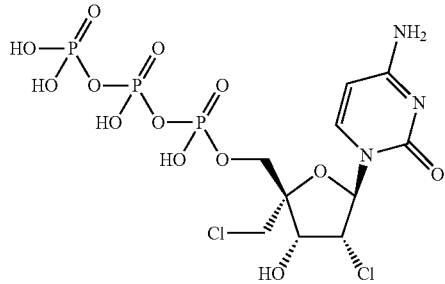
NTP11

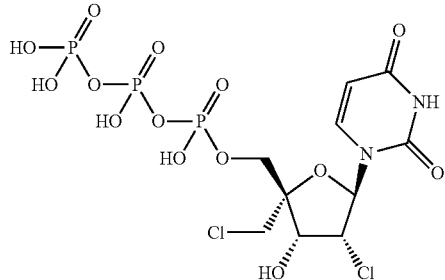
NTP12

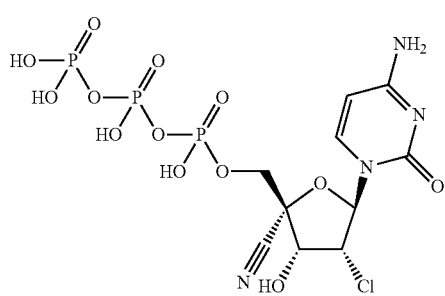
NTP13

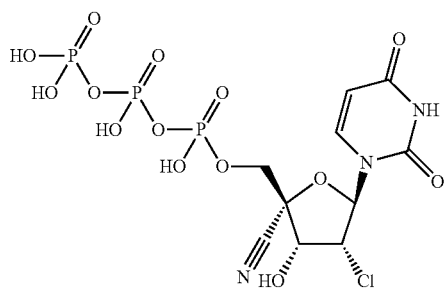
NTP15

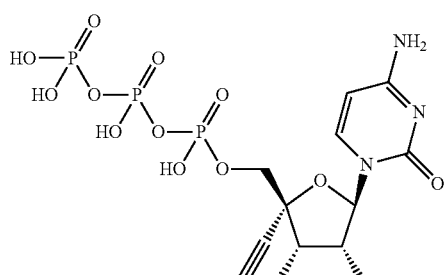
NTP17

NTP9

NTP18
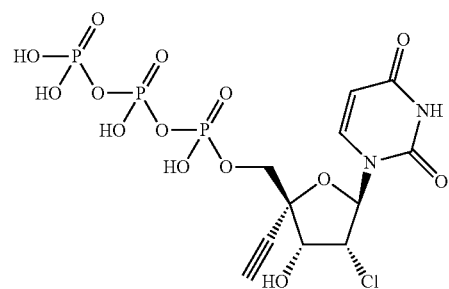
NTP20
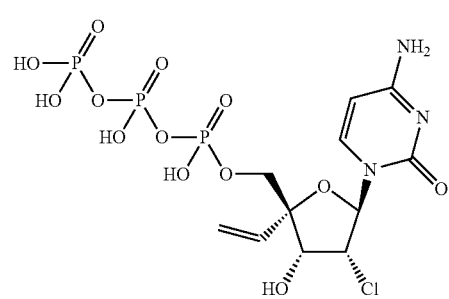
NTP21
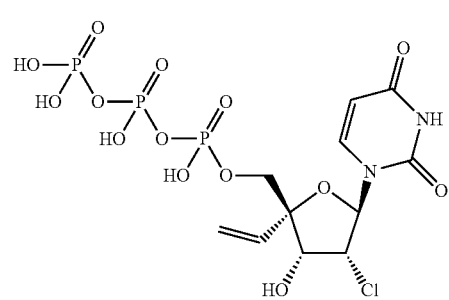
NTP23
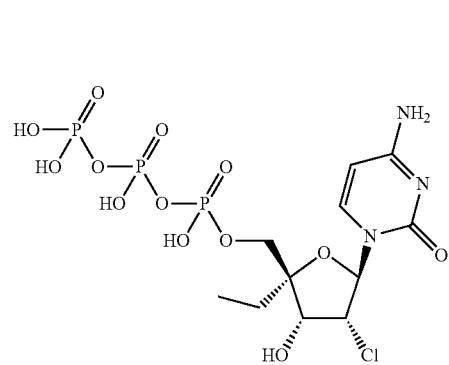
NTP24
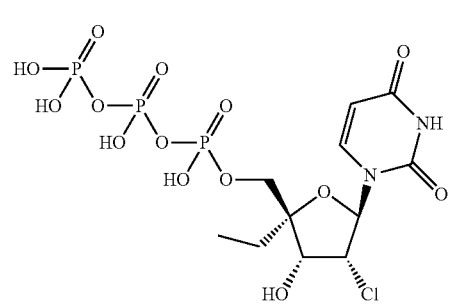
NTP26
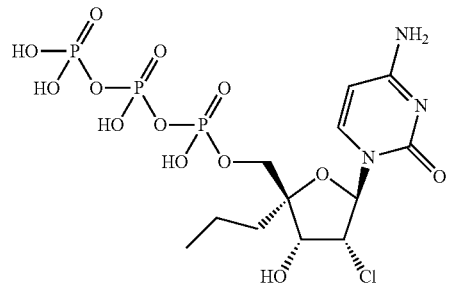
NTP27
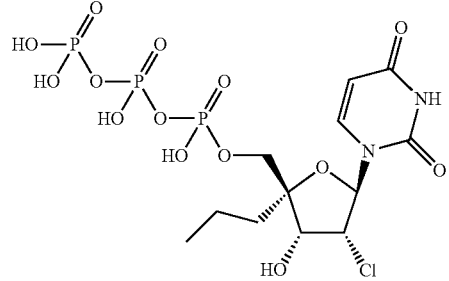
NTP31
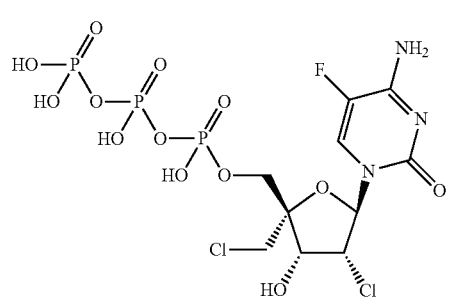
NTP32
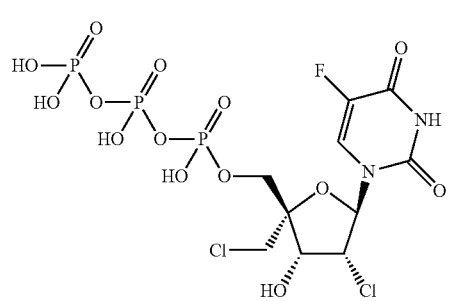
NTP34
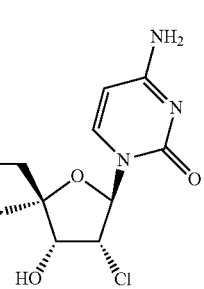

General Synthesis of Nucleoside Triphosphates

NTP35
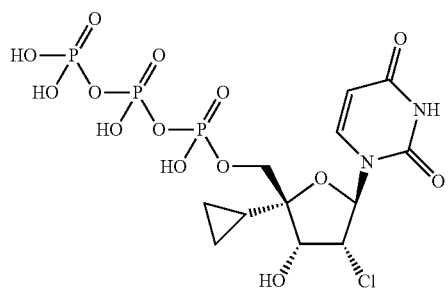

NTP39
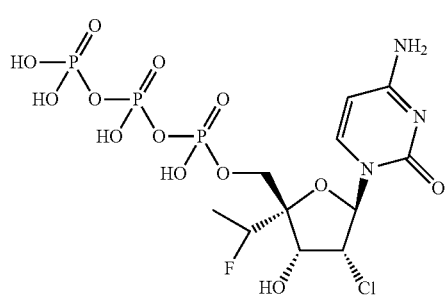

NTP40
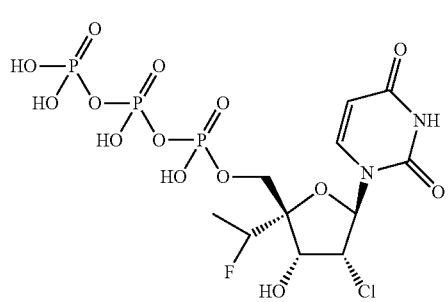

NTP43
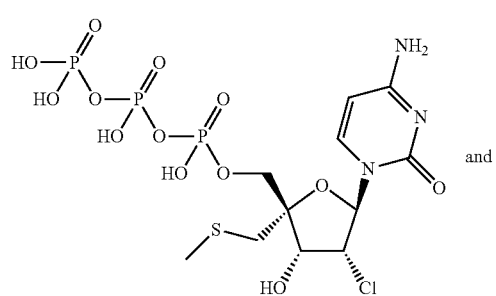

and

NTP44
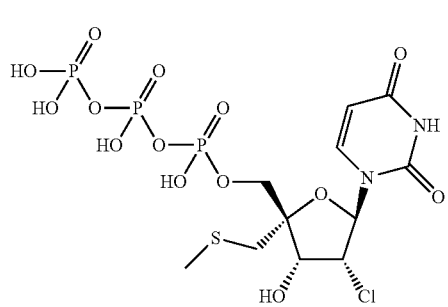

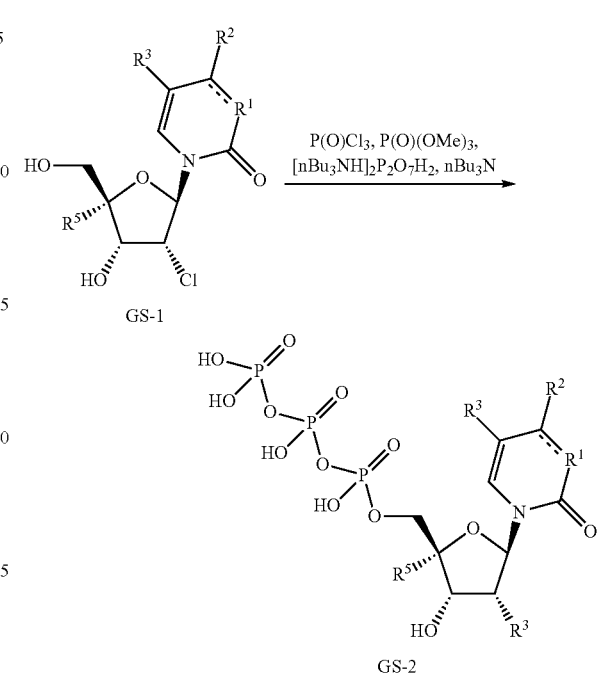

General Procedure

A nucleoside of the general formula GS-1 (1 mmol) is dissolved in P(O)(OMe)$_3$ (10 mL) and cooled in an ice bath. To this solution is added P(O)Cl$_3$ (2 eq). The reaction is allowed to stir in the ice bath until at least 50% conversion is determined to have occurred. A solution of [nBu$_3$]$_2$P$_2$O$_7$H$_2$ (10 eq) in ACN (10 mL) is then added. The reaction is allowed to stir at 0° C. until the reaction is determined to have completed. The reaction is then quenched by the addition of a 1M solution of triethylammonium bicarbonate (5 mL). The reaction is concentrated and the residue is semi-purified by ion exchange column chromatography. This semi-purified material is further purified by reverse phase C18 column chromatography using 0.1% TEA as a modifier to yield the nucleoside triphosphate of the general formula GS-2 as the tetra-TEA salt.

General Synthesis of Acyclic Phosphoramidate Prodrugs

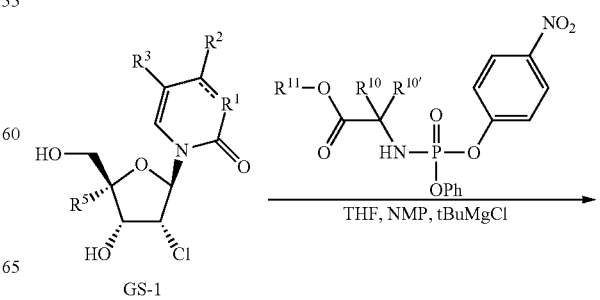

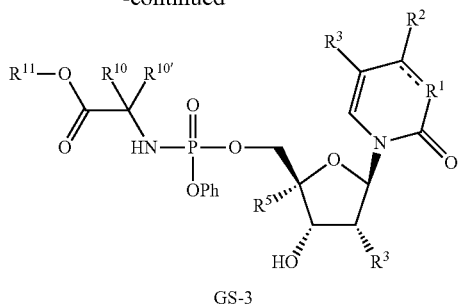

GS-3

General Procedure

A nucleoside of the general formula GS-1 (1 mmol) is dissolved in a 9:1 mixture of THF:NMP (10 mL). This solution is cooled to −78° C. and a 1M solution of tBuMgCl in THF (2 eq) is added. This solution is stirred for 30 min at −78° C. and then at 0° C. for 1 hr. To this solution is added a solution of the para-nitrophenol phosphoramidate (1.1 eq) in THF (5 mL). The resulting reaction is allowed to stir until it is determined to have completed. The reaction is quenched with a saturated aqueous solution of $NH_4Cl$ and diluted with EtOAc. The layers are separated and the organic phase is further extracted with water and brine. The organic phase is dried over $Na_2SO_4$, the drying agent is removed by vacuum filtration and the filtrate is concentrated. Purification of this concentrate by silica gel column chromatography yields the nucleoside prodrug of the general formula GS-3.

General Synthesis of Acyclic Phosphate Prodrugs

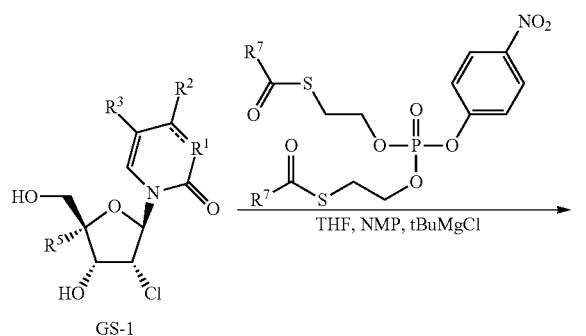

GS-4

General Procedure

A nucleoside of the general formula GS-1 (1 mmol) is dissolved in a 9:1 mixture of THF:NMP (10 mL). This solution is cooled to −78° C. and a 1M solution of tBuMgCl in THF (2 eq) is added. This solution is stirred for 30 min at −78° C. and then at 0° C. for 1 hr. To this solution is added a solution of the para-nitrophenol phosphate ester (1.1 eq) in THF (5 mL). The resulting reaction is allowed to stir until it is determined to have completed. The reaction is quenched with a saturated aqueous solution of $NH_4Cl$ and diluted with EtOAc. The layers are separated and the organic phase is further extracted with water and brine. The organic phase is dried over $Na_2SO_4$, the drying agent is removed by vacuum filtration and the filtrate is concentrated. Purification of this concentrate by silica gel column chromatography yields the nucleoside prodrug of the general formula GS-4.

General Synthesis of Cyclic Phosphoramidate Prodrugs

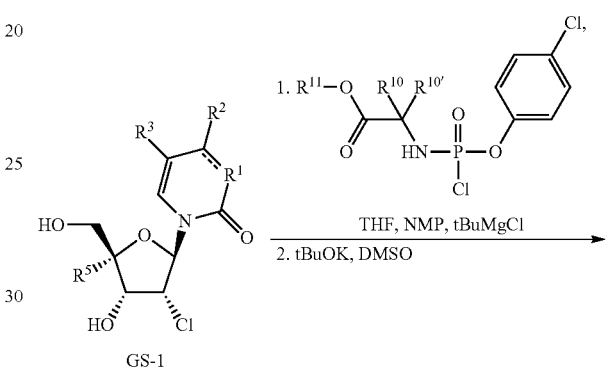

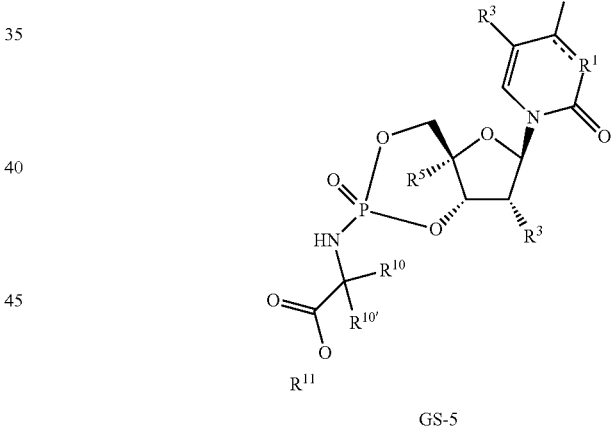

GS-5

General Procedure

A nucleoside of the general formula GS-1 (1 mmol) is dissolved in a 9:1 mixture of THF:NMP (10 mL). This solution is cooled to −78° C. and a 1M solution of tBuMgCl in THF (2 eq) is added. This solution is stirred for 30 min at −78° C. and then at 0° C. for 1 hr. To this solution is added a solution of the chlorophosphoramidate (1.1 eq) in THF (5 mL). The resulting reaction is allowed to stir until it is determined to have completed. The reaction is quenched with a saturated aqueous solution of $NH_4Cl$ and diluted with EtOAc. The layers are separated and the organic phase is further extracted with water and brine. The organic phase is dried over $Na_2SO_4$, the drying agent is removed by vacuum filtration and the filtrate is concentrated. Purification of this concentrate by silica gel column chromatography yields the acyclic phosphoramidate intermediate.

The above acyclic phosphoramidate intermediate (1 mmol) is dissolved in DMSO. To this solution is added tBuOK (leg). The reaction is stirred until it is determined to be complete. The reaction is cooled to 0° C. and quenched by the addition of 1N HCl (1 eq of HCl). The resulting mixture is concentrated. Purification of this concentrate by silica gel column chromatography yields the nucleoside prodrug of the general formula GS-5.

General Synthesis of Cyclic Phosphate Prodrugs

The above acyclic para-nitrophenol phosphate ester intermediate (1 mmol) is dissolved in DMSO. To this solution is added tBuOK (1 eq). The reaction is stirred until it is determined to be complete. The reaction is cooled to 0° C. and quenched by the addition of 1N HCl (1 eq of HCl). The resulting mixture is concentrated. Purification of this concentrate by silica gel column chromatography yields the nucleoside prodrug of the general formula GS-5.

General Synthesis of Ester, Carbamate, Carbonate Prodrugs ($R^2$=$NH_2$)

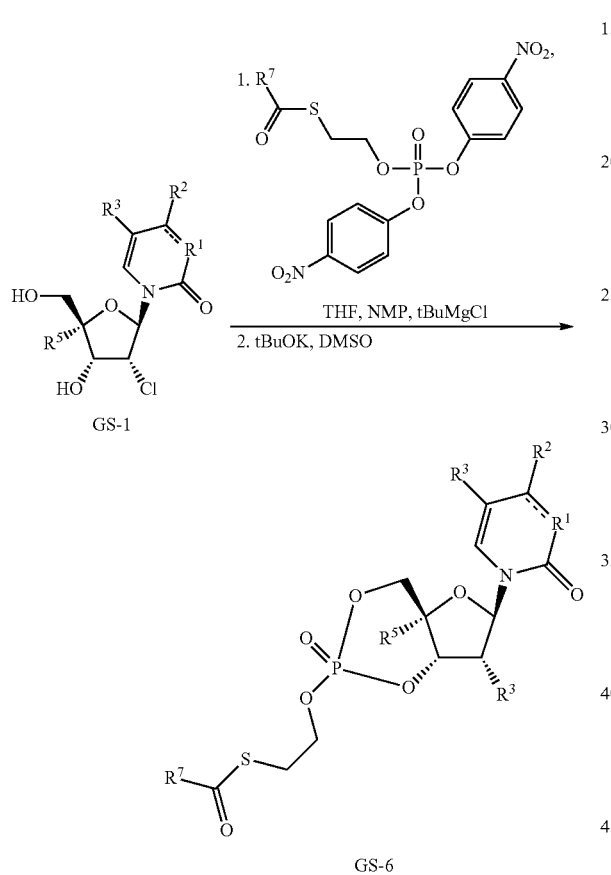

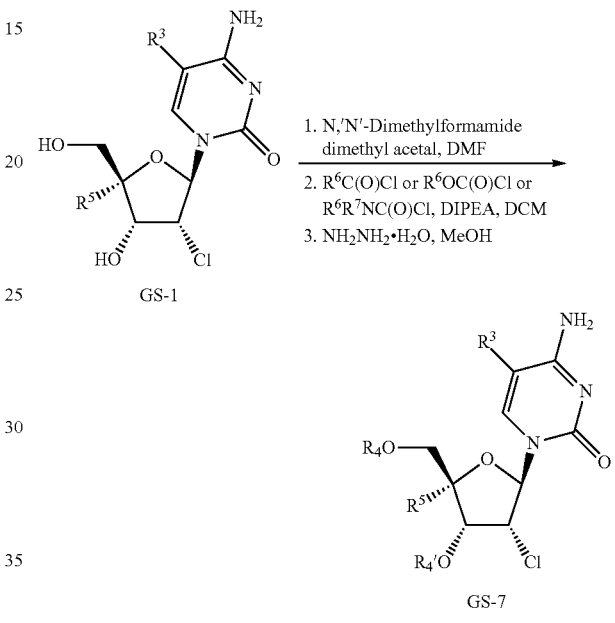

General Procedure

A nucleoside of the general formula GS-1 (1 mmol) is dissolved in a 9:1 mixture of THF:NMP (10 mL). This solution is cooled to −78° C. and a 1M solution of tBuMgCl in THF (2 eq) is added. This solution is stirred for 30 min at −78° C. and then at 0° C. for 1 hr. To this solution is added a solution of the bis para-nitrophenol phosphate ester (1.1 eq) in THF (5 mL). The resulting reaction is allowed to stir until it is determined to have completed. The reaction is quenched with a saturated aqueous solution of $NH_4Cl$ and diluted with EtOAc. The layers are separated and the organic phase is further extracted with water and brine. The organic phase is dried over $Na_2SO_4$, the drying agent is removed by vacuum filtration and the filtrate is concentrated. Purification of this concentrate by silica gel column chromatography yields the acyclic para-nitrophenol phosphate ester intermediate.

General Procedure

A nucleoside of the general formula GS-1 (1 mmol) is dissolved in DMF (10 mL). To this solution is added N',N'-dimethylformamide dimethyl acetal. The reaction is stirred overnight. The reaction is concentrated and the resulting amidine protected product is used as is in the next reaction.

To the above amidine protected product (1 mmol) is dissolved in DCM (10 mL). To this solution is added DIPEA (2.2 eq). To this solution is added either an acid chloride (2 eq), a chloroformate (2 eq) or a carbamic chloride (2 eq), in order to access the bis-ester, bis-carbonate, or the bis-carbamate, respectively. Once the reaction is determined to have completed the reaction is quenched by the addition of a saturated solution of $NaHCO_3$. The mixture is diluted with EtOAc and the layers are separated. The organic layer is washed with water and brine and then dried over $Na_2SO_4$. The drying agent is removed by filtration and the filtrate is concentrated. The resulting crude product is taken on into the next reaction.

The above described crude bis-ester, bis-carbonate, or bis-carbamate (1 mmol) is dissolved in MeOH (10 mL). To this solution is added hydrazine hydrate (10 eq). The reaction is stirred until complete and the reaction is concentrated. Purification of this concentrate by silica gel column chromatography yields the nucleoside prodrug of the general formula GS-7.

General Synthesis of Ester, Carbamate, Carbonate Prodrugs ($R^2$=OH)

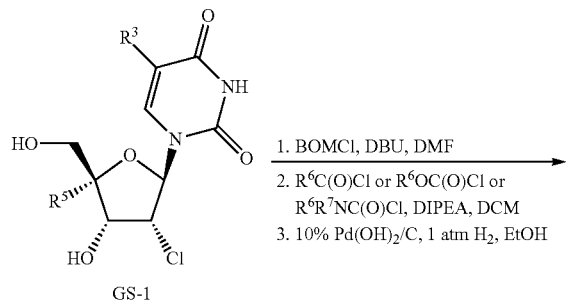

GS-1

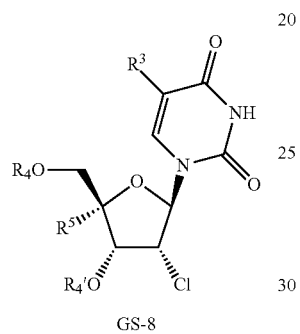

GS-8

General Procedure

A nucleoside of the general formula GS-1 (1 mmol) is dissolved in DMF (10 mL). To this solution is added DBU (1.2 eq) and BOMCl (1.1 eq). The reaction is stirred until complete. The reaction is quenched by the addition of MeOH and resulting mixture is concentrated. Purification of this concentrate by silica gel column chromatography yields the BOM-protected nucleoside.

The above described BOM-protected nucleoside (1 mmol) is dissolved in DCM (10 mL). To this solution is added DIPEA (2.2 eq). To this solution is added either an acid chloride (2 eq), a chloroformate (2 eq) or a carbamic chloride (2 eq), in order to access the bis-ester, bis-carbonate, or the bis-carbamate, respectively. Once the reaction is determined to have completed the reaction is quenched by the addition of a saturated solution of $NaHCO_3$. The mixture is diluted with EtOAc and the layers are separated. The organic layer is washed with water and brine and then dried over $Na_2SO_4$. The drying agent is removed by filtration and the filtrate is concentrated. Purification of this concentrate by silica gel column chromatography yields the BOM-protected bis-ester, bis-carbonate or bis-carbamate.

The above described BOM-protected bis-ester, bis-carbonate or bis-carbamate (1 mmol) is dissolved in EtOH (10 mL). To this solution is added 10% Pd(OH)2/C. The atmosphere of the reaction vessel is exchanged for H2 and the reaction is stirred until it is complete. The reaction is filtered through Celite and the filtrate is concentrated. Purification of this concentrate by silica gel column chromatography yields the nucleoside prodrug of the general formula GS-8.

Synthesis Of Examples 1 and 2

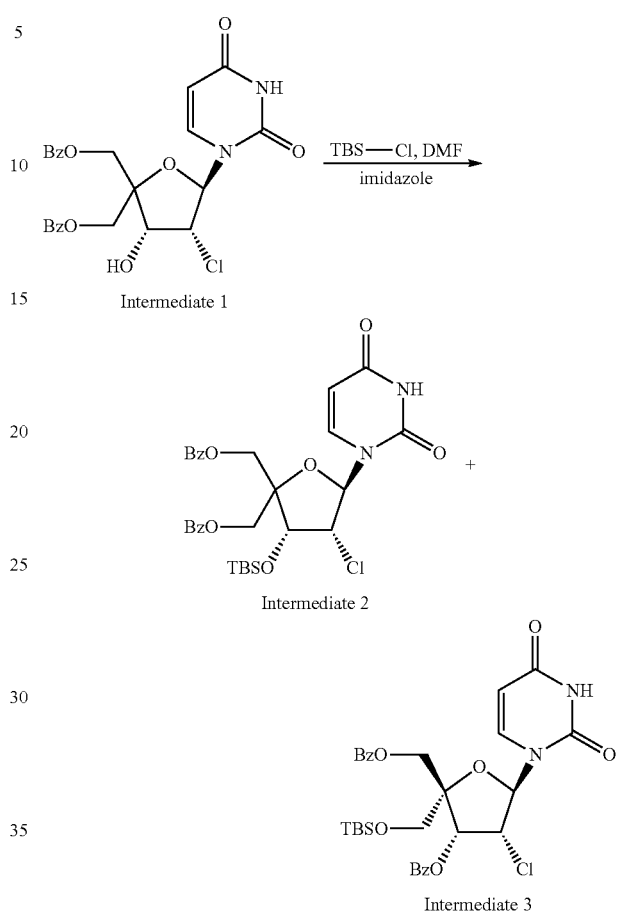

Intermediate 2—((3R,4R,5R)-3-((tert-butyldimethylsilyl)oxy)-4-chloro-5-(2,4-dioxo-3,4-dihydropyrimidin-1(2H)-yl)tetrahydrofuran-2,2-diyl)bis(methylene)dibenzoate Intermediate 1 (*Collect. Czech. Chem. Commun.* 1997, 62, pp. 957-970) (590 mg, 1.18 mmol) was dissolved in anhydrous N,N-dimethylformamide (5 mL). tert-Butyldimethylsilyl chloride (889 mg, 5.9 mmol) and imidazole (804 mg, 11.8 mmol) were added to the reaction which was then stirred at 50° C. for 16 hrs. HPLC showed ~16% conversion. The reaction was warmed to 65° C. and stirred for 3 hrs. HPLC showed ~17% conversion. The reaction was warmed to 80° C. and stirred for 2 hrs. HPLC showed ~42% conversion. More tert-butyldimethylsilyl chloride (889 mg, 5.9 mmol) and imidazole (804 mg, 11.8 mmol) were added. The reaction was stirred at 80° C. for 48 hrs.

HPLC showed ~89% conversion. The reaction was cooled to room temperature and diluted with ethyl acetate (40 mL). The mixture was washed with saturated aqueous sodium bicarbonate solution (20 mL) and then brine (20 mL). The organic was dried over anhydrous sodium sulfate and concentrated under reduced pressure. The crude residue was purified via $SiO_2$ column chromatography (40 g $SiO_2$ Combiflash HP Gold Column 0-40% ethyl acetate/hexanes) to yield a mixture of Intermediates 2 and 3 (655 mg mixture of isomers, 90%).

¹H NMR (400 MHz, CDCl₃) δ 8.17-7.96 (m, 5H), 7.69-7.34 (m, 6H), 6.42-6.34 (m, 1H), 6.01 (m, 1H), 5.65 (m, 1H), 5.00 (dd, J=12.8 Hz, 1H), 4.85-4.71 (m, 2H), 4.65-4.47 (m, 3H), 4.05-3.97 (m, 1H), 3.90-3.80 (m, 1H), 0.97 (s, 9H), 0.78 (s, 9H), 0.19 (s, 3H), 0.13 (s, 3H), –0.01 (s, 3H), –0.15 (s, 3H).

MS m/z=614.9 [M+1]

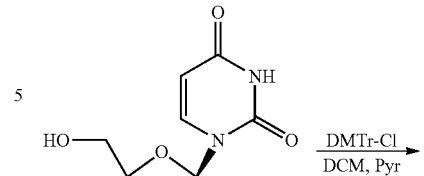

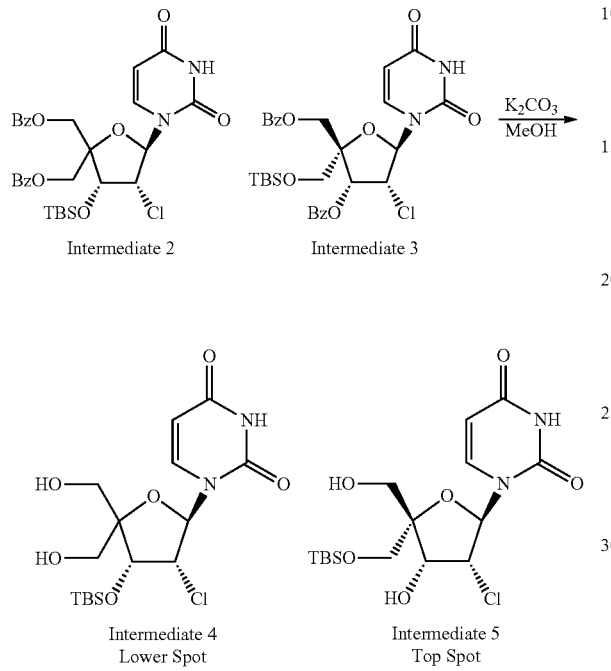

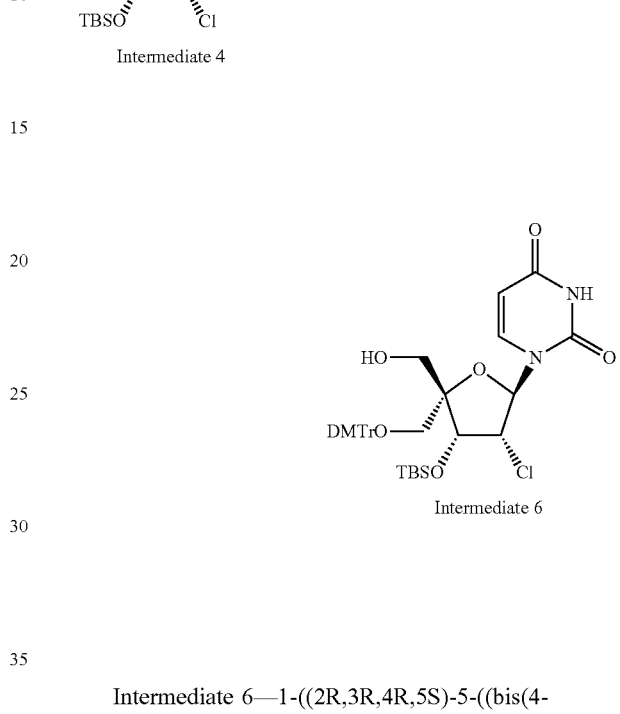

Intermediate 4—1-((2R,3R,4R)-4-((tert-butyldimethylsilyl)oxy)-3-chloro-5,5-bis(hydroxymethyl)tetrahydrofuran-2-yl)pyrimidine-2,4(1H,3H)-dione A mixture of Intermediates 2 and 3 (655 mg, 1.06 mmol) was dissolved in methanol (10 mL). Potassium carbonate (352 mg, 2.13 mmol) was added to the reaction and stirred for 12 hrs.

The reaction mixture was diluted with ethyl acetate (50 mL) and washed with saturated aqueous sodium bicarbonate solution (20 mL) and then brine (20 mL). The organic was dried over anhydrous sodium sulfate and concentrated under reduced pressure. The crude residue was purified via SiO₂ column chromatography (40 g SiO₂ Combiflash HP Gold Column 0-65-90% ethyl acetate/hexanes) to afford Intermediates 4 and 5 (200 mg of Intermediate 4 (lower spot) and 135 mg of Intermediate 5 (top spot), 78%).

Intermediate 4:

¹H NMR (400 MHz, CDCl₃) δ 8.32 (s, 1H), 7.33 (d, J=8.1 Hz, 1H), 5.77 (dd, J=8.1, 2.3 Hz, 1H), 5.71 (d, J=7.4 Hz, 1H), 4.92 (dd, J=7.4, 6.5 Hz, 1H), 4.68 (d, J=6.5 Hz, 1H), 3.85 (ddd, J=29.3, 12.1, 2.7 Hz, 2H), 3.62 (ddd, J=12.3, 9.0, 5.6 Hz, 2H), 3.01 (dd, J=8.7, 3.0 Hz, 1H), 2.35 (dd, J=9.8, 3.8 Hz, 1H), 0.96 (s, 9H), 0.20 (s, 3H), 0.16 (s, 3H).

MS m/z=406.9 [M+1], 405.1 [M–1]

Intermediate 6—1-((2R,3R,4R,5S)-5-((bis(4-methoxyphenyl)(phenyl)methoxy)methyl)-4-((tert-butyldimethylsilyl)oxy)-3-chloro-5-(hydroxymethyl)tetrahydrofuran-2-yl)pyrimidine-2,4(1H,3H)-dione Intermediate 4 (120 mg, 0.29 mmol) was dissolved in anhydrous dichloromethane (5 mL). Anhydrous pyridine (1 mL) was added to the reaction which was then cooled in an ice bath and stirred under atmosphere nitrogen. 4,4'-Dimethoxytrityl chloride (120 mg, 0.35 mmol) was added to the reaction in one portion. Reaction was stirred for 2 hrs. More 4,4'-dimethoxytrityl chloride (120 mg, 0.35 mmol) was added and stirred for 2 hrs. Methanol (2 mL) was added to stop the reaction which was then concentrated under reduced pressure. Residue was dissolved with ethyl acetate (40 mL) and washed with saturated aqueous sodium bicarbonate solution (20 mL) and then brine (20 mL). The organic was dried over anhydrous sodium sulfate and concentrated under reduced pressure. The crude was purified via SiO₂ column chromatography (4 g SiO₂ Combiflash HP Gold Column 0-40% ethyl acetate/hexanes) to afford Intermediate 6 (190 mg, 92%).

¹H NMR (400 MHz, DMSO-d₆) δ 11.49 (s, 1H), 7.86 (d, J=8.2 Hz, 1H), 7.41-7.34 (m, 2H), 7.31-7.15 (m, 7H), 6.85 (dd, J=9.0, 2.2 Hz, 4H), 6.04 (d, J=8.1 Hz, 1H), 5.77 (d, J=8.1 Hz, 1H), 5.29 (m, 1H), 4.72 (dd, J=8.1, 5.4 Hz, 1H), 4.42 (d, J=5.4 Hz, 1H), 3.88 (dd, J=11.5, 4.8 Hz, 1H), 3.71 (s, 6H), 3.52 (dd, J=11.4, 5.4 Hz, 1H), 3.44 (d, J=10.6 Hz, 1H), 2.83 (d, J=10.6 Hz, 1H), 0.68 (s, 9H), –0.01 (s, 3H), –0.29 (s, 3H).

MS m/z=707.4 [M–1], 731.2 [M+Na]

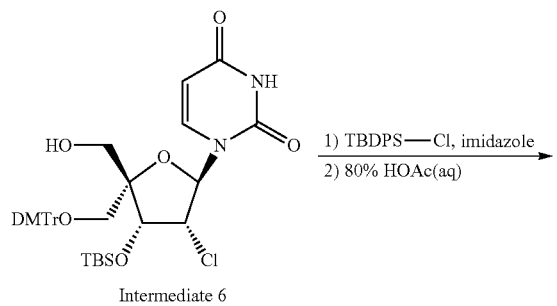

Intermediate 6

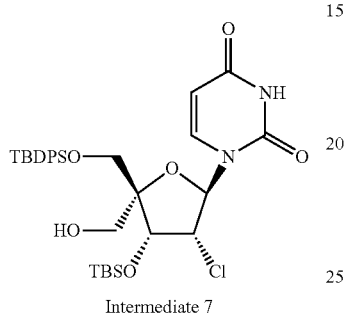

Intermediate 7

Intermediate 7—1-((2R,3R,4R,5R)-4-((tert-butyldimethylsilyl)oxy)-5-(((tert-butyldiphenylsilyl)oxy)methyl)-3-chloro-5-(hydroxymethyl)tetrahydrofuran-2-yl)pyrimidine-2,4(1H,3H)-dione Intermediate 6 (180 mg, 0.254 mmol) was dissolved in anhydrous N,N-dimethylformamide (5 mL). Imidazole (138 mg, 2.03 mmol) and tert-butyldiphenylsilyl chloride (260 uL, 1.02 mmol) were added. Reaction was stirred at 50° C. for 16 hrs.

More imidazole (140 mg, 2.03 mmol) and tert-butyldiphenylsilyl chloride (260 uL, 1.02 mmol) were added. Reaction was stirred at 50° C. for 8 hrs. More imidazole (140 mg, 2.03 mmol) and tert-butyldiphenylsilyl chloride (260 uL, 1.02 mmol) were added. Reaction was stirred at 50° C. for 16 hrs.

HPLC showed ~94% conversion. Reaction was cooled to room temperature, diluted with ethyl acetate (40 mL) and washed with brine (20 mL) three times. The organic was dried over anhydrous sodium sulfate and concentrated under reduced pressure. The crude was purified via SiO$_2$ column chromatography (4 g SiO$_2$ Combiflash HP Gold Column 0-20-50% ethyl acetate/hexanes) to afford title compound (205 mg, 85%) as colorless oil.

Material was dissolved in 80% v/v acetic acid aqueous solution (10 mL) and stirred for 4 hrs. Reaction was diluted with ethyl acetate (40 mL) and washed with brine (20 mL) three times. Organic was then washed with saturated aqueous sodium bicarbonate solution (20 mL) twice to give pH of 8. The organic was dried over anhydrous sodium sulfate and concentrated under reduced pressure. The crude was purified via SiO$_2$ column chromatography (4 g SiO$_2$ Combiflash HP Gold Column 0-35% ethyl acetate/hexanes) to afford Intermediate 7 (106 mg, 59% over 2 steps).

$^1$H NMR (400 MHz, CDCl$_3$) δ 8.79 (s, 1H), 7.68-7.57 (m, 4H), 7.54-7.37 (m, 6H), 6.23 (d, J=7.9 Hz, 1H), 5.54-5.45 (m, 1H), 4.49-4.41 (m, 1H), 4.37 (dd, J=7.9, 5.8 Hz, 1H), 3.96 (d, J=11.4 Hz, 1H), 3.86 (d, J=12.3 Hz, 1H), 3.74 (d, J=11.4 Hz, 1H), 3.56 (d, J=12.3 Hz, 1H), 1.11 (s, 9H), 0.93 (s, 9H), 0.16 (s, 3H), 0.03 (s, 3H).

MS m/z=643.5 [M−1], 667.4 [M+Na]

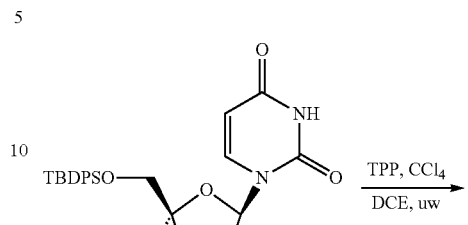

Intermediate 7

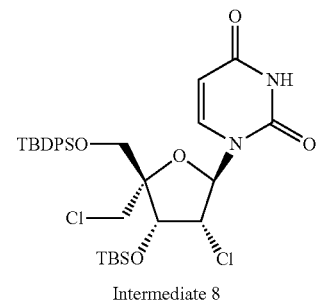

Intermediate 8

Intermediate 8—1-((2R,3R,4R,5R)-4-((tert-butyldimethylsilyl)oxy)-5-(((tert-butyldiphenylsilyl)oxy)methyl)-3-chloro-5-(chloromethyl)tetrahydrofuran-2-yl)pyrimidine-2,4(1H,3H)-dione Intermediate 7 (104 mg, 0.164 mmol) was dissolved in 1,2-dichloroethane (2 mL) and stirred under argon gas. Carbon tetrachloride (32 uL, 0.328 mmol) and triphenylphosphine (86 mg, 0.328 mmol) were added to reaction which was then microwaved at 130° C. for 40 mins. The reaction was concentrated under reduced pressure. The crude was purified via SiO$_2$ column chromatography (4 g SiO$_2$ Combiflash HP Gold Column 0-20% ethyl acetate/hexanes) to afford Intermediate 8 (76 mg, 70%).

$^1$H NMR (400 MHz, CDCl$_3$) δ 8.45 (d, J=2.4 Hz, 1H), 7.72-7.57 (m, 4H), 7.54-7.34 (m, 7H), 6.15 (d, J=7.6 Hz, 1H), 5.54 (dd, J=8.2, 2.2 Hz, 1H), 4.45-4.34 (m, 2H), 4.00 (d, J=11.2 Hz, 1H), 3.91-3.76 (m, 2H), 3.58 (d, J=12.1 Hz, 1H), 1.12 (s, 9H), 0.94 (s, 9H), 0.16 (s, 3H), 0.04 (s, 3H).

MS m/z=661.5 [M−1]

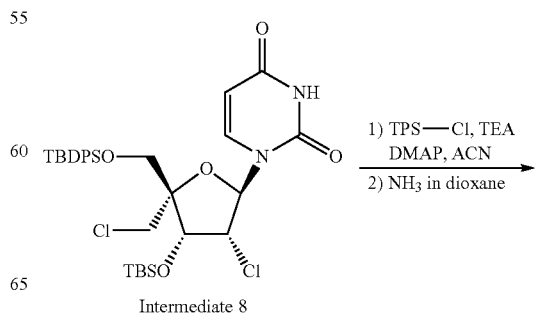

Intermediate 8

81

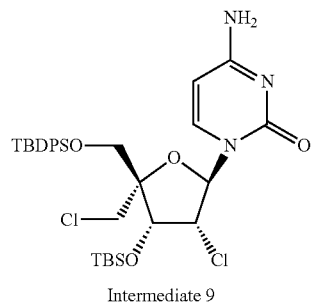

Intermediate 9

Intermediate 9—4-amino-1-((2R,3R,4R,5R)-4-((tert-butyldimethylsilyl)oxy)-5-(((tert-butyldiphenylsilyl)oxy)methyl)-3-chloro-5-(chloromethyl)tetrahydrofuran-2-yl)pyrimidin-2(1H)-one Intermediate 8 (74 mg, 0.111 mmol) was dissolved in anhydrous acetonitrile (5 mL). Triethylamine (31 uL, 0.223 mmol) and 2,4,6-triisopropylbenzenesulfonyl chloride (68 mg, 0.223 mmol) were added to the reaction. 4-(Dimethylamino)pyridine (27 mg, 0.223 mmol) was added to the reaction and stirred at room temperature for 16 hrs.

0.5M ammonia in 1,4-dioxane (5 mL) was added to the reaction and stirred for 2 hrs. The mixture was concentrated under reduced pressure. The residue was dissolved in ethyl acetate (40 mL) and washed with saturated aqueous sodium bicarbonate solution (10 mL) and brine (10 mL). The organic was dried over anhydrous sodium sulfate and concentrated under reduced pressure. The crude was purified via SiO$_2$ column chromatography (4 g SiO$_2$ Combiflash HP Gold Column 0-80% ethyl acetate/hexanes) to afford Intermediate 9 (57 mg, 78%).

MS m/z=662.0 [M+1]

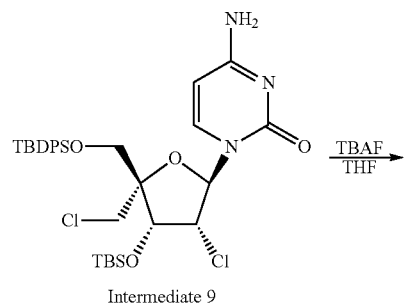

Intermediate 9

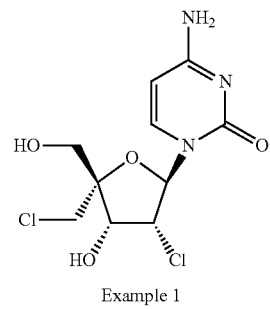

Example 1

82

EXAMPLE 1

4-amino-1-((2R,3R,4R,5R)-3-chloro-5-(chloromethyl)-4-hydroxy-5-(hydroxymethyl)tetrahydrofuran-2-yl)pyrimidin-2(1H)-one Intermediate 9 (50 mg, 0.075 mmol) was dissolved in anhydrous tetrahydrofuran (5 mL). Tetrabutylammonium fluoride trihydrate (119 mg, 0.377 mmol) was added, and the reaction was stirred at room temperature for 30 mins. HPLC showed reaction was completed. Trifluoroacetic acid (29 uL, 0.377 mmol) was added to give slightly acidic solution. The mixture was concentrated under reduced pressure and purified with prep HPLC (Phenomenex Gemini C$_{18}$ column, 0-100% acetonitrile/water). Fractions were combined and concentrated under reduced pressure. Material was re-purified with prep-HPLC (Phenomenex Gemini C$_{18}$ column, 0-50% acetonitrile/water with 0.1% trifluoroacetic acid as modifier). Fractions were combined and concentrated under reduced pressure. Material was dissolved in water (1 mL) and small amount of saturated aqueous sodium bicarbonate solution was then added to give pH of 8. Solution was loaded onto a pre-packed C$_{18}$ column equilibrated with water. Column was washed with water (5 column volumes) and then eluted with 70% acetonitrile in water. Fractions were combined and freeze-dried to afford Example 1 (9.4 mg, 40%).

$^1$H NMR (400 MHz, D$_2$O) δ 7.61 (d, J=7.7 Hz, 1H), 6.11 (d, J=8.6 Hz, 1H), 5.97 (d, J=7.6 Hz, 1H), 4.72 (dd, J=8.7, 5.3 Hz, 1H), 4.39 (d, J=5.2 Hz, 1H), 3.86-3.66 (m, 4H).

MS m/z=309.8 [M+1]

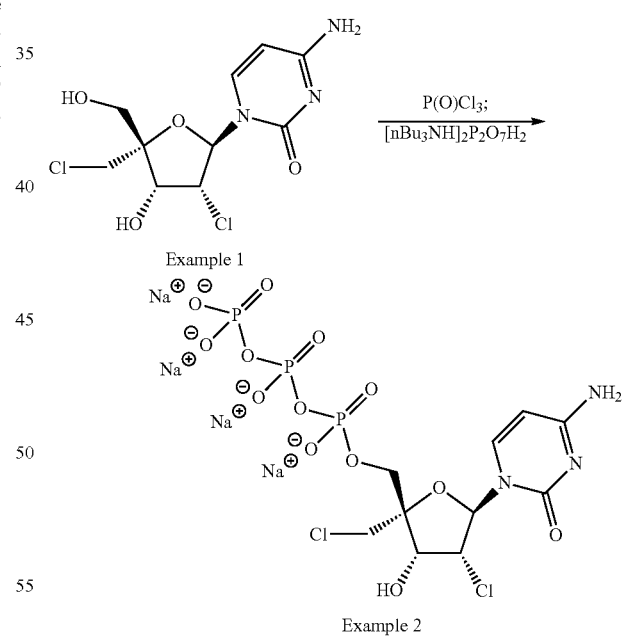

EXAMPLE 2

((2R,3R,4R,5R)-5-(4-amino-2-oxopyrimidin-1(2H)-yl)-4-chloro-2-(chloromethyl)-3-hydroxytetrahydrofuran-2-yl)methyl tetrahydrogen triphosphate To a solution of Example 1 (4.08 mg, 0.013 mmol) and NaHCO$_3$ (7 mg, 0.083 mmol) in PO(OMe)$_3$ (0.3 mL) at 0°

C. was added POCl$_3$ (31 mg, 0.202 mmol). The reaction mixture was stirred at 0° C. for 4 h, at which point ion-exchange HPLC showed approximately 80% conversion. A solution of pyrophosphate tributylamine salts (250 mg) in CH$_3$CN (0.5 mL) was added, followed by tributylamine (125 mg, 0.67 mmol). The reaction mixture was stirred at 0° C. for 0.5 h, and ion-exchange HPLC showed the reaction was completed. The reaction was quenched with triethylammonium bicarbonate buffer (1 M, 8 mL). The reaction mixture was stirred at RT for 0.5 h, then concentrated and co-evaporated with water twice. The residue was dissolved in H$_2$O (5 mL) and loaded to a ion-exchange column, eluted with H$_2$O, then 5-35% triethylammonium bicarbonate buffer (1M)-H$_2$O. The product fractions were combined, concentrated and co-evaporated with H$_2$O to give about 28 mg of material. The material was dissolved in 2 mL of H$_2$O and treated with NaHCO$_3$ (40 mg). The resulting mixture was purified with C-18 column, eluted with H$_2$O, and the fractions containing product were combined and concentrated under reduced pressure to afford Example 2 as the tetrasodium salt (3.0 mg, 35.7%).

$^1$H NMR (400 MHz, D$_2$O): δ 7.77 (d, J=7.6 Hz, 1H), 6.24 (d, J=6.8 Hz, 1H), 6.07 (d, J=7.6 Hz, 1H), 4.6-4.7 (m, 2H), 4.1-4.25 (m, 2H), 3.89 (d, J=12.8 Hz, 1H), 3.79 (d, J=12.0 Hz, 1H).

$^{31}$P NMR (400 MHz, D$_2$O): δ −8.10 (d, J=50.8 Hz), −13.76 (d, J=46 Hz), −23.97 (t, J=49.4 Hz).

MS m/z=548.4 [M−1], 549.9 [M+1]

Methods for Determining EC$_{50}$'s for the Inhibition of RSV in Cells and IC$_{50}$'s for the inhibition of RSV viral polymerase The following assays could be used to determine the EC$_{50}$ of the described nucleosides for the inhibition of RSV in cell culture and to determine the IC50 of the described nucleoside triphosphates for the inhibition of the RSV viral polymerase.

RSV Pol IC$_{50}$ determination

Transcription reactions contained 5 μg of crude RSV RNP complexes in 30 μL of reaction buffer [50 mM TRIS-acetate (pH 8.0), 120 mM potassium acetate, 5% glycerol, 4.5 mM MgCl$_2$, 3 mM DTT, 2 mM ethyleneglycol-bis(2-aminoethylether)-tetraacetic acid (EGTA), 50 μg/mL BSA, 2.5 U RNasin (Promega), ATP, GTP, UTP, CTP and 1.5 uCi [α-$^{32}$P] NTP (3000 Ci/mmol)]. The radiolabled nucleotide used in the transcription assay was selected to match the nucleotide analog being evaluated for inhibition of RSV RNP transcription. Cold, competitive NTP was added at a final concentration of one-half its K$_m$ (ATP=20 μM, GTP=12.5 μM, UTP=6 μM and CTP=2 μM). The three remaining nucleotides were added at a final concentration of 100 μM.

To determine whether nucleotide analogs inhibited RSV RNP transcription, compounds were added using a 6 step serial dilution in 5-fold increments. Following a 90 minute incubation at 30° C., the RNP reactions were stopped with 350 μL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2M formaldehyde. The agarose gel was dried and exposed to a Storm phosphorimager screen and developed using a Storm phosphorimager (GE Healthcare). The concentration of compound that reduced total radiolabled transcripts by 50% (IC$_{50}$) was calculated by non-linear regression analysis of two replicates.

RSV Cell Culture EC$_{50}$ Determination

Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., *Antimicrob Agents Chemother*. 2007, 51(9):3346-53.)

HEp-2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, Md.) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nl per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/ml and 20 uL/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, Wis.) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the EC$_{50}$ value for each compound is determined by non-linear regression as a concentration inhibiting the RSV-induced cytopathic effect by 50%. Various potent anti-RSV tool compounds are used as positive controls for antiviral activity.

The EC$_{50}$ for Example 1 is >50 μM

What is claimed:

1. A compound of Formula I, or a pharmaceutically acceptable salt thereof:

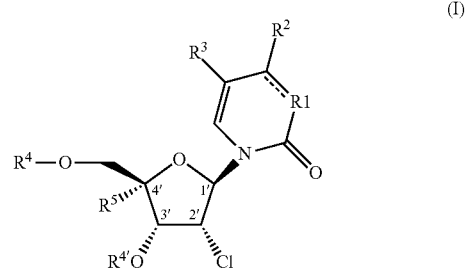

wherein:

$R^1$ is selected from NH and N;

the dashed line (- - - -), in conjunction with the solid line to which it is parallel, represents an optional double bond;

$R^2$ is selected from oxo or $NH_2$, with the proviso that, when $R^2$ is oxo, $R^1$ and the bond represented by the dashed line (- - - -), in conjunction with the solid line to which it is parallel, is a single bond; and with the proviso that, when $R^2$ is $NH_2$, $R_1$ is N and the bond represented by the dashed line (- - - -), in conjunction with the solid line to which it is parallel, is a double bond;

$R^3$ is selected from the group of H, F, $CH_2F$, $CHF_2$, and $CF_3$;

$R^5$ is selected from the group of CN; unsubstituted $C_1$-$C_4$ alkyl; $C_1$-$C_4$ alkyl substituted with 1, 2, or 3 halogens; $C_1$-$C_4$ alkyl substituted with 1 substituent selected from —S—$CH_3$ and —O—$CH_3$; $C_2$-$C_4$ alkenyl; $C_2$-$C_4$ alkynyl; unsubstituted $C_3$-$C_6$ cycloalkyl; and $C_3$-$C_6$ cycloalkyl substituted by 1, 2, or 3 substituents selected from F and $CH_3$;

$R^{4'}$ is selected from the group of H, —C(=O)$R^6$, —C(=O)O$R^6$, and —C(=O)N$R^6R^7$;

$R^4$ is selected from the group of H, —C(=O)$R^6$, —C(=O)O$R^6$, and —C(=O)N$R^6R^7$; or a) $R^4$ is a group of the formula:

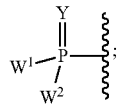

wherein:

each Y is O, S, NR, $^+$N(O)(R), N(OR), $^+$N(O)(OR), or N—$NR_2$; and $W^1$ and $W^2$, when taken together, are —$Y^3$(C($R^y$)$_2$)$_3$$Y^3$—;

or one of $W^1$ or $W^2$ together with $R^{4'}$ is —$Y^3$— and the other of $W^1$ or $W^2$ is Formula Ia;

or $W^1$ and $W^2$ are each, independently, a group of the Formula Ia:

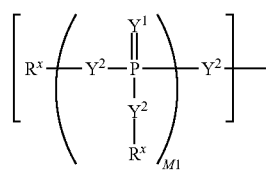

Formula Ia wherein:

each $Y^1$ is, independently, O, S, NR, $^+$N(O)(R), N(OR), $^+$(N)(O)(OR), or N—$NR_2$;

each $Y^2$ is independently a bond, O, $CR_2$, —O—$CR_2$—, NR, $^+$N(O)(R), N(OR), $^+$N(O)(OR), N—$NR_2$, S, S—S, S(O), or S(O)$_2$;

each $Y^3$ is a single bond;

M1 is 0, 1, 2, or 3;

each $R^x$ is independently $R^y$ or the formula:

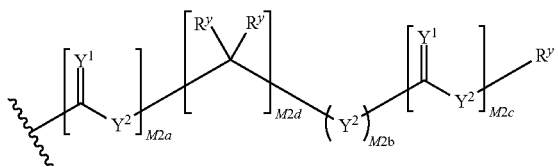

wherein:

each M2a, M2b, and M2c is independently 0 or 1;

M2d is 0, 1, 2, 3, 4, 5, 6, 7, 8, 9, 10, 11 or 12;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —$SO_2NR_2$, —CN, —$N_3$, —$NO_2$, —OR, or $W^3$;

or when taken together, two $R^y$ on the same carbon atom form a carbocyclic ring having 3, 4, 5, 6, or 7 carbon ring atoms;

or when taken together, two $R^y$ on the same carbon atom form along with the carbon atom a heterocycle having 3, 4, 5, 6, or 7 ring atoms wherein one ring atom is selected from O or N and all other ring atoms are carbon;

each R is independently H, ($C_1$-$C_8$) alkyl, ($C_1$-$C_8$) substituted alkyl, ($C_2$-$C_8$)alkenyl, ($C_2$-$C_8$) substituted alkenyl, ($C_2$-$C_8$) alkynyl, ($C_2$-$C_8$) substituted alkynyl, $C_6$-$C_{10}$ aryl, $C_6$-$C_{10}$ substituted aryl, a 3- to 10-membered heterocycle, a substituted 3- to 10-membered heterocycle, a 5- to 12-membered heteroaryl, a substituted 5- to 12-membered heteroaryl, arylalkyl, substituted arylalkyl, heteroarylalkyl, or substituted heteroarylalkyl; and $W^3$ is $W^4$ or $W^5$;

$W^4$ is R, —C($Y^1$)$R^y$, —C($Y^1$)$W^5$, —$SO_2R^y$, or —$SO_2W^5$;

$W^5$ is selected from phenyl, naphthyl, a $C_3$-$C_8$ carbocycle, or a 3- to 10-membered heterocycle, wherein $W^5$ is independently substituted with 0, 1, 2, 3, 4, 5, or 6 $R^y$ groups;

each $R^6$ and $R^7$ is independently H, ($C_1$-$C_8$)alkyl, ($C_2$-$C_8$)alkenyl, ($C_2$-$C_8$)alkynyl, ($C_4$-$C_8$)carbocyclylalkyl, $C_6$-$C_{10}$ aryl, $C_6$-$C_{10}$ substituted aryl, 5- to 10-membered heteroaryl, substituted 5- to 10-membered heteroaryl, —C(=O)($C_1$-$C_8$)alkyl, —S(O)$_n$($C_1$-$C_8$)alkyl or aryl($C_1$-$C_8$)alkyl;

or $R^6$ and $R^7$ taken together with a nitrogen to which they are both attached form a 3- to 7-membered heterocycle wherein any one ring carbon atom of said heterocycle can optionally be replaced with —O—, —S— or —$NR^a$—;

and wherein each ($C_1$-$C_8$)alkyl, ($C_2$-$C_8$)alkenyl, ($C_2$-$C_8$)alkynyl or aryl($C_1$-$C_8$)alkyl of each $R^6$ or $R^7$ is, independently, optionally substituted with one, two, three, or four substituents selected from halo, hydroxy, CN, $N_3$, N($R^a$)$_2$ or O$R^a$; and wherein one, two, or three of the non-terminal carbon atoms of each said ($C_1$-$C_8$)alkyl may be optionally replaced with —O—, —S— or —$NR^a$—; or b) $R^4$ is a group selected from:

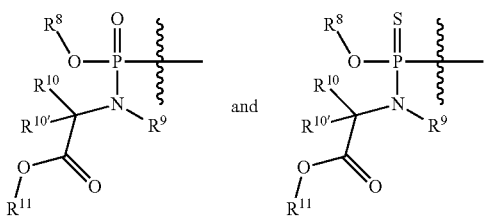

and wherein:

$R^8$ is selected from phenyl, 1-naphthyl, 2-naphthyl,

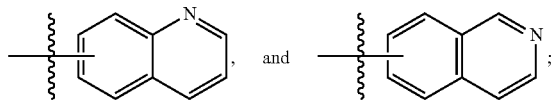

$R^9$ is selected from H and $CH_3$;
$R^{10}$ is selected from H or $C_1$-$C_6$ alkyl;
$R^{10'}$ is selected from H or $C_1$-$C_6$ alkyl;
or $R^{10}$ and $R^{10'}$, together with the carbon atom to which they are bound, form a 3-, 4-, 5-, or 6-membered spirocycle wherein all ring atoms of the spirocycle are carbon;
or $R^{10}$ and $R^{10'}$, together with the carbon atom to which they are bound, form a 3-, 4-, 5-, or 6-membered spirocycle wherein 1 or 2 of the ring atoms of the spirocycle are selected from the group of O, S, and N, and all other ring atoms of the spirocycle are carbon;
$R^{11}$ is selected from H, $C_1$-$C_8$ alkyl, benzyl, $C_3$-$C_6$ cycloalkyl, —$CH_2$—$C_3$-$C_6$ cycloalkyl, —$CH_2CH_2$—S—C(O)—$C_3$-$C_6$ alkyl,

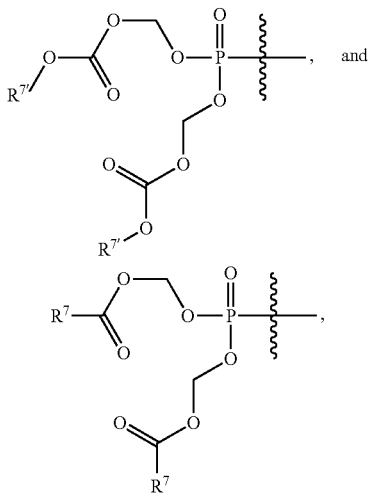

$R^{7'}$ is selected from $C_1$-$C_8$ alkyl, —O—$C_1$-$C_8$ alkyl, benzyl, —O-benzyl, —$CH_2$—$C_3$-$C_6$ cycloalkyl, and $CF_3$; or c) $R^4$ and $R^{4'}$ combine to form the structure selected from:

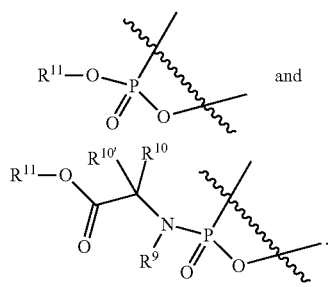

and

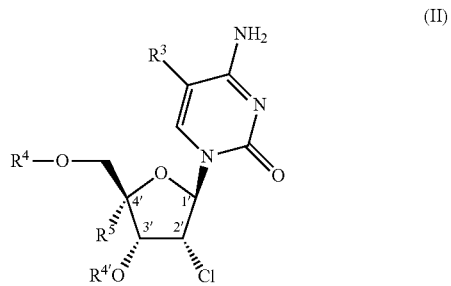

2. A compound according to claim 1 of Formula (II), or a pharmaceutically acceptable salt thereof:

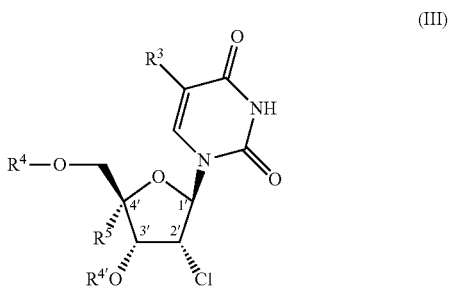

wherein $R^3$, $R^4$, $R^{4'}$, and $R^5$ are as defined in claim 1.

3. A compound according to claim 1 of Formula (III), or a pharmaceutically acceptable salt thereof:

(III)

wherein $R^3$, $R^4$, $R^{4'}$, and $R^5$ are as defined in claim 1.

4. A compound according to claim 1, or a pharmaceutically acceptable salt thereof, wherein $R^{4'}$ is hydrogen.

5. A compound according to claim 1, or a pharmaceutically acceptable salt thereof, wherein $R^5$ is selected from the group of CN; unsubstituted $C_1$-$C_3$ alkyl; $C_1$-$C_3$ alkyl substituted with 1, 2, or 3 halogens selected from F and Cl; $C_1$-$C_3$ alkyl substituted with 1 substituent selected from —S—$CH_3$ and —O—$CH_3$; $C_2$-$C_3$ alkenyl; $C_2$-$C_3$ alkynyl; unsubstituted $C_3$-$C_5$ cycloalkyl; and $C_3$-$C_5$ cycloalkyl substituted by 1, 2, or 3 substituents selected from F and $CH_3$.

6. A compound according to claim 1, or a pharmaceutically acceptable salt thereof, wherein $R^3$ is hydrogen.

7. A compound according to claim 1, or a pharmaceutically acceptable salt thereof, wherein $R^3$ is F.

8. A compound according to claim 1, or a pharmaceutically acceptable salt thereof, wherein $R^3$ and $R^4$ are both hydrogen.

9. A compound according to claim 1, or a pharmaceutically acceptable salt thereof, wherein $R^3$, $R^4$, and $R^{4'}$ are each hydrogen.

10. A compound according to claim 1, or a pharmaceutically acceptable salt thereof, wherein $R^3$ is F and $R^4$ and $R^{4'}$ are each hydrogen.

11. A compound according to claim 1, or a pharmaceutically acceptable salt thereof, wherein $R^3$ is selected from the group of H and F; $R^5$ is selected from the group of CN, methyl, ethyl, propyl, vinyl, propenyl, ethynyl, $CH_2F$, $CHF_2$, $CH_2Cl$, $CH_2SMe$, —$CH_2OMe$, and cyclopropyl; $R^4$ is H; and $R^{4'}$ is hydrogen.

12. A compound according to claim 1, or a pharmaceutically acceptable salt thereof, wherein $R^4$ is selected from:

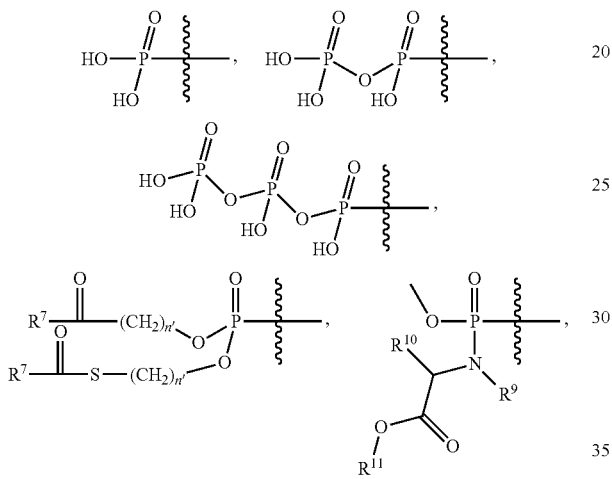

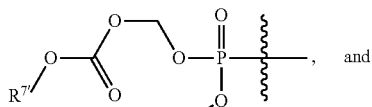

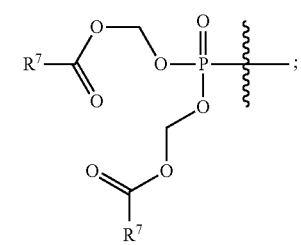

wherein:

n' is selected from 1, 2, 3, and 4;

$R^7$ is selected from $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$;

$R^{7'}$ is selected from $C_1$-$C_8$ alkyl, —O—$C_1$-$C_8$ alkyl, benzyl, —O-benzyl, —$CH_2$—$C_3$-$C_6$ cycloalkyl, and $CF_3$;

$R^8$ is selected from phenyl, 1-naphthyl, 2-naphthyl,

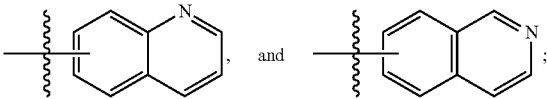

$R^9$ is selected from H and $CH_3$;

$R^{10}$ is selected from H or $C_1$-$C_6$ alkyl;

$R^{11}$ is selected from H, $C_1$-$C_8$ alkyl, benzyl, $C_3$-$C_6$ cycloalkyl, and —$CH_2$—$C_3$-$C_6$ cycloalkyl.

13. A compound according to claim 1, or a pharmaceutically acceptable salt thereof, wherein $R^4$ is selected from:

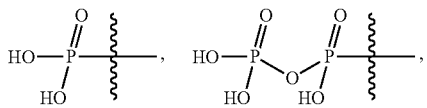

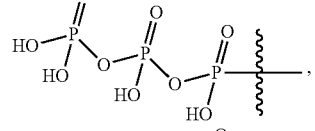

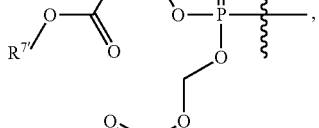

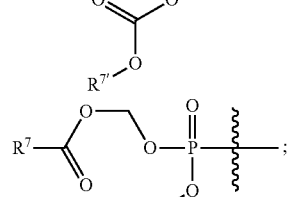

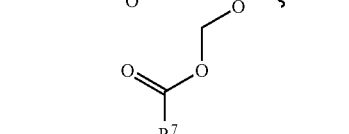

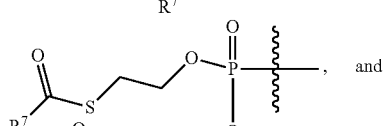

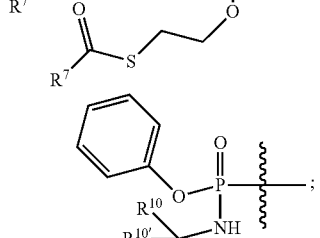

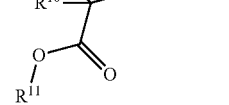

wherein:
R$^7$ is selected from C$_1$-C$_8$ alkyl, —O—C$_1$-C$_8$ alkyl, benzyl, and —CH$_2$—C$_3$-C$_6$ cycloalkyl;
R$^{7\prime}$ is selected from C$_1$-C$_8$ alkyl, —O—C$_1$-C$_8$ alkyl, benzyl, —O-benzyl, —CH$_2$—C$_3$-C$_6$ cycloalkyl, and CF$_3$;
R$^{10}$ is selected from H or C$_1$-C$_6$ alkyl;
R$^{10\prime}$ is selected from H or C$_1$-C$_6$ alkyl;
or R$^{10}$ and R$^{10\prime}$, together with the carbon atom to which they are bound, form a 3-, 4-, 5-, or 6-membered spirocycle wherein all ring atoms of the spirocycle are carbon;
or R$^{10}$ and R$^{10\prime}$, together with the carbon atom to which they are bound, form a 3-, 4-, 5-, or 6-membered spirocycle wherein 1 or 2 of the ring atoms of the spirocycle are selected from the group of O, S, and N, and all other ring atoms of the spirocycle are carbon; and
R$^{11}$ is selected from C$_1$-C$_8$ alkyl, benzyl, C$_3$-C$_6$ cycloalkyl, and —CH$_2$—C$_3$-C$_6$ cycloalkyl.

14. A compound according to claim 1, or a pharmaceutically acceptable salt thereof, wherein:
R$^3$ is selected from the group of H and F;
R$^{4\prime}$ is hydrogen;
R$^5$ is selected from the group of CN, methyl, ethyl, propyl, vinyl, propenyl, ethynyl, CH$_2$F, CHF$_2$, CH$_2$Cl, CH$_2$SMe, —CH$_2$OMe, and cyclopropyl; and
R$^4$ is selected from the group of:

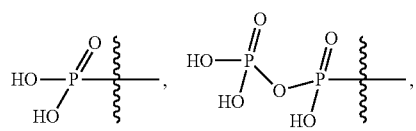

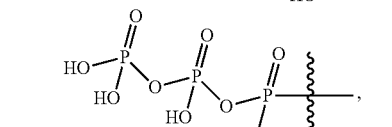

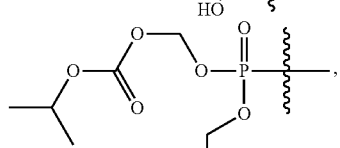

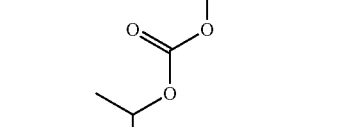

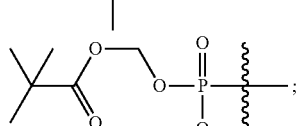

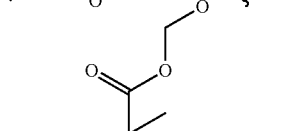

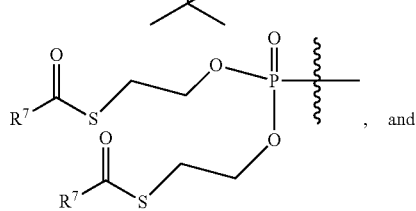

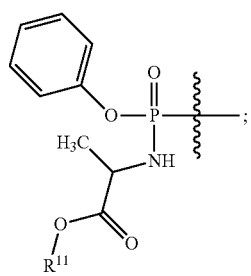

wherein:
R$^7$ is selected from C$_1$-C$_8$ alkyl, —O—C$_1$-C$_8$ alkyl, benzyl, and —CH$_2$—C$_3$-C$_6$ cycloalkyl; and
R$^{11}$ is selected from C$_1$-C$_8$ alkyl, benzyl, C$_3$-C$_6$ cycloalkyl, and —CH$_2$—C$_3$-C$_6$ cycloalkyl.

15. A compound according to claim 14, or a pharmaceutically acceptable salt thereof, wherein R$^4$ is selected from:

(a)
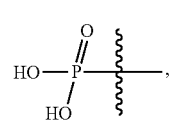

(b)
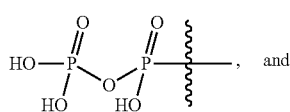
and (c)
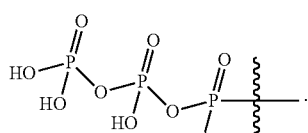

16. A compound of claim 1 selected from the group of:

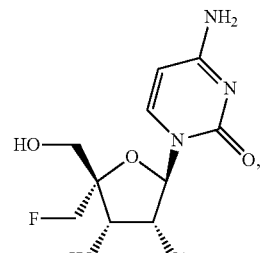

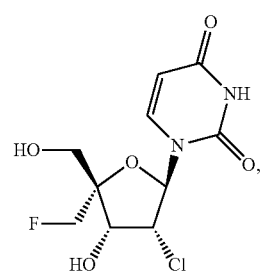

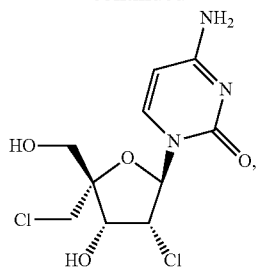
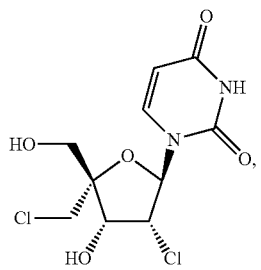
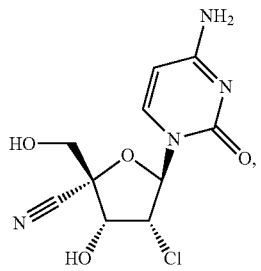
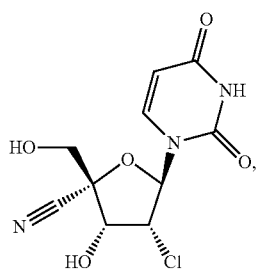
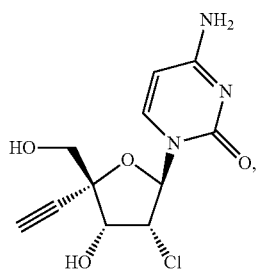
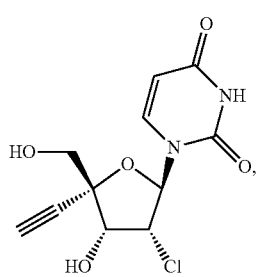
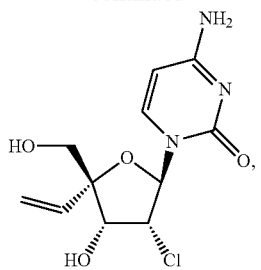
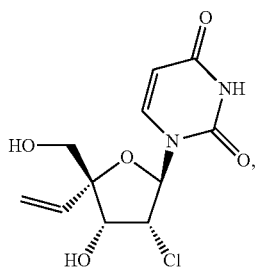
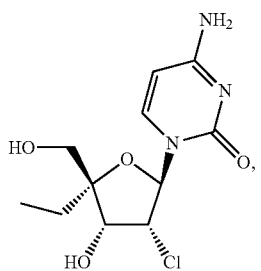
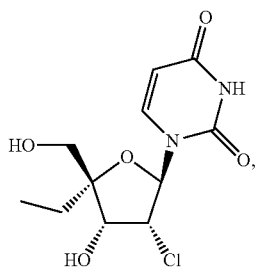
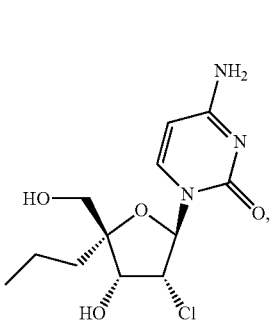
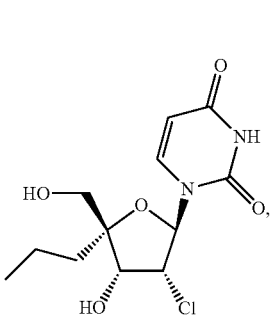

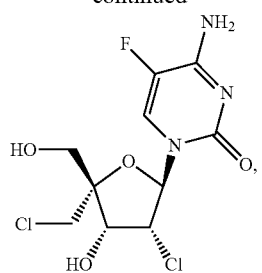
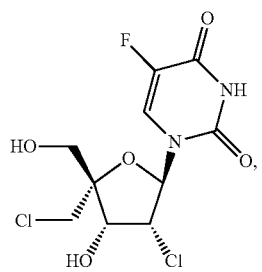
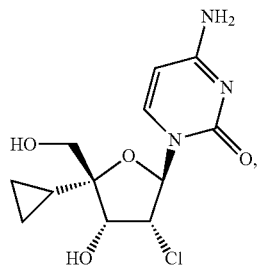
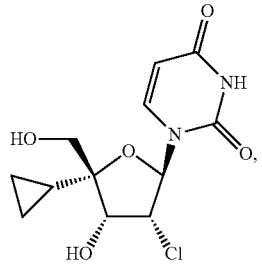
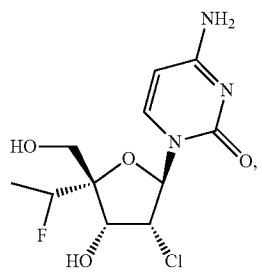
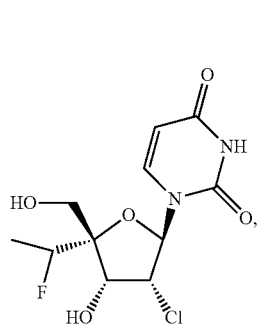
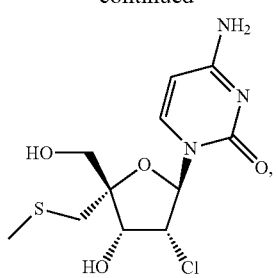
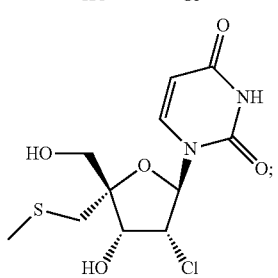
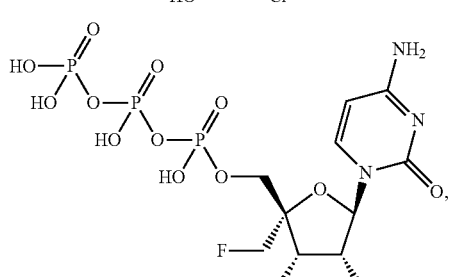
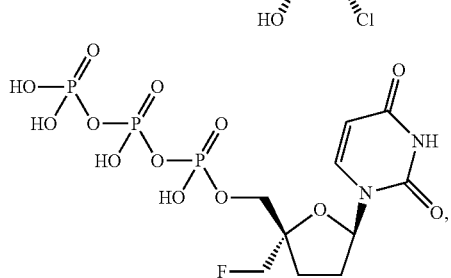
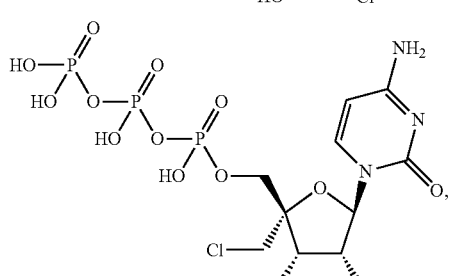
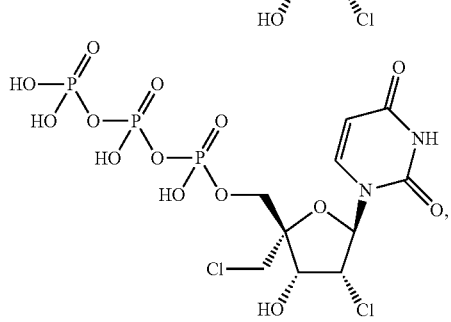

97
-continued
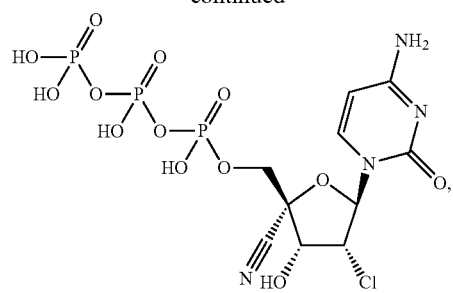
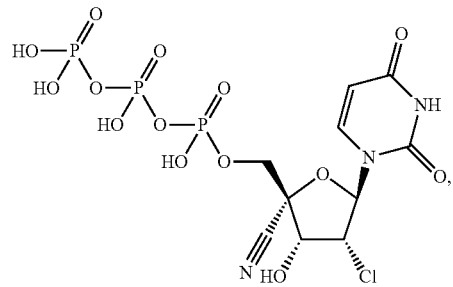
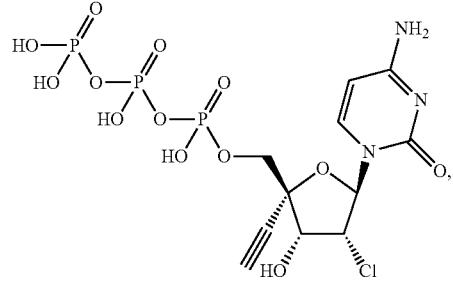
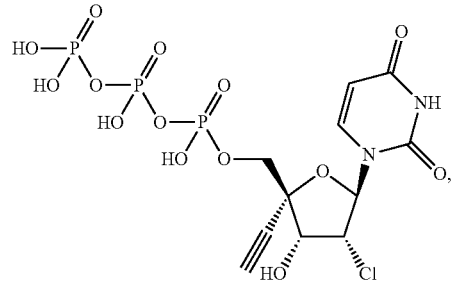
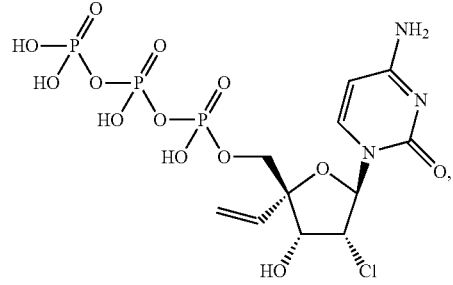
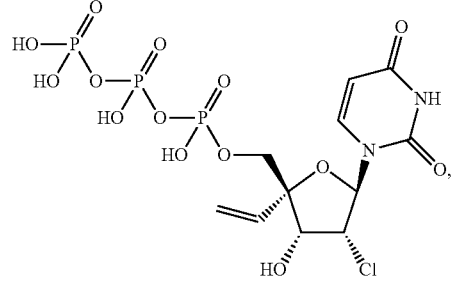
98
-continued
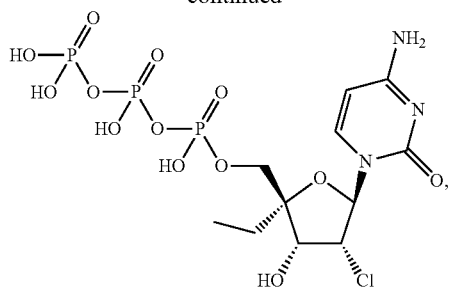
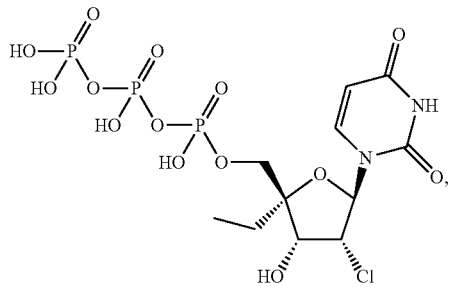
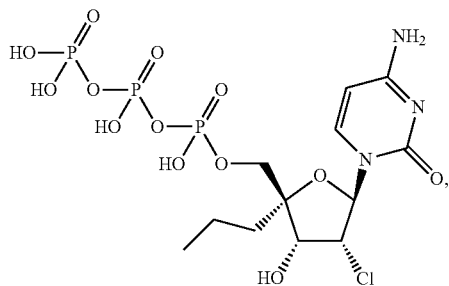
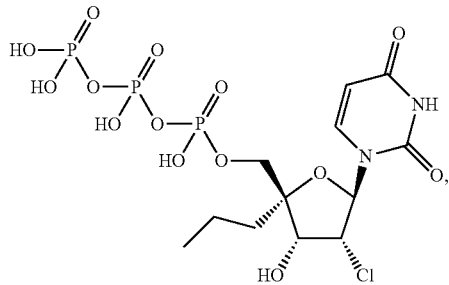
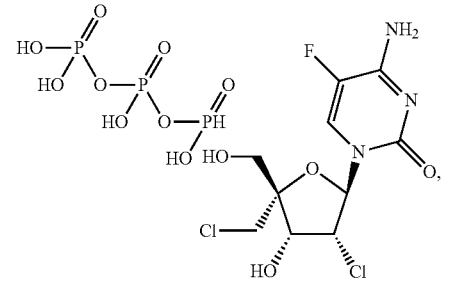
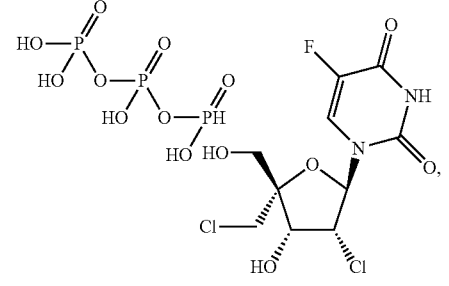

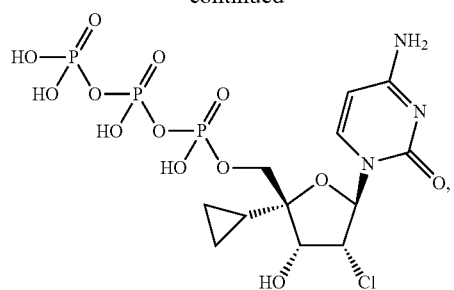

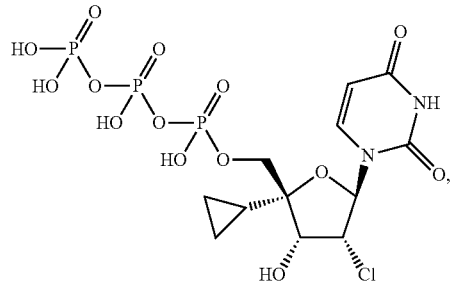

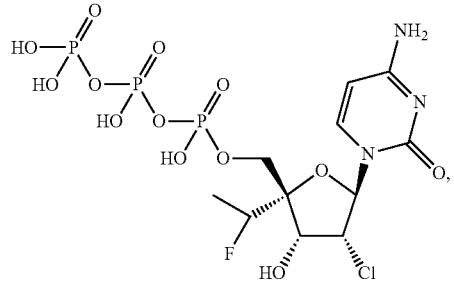

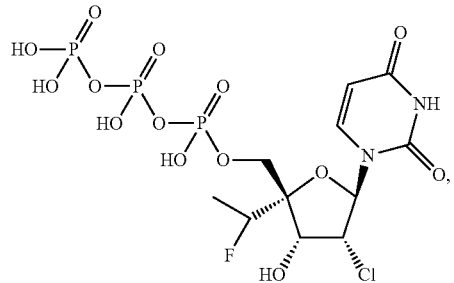

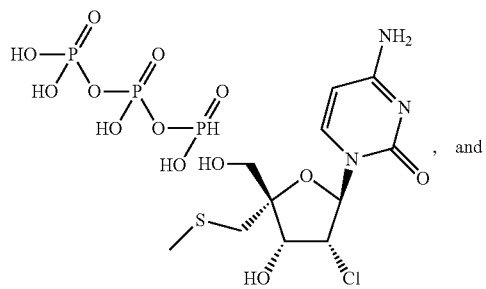

, and

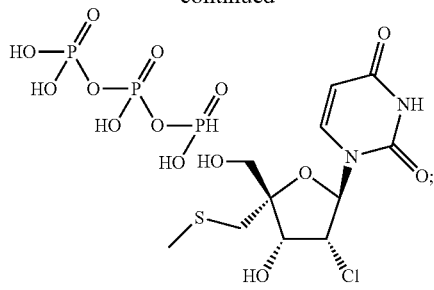

or a pharmaceutically acceptable salt thereof.

17. A compound of claim 1 of the formula:

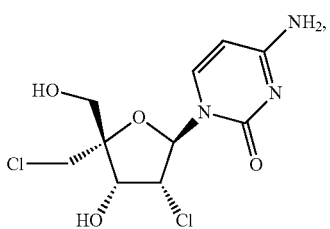 [SMILES: Nc1ccn([C@@H]2O[C@@](CO)(CCl)[C@@H](O)[C@H]2Cl)c(=O)n1]

or a pharmaceutically acceptable salt thereof.

18. A compound of claim 1 of the formula:

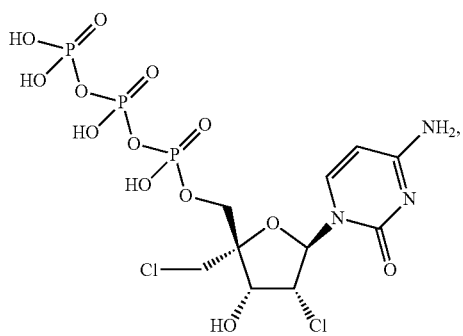 [SMILES: Nc1ccn([C@@H]2O[C@](CCl)(COP(=O)(O)OP(=O)(O)OP(=O)(O)O)[C@@H](O)[C@H]2Cl)c(=O)n1]

or a pharmaceutically acceptable salt thereof.

19. A method of treating Pneumovirinae virus infection in a human, the method comprising administering to the human a therapeutically effective amount of a compound of claim 1, or a pharmaceutically acceptable salt thereof.

20. A method of treating human respiratory syncytial virus infection in a human, the method comprising administering to the human a therapeutically effective amount of a compound of claim 1, or a pharmaceutically acceptable salt thereof.

21. A pharmaceutical composition comprising a compound of claim 1, or a pharmaceutically acceptable salt thereof, and a pharmaceutically acceptable carrier or excipient.

\* \* \* \* \*